(12) United States Patent
Heavner et al.

(10) Patent No.: US 7,288,390 B2
(45) Date of Patent: Oct. 30, 2007

(54) ANTI-DUAL INTEGRIN ANTIBODIES, COMPOSITIONS, METHODS AND USES

(75) Inventors: George Heavner, Malvern, PA (US); Jill Giles-Komar, Downingtown, PA (US); Linda Snyder, Pottstown, PA (US); Mohit Trikha, Paoli, PA (US)

(73) Assignee: Centocor, Inc., Malvern, PA (US)

( * ) Notice: Subject to any disclaimer, the term of this patent is extended or adjusted under 35 U.S.C. 154(b) by 1374 days.

(21) Appl. No.: 09/920,267

(22) Filed: Aug. 1, 2001

(65) Prior Publication Data

US 2003/0040044 A1     Feb. 27, 2003

Related U.S. Application Data

(60) Provisional application No. 60/223,363, filed on Aug. 7, 2000.

(51) Int. Cl.
| | |
|---|---|
| G12P 21/06 | (2006.01) |
| C12N 15/87 | (2006.01) |
| C12N 9/96 | (2006.01) |
| C12N 5/02 | (2006.01) |
| C12N 5/20 | (2006.01) |
| C12N 1/20 | (2006.01) |
| C07H 21/04 | (2006.01) |

(52) U.S. Cl. ............... 435/69.1; 435/445; 435/326; 435/252.3; 435/320.1; 536/23.53

(58) Field of Classification Search ............ None
See application file for complete search history.

(56) References Cited

U.S. PATENT DOCUMENTS

| | | | |
|---|---|---|---|
| 5,674,483 A | 10/1997 | Tu et al. | |
| 5,753,230 A | 5/1998 | Brooks et al. | |
| 5,877,397 A | 3/1999 | Lonberg et al. | |
| 5,985,278 A | 11/1999 | Mitjans et al. | |
| 6,171,588 B1 | 1/2001 | Carron et al. | |
| 6,342,221 B1 | 1/2002 | Thorpe et al. | |
| 6,359,126 B1 | 3/2002 | Kim et al. | |
| 6,369,204 B1 | 4/2002 | Kim et al. | |
| 6,632,927 B2 | 10/2003 | Adair et al. | |
| 2001/0011125 A1 | 8/2001 | Huse | |
| 2003/0143603 A1* | 7/2003 | Giles-Komar et al. | 435/6 |

FOREIGN PATENT DOCUMENTS

| | | |
|---|---|---|
| EP | 0 260 829 | 3/1988 |
| EP | 719859 A1 | 7/1996 |
| EP | 0 834 557 | 4/1998 |
| WO | WO93/20229 | 10/1993 |
| WO | WO94/12181 A1 | 6/1994 |
| WO | WO95/25543 A1 | 9/1995 |
| WO | WO97/06791 A1 | 2/1997 |
| WO | WO97/36859 A1 | 10/1997 |
| WO | WO 0031248 A | 6/2000 |
| WO | WO 0044404 A | 8/2000 |

OTHER PUBLICATIONS

Rudikoff et al Single amino acid substitution altering antigen-binding specificity. Proc Natl Acad Sci U S A. Mar. 1982;79(6):1979-83.*

Gunther Gastl, Thomas Hermann, Michael Steurer, Jorg Zmija, Eberhard Gunsilius, Clemens Unger, and Andrea Kraft, "Angiogenesis as a target for tumor treatment", Oncology, 1997, 177-84, vol. 54.

Brian P. Eliceiri and David A. Cheresh, "The Role of alpha-v integrins during angiogenesis: insights into potential mechanisms of action and clinical development", The Journal of Clinical Investigation, May 1999, 1227-30, vol. 103, No. 9.

Martin Friedlander, Peter C. Brooks, Robert W. Shaffer, Christine M. Kincaid, Judith A. Varner, and David A. Cherish, "Definition of two angiogenic pathways by distinct alpha-v integrins", Science, Dec. 1 1995, 1500-2, vol. 270.

Lisa D. Taylor, Condie E. Carmack, Dennis Huszar, Kay M. Higgins, Roshanak Mashayekh, Getachew Sequar, Stephen R. Schramm, Chiung-Chi Kuo, Susan L. O'Donnell, Robert M. Kay, Clive S. Woodhouse, and Nils Lonberg, "Human immunoglobulin transgenes undergo rearrangement, somatic mutation and class switching in mice that lack endogenous IgM", International Immunology, 1994; 579-91, vol. 6, No. 4, Oxford University Press.

Nils Lonberg, Lisa D. Taylor, Fiona A. Harding, Mary Trounstine, Kay M. Higgins, Stephen R. Schramm, Chiung-Chi Kuo, Roshanak Mashayekh, Kathryn Wymore, James G. McCabe, Donna Munoz-O'Regan, Susan L. O'Donnell, Elizabeth S. G. Lapachet, Tasha Bengoechea, Dianne M. Fishwild, Condie E. Carmack, Robert M. Kay, and Dennis Huszar, "Antigen-specific human antibodies from mice comprising four distinct genetic modifications", Nature, Apr. 28, 1994, 856-9, vol. 368.

Michael Neuberger, "Generating high-avidity human Mabs in mice", Nature Biotechnology, Jul. 1996, 826, vol. 14.

Dianne M. Fishwild, Susan L. O'Donnell, Tasha Bengoechea, Debra V. Hudson, Fiona Harding, Susan L. Bernhard, Debbie Jones, Robert M. Kay, Kay M. Higgins, Stephen R. Schramm, and Nils Lonberg, "High-avidity human IgG-kappa monoclonal antibodies from a novel strain of minitocus transgenic mice", Nature Biotechnology, Jul. 1996, 845-51, vol. 14.

Elizabeth A. Wayner, Robert A. Orlando, and David A. Cheresh, "Integrins alpha v beta 3 and alpha v beta 5 Contribute to Cell Attachment to Vitronectin but Differentially Distribute on the Cell Surface", J. Cell Biology, May 1991, 919-29, vol. 113, No. 4.

John F. Marshall, Deborah C. Rutherford, Alison C.E. McCartney, Francesc Mitjans, Simon L. Goodman, and Ian R. Hart, "Alpha v beta 1 is a receptor for vitronectin and fibrinogen, and acts with alpha 5 beta 1 to mediate spreading on fibronectin", J. of Cell Science, 1995, 1227-38, vol. 108.

(Continued)

Primary Examiner—Maher M. Haddad
(74) Attorney, Agent, or Firm—Kenneth J. Dow

(57) ABSTRACT

The present invention relates to at least one novel anti-dual integrin antibodies, including isolated nucleic acids that encode at least one anti-dual integrin antibody, dual integrin, vectors, host cells, transgenic animals or plants, and methods of making and using thereof, including therapeutic compositions, methods and devices.

14 Claims, 30 Drawing Sheets

OTHER PUBLICATIONS

David A. Cheresh and Robert C. Spiro, "Biosynthetic and Functional Properties of an Arg-Gly-Asp-directed Receptor Involved in Human Melanoma Cell Attachment to Vitronectin, Fibrinogen, and von Willebrand Factor", J. of Biological Chemistry, Dec. 25, 1987, 17703-11, vol. 262, No. 36.

Hans Kemperman, Yvonne M. Wijnands, and Ed Roos, "Alpha v Integrins on HT-29 Colon Carcinoma Cells: Adhesion to Fibronectin is Mediated Solely by Small Amounts of alpha v beta 6, and alpha v beta 5 is Codistributed with Actin Fibers", Experimental Cell Research, 1997, 156-64, vol. 234.

Maxime Lehmann, Chantal Rabenandrasana, Richard Tamura, Jean-Claude Lissitzky, Vito Quaranta, Jacques Pichon, and Jacques Marvaldi, "A Monoclonal Antibody Inhibits Adhesion to Fibronectin and Vitronectin of a Colon Carcinoma Cell Line and Reconginzes the Integrins alpha v beta 3, alpha v beta 5, and alpha v beta 6", Cancer Research, Apr. 15, 1994, 2102-07, vol. 54.

Tam, S., et al.: "Abciximab (ReoPro, chimeric 7E3 Fab) demonstrates equivalent alfinity and functional blockade of glycoprotein IIB/IIIa and alpha (v) beta2 integrins" vol., 98, No. 11, Sep. 15, 1998, pp. 1085-1091, XP000882678.

Trikha, M. et al.: "A potential new application for a cardiovascular drug: Role for ReoPro (Abciximab), an inhibitor of gpIIb/IIIa and alphaVbeta3 integrins, as an anti-cancer agent", Proceedings of the American Association for Cancer Research, vol. 41, Mar. 2000, p. 577, XP002212901.

Suzuki, S., et al.: "cDNA and amino acid sequences of the cell adhesion protein receptor recognizing vitronectin reveal a transmembrane domain and homologies with other adhesion protein receptors". Proceedings of the National Academy of Sciences of the U.S.A., vol. 83, No. 22, Nov. 1986, pp. 8614-8618, XP002212902.

Mitjans et al, "In Vivo Therapy of Malignant Melanoma by Means of Antagonists of αv Integrins," Int. J. Cancer, 2000, pp. 716-723, vol. 87, Wiley-Liss, Inc., Spain.

Mitjans et al, "An anti-αv-integrin antibody that blocks integrin function inhibits the development of a human melanoma in nude mice," Journal of Cell Science, 1995, pp. 2825-2838, vol. 108, The Company of Biologists Limited, Great Britain.

Casel et al, "RGD Peptides and Moncolonal Antibodies, Antagonists of $α_v$-Integrin, Enter the Cells by Independent Endocytic Pathways," Laboratory Investigation, 2001, pp. 1615-1626, vol. 81, No. 12, The United States and Canadian Academy of Pathology, Inc., USA.

Panka et. al., Variable Region Framework Differences Result In Decreased Or Increased Affinity Of Variant Anti-Digoxin Antibodies, Proc. Natl. Acad. Sci. U.S.A. 85(9); 3080-3084, 1988.

Amit, et. al., Three-Dimensional Structure Of An Antigen-Antibody Complex At 2.8 Resolution. Science. 233 (4765); 747-753, 1986.

Wayner et. al., Integrins Alpha V Beta 3 And Alpha V Beta 5 Contribute To Cell Attachment To Vitronectin But Differentially Distribute on the Cell Surface. J. Cell Biol. May 1991; 113(4);919-29.

J. Orihara, Sensitizing Capacity, Cross- Reactivity And Antigenic Determinants Of Bisphenal A, The Journal Of Stomatological Society, vol. 59, No. 2, Jun. 1992, pp. 439-455, English Abstract.

M. Castillo et. al., "Analysis Of Industrial Effluents To Determine Endocrine-Disrupting Chemicals", Trends In Analytical Chemistry vol. 16, No. 10, Nov. 12, 1997, pp. 574-583.

J. Gascon et. al. "Detection Of Endocrine-Disrupting Pesticides By Enzyme-Linked Immunosorbent Assay (Elisa); Application To Atrazine" Trends In Analytical Chemistry, vol. 16, No. 10, 1997, pp. 554-562.

Friendlander et. al, Proc Natl Acad Sci, 1996, pp. 9764-9769, vol. 93.

Chemicon International Catalog No. MAB1953Z, p. 1, Jan. 27, 2006.

* cited by examiner

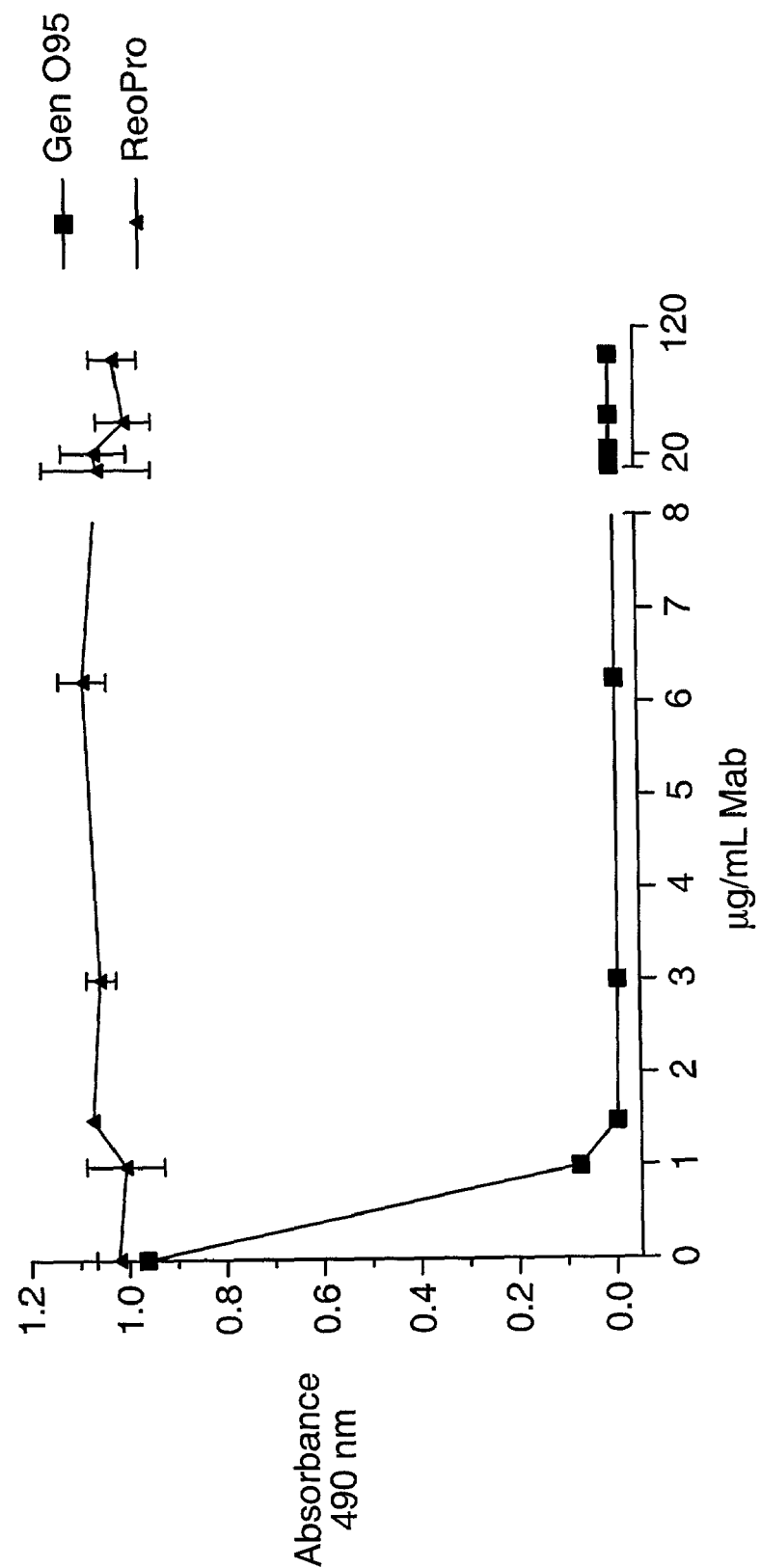

Binding of αVβ3 to GenO95 Plate in presence of 50 mM EDTA (no $Ca^{++}$) or with $Ca^{++}$ alone Binding of αVβ3 to C372A Plate in presence of 50 mM EDTA (no $Ca^{++}$) or with $Ca^{++}$ alone Binding of αVβ3 to c7E3 IgG Plate in presence of 50 mM EDTA (no Ca$^{++}$) or with Ca$^{++}$ alone Binding of αVβ3 to LM609 IgG Plate in presence of 50 mM EDTA (no Ca$^{++}$) or with Ca$^{++}$ alone

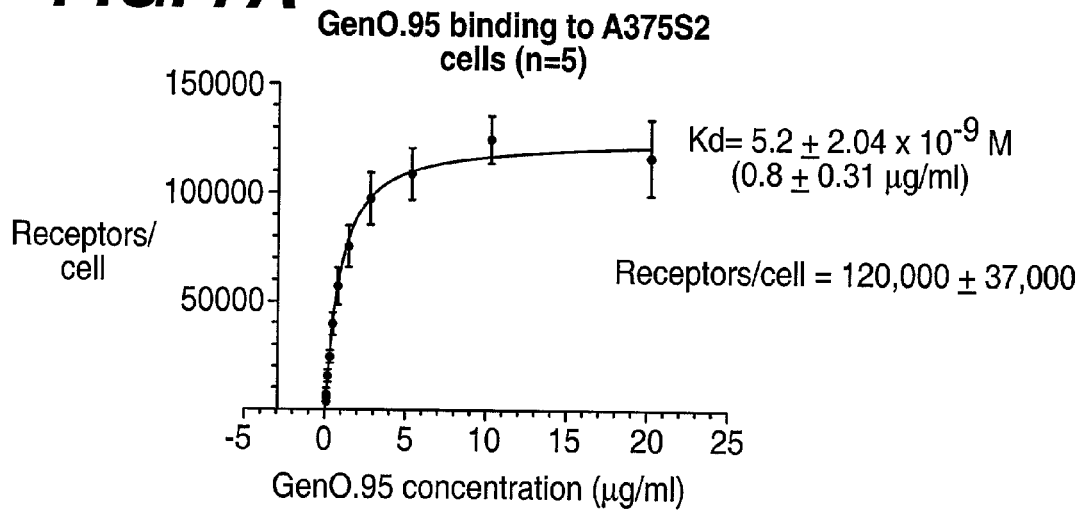
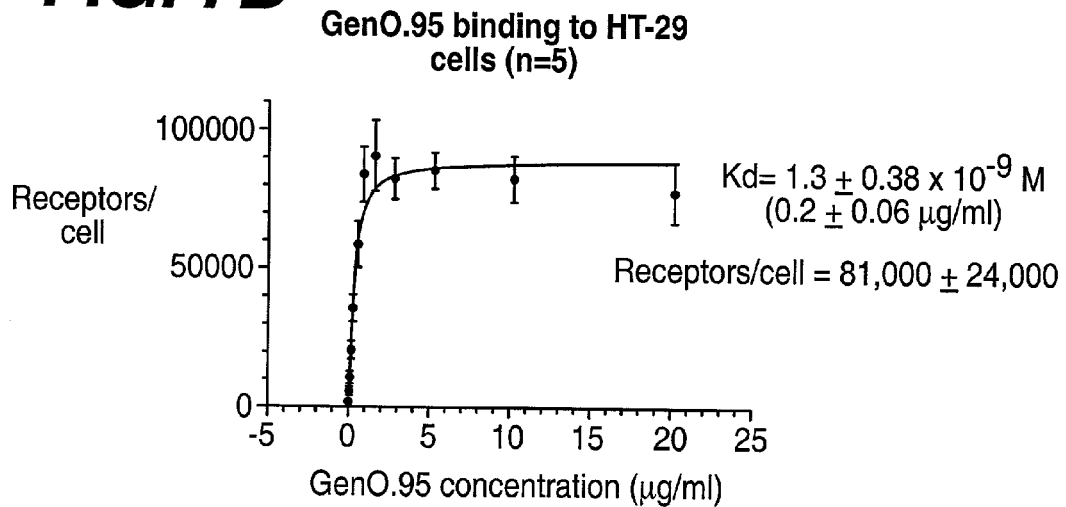
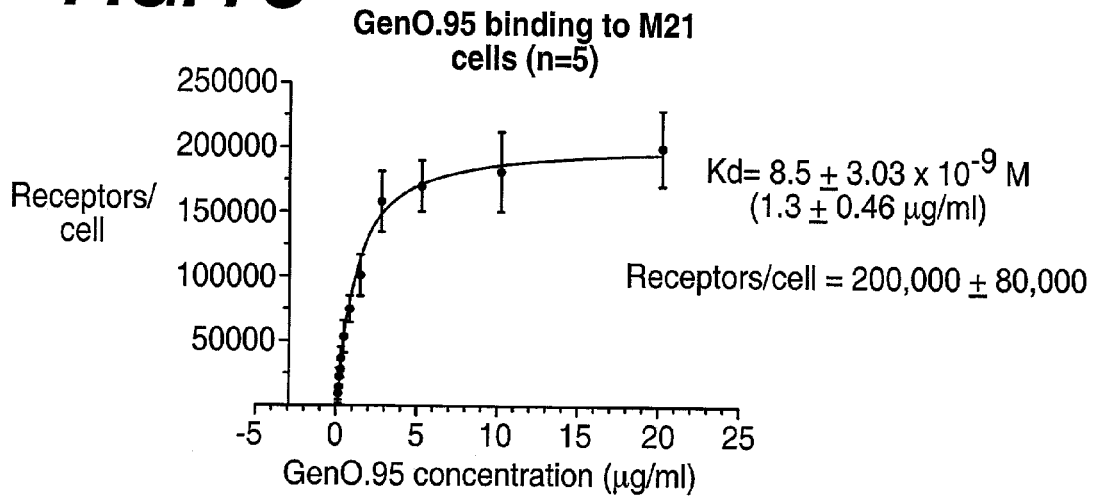

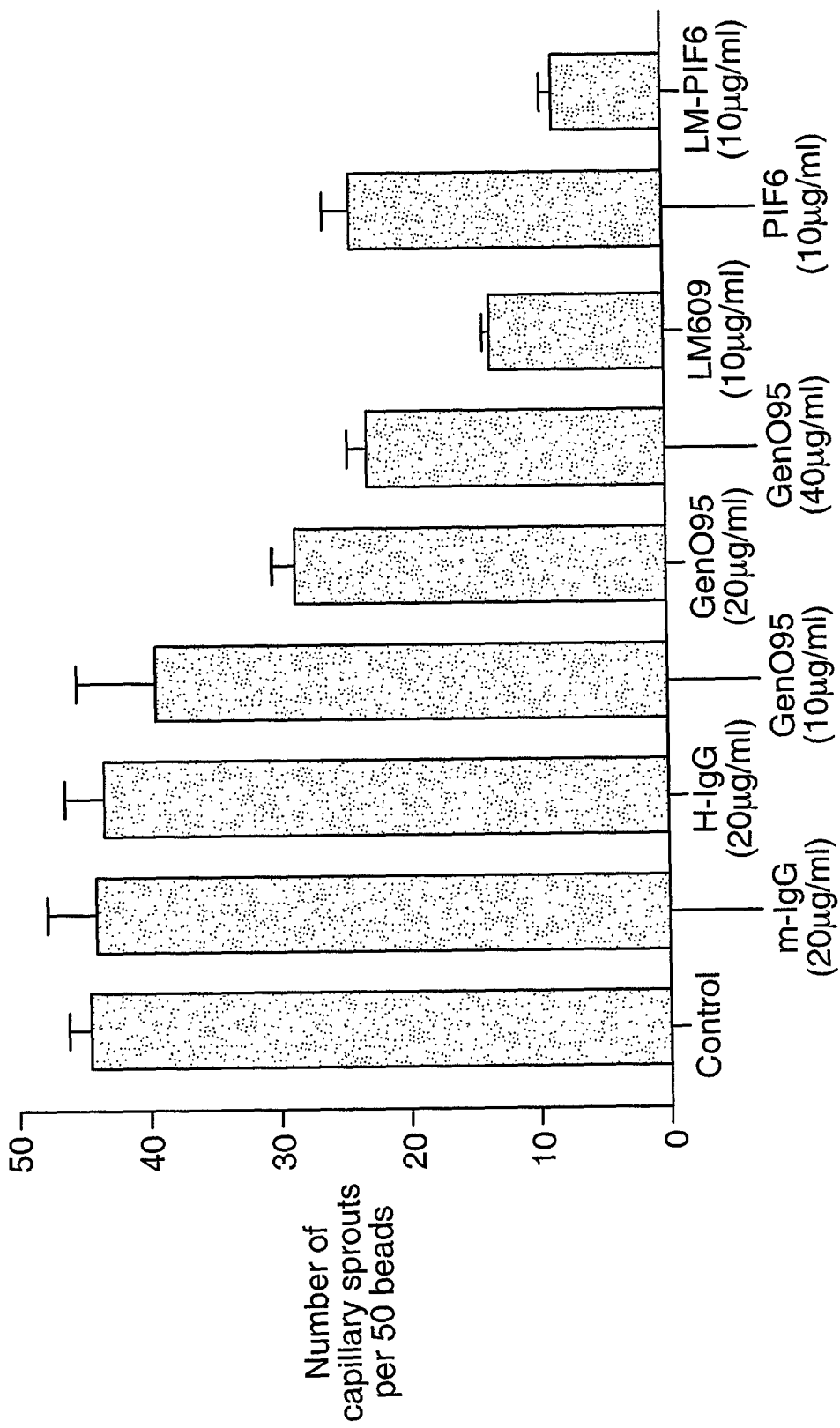

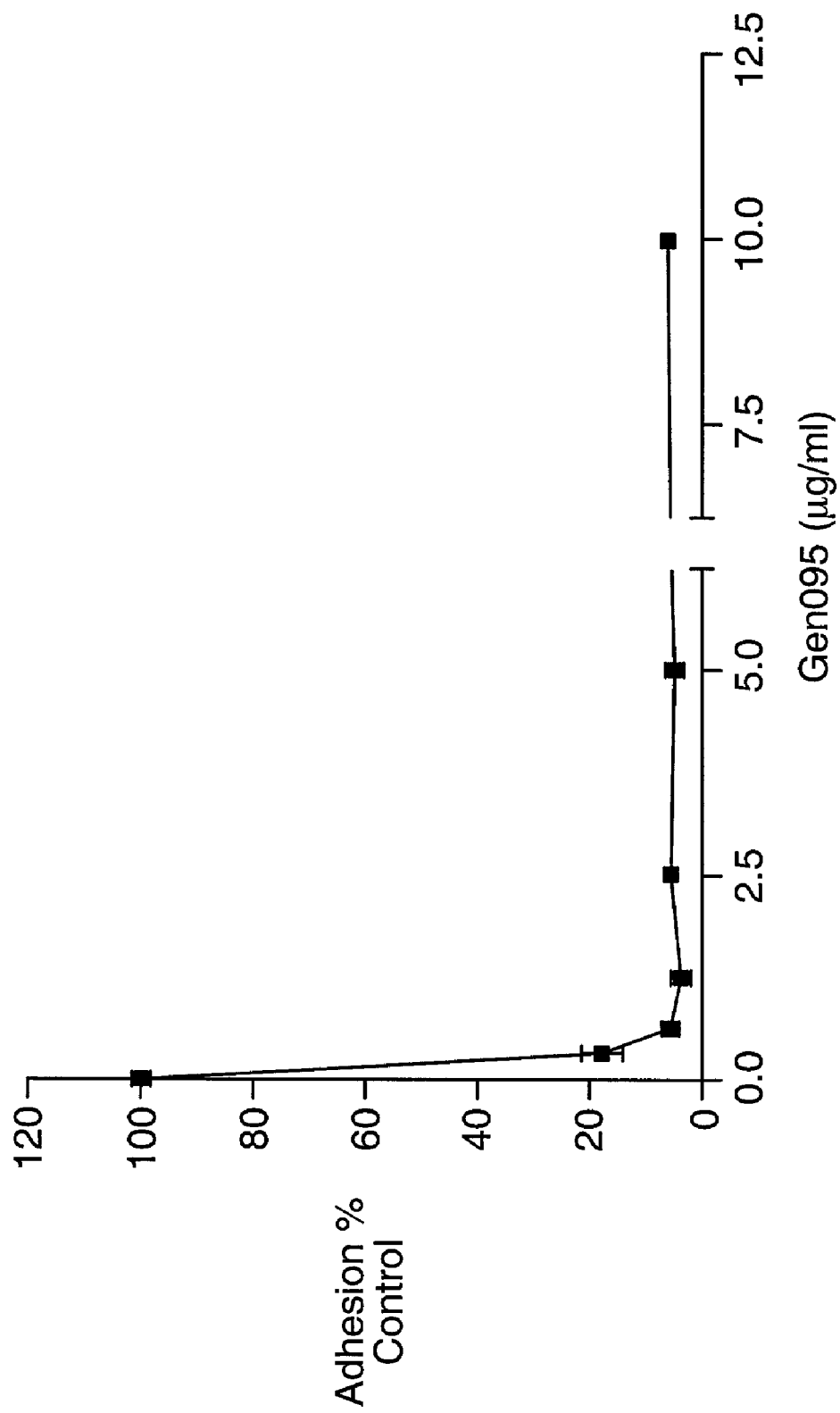

FIG. 16A   FIG. 16B   FIG. 16C
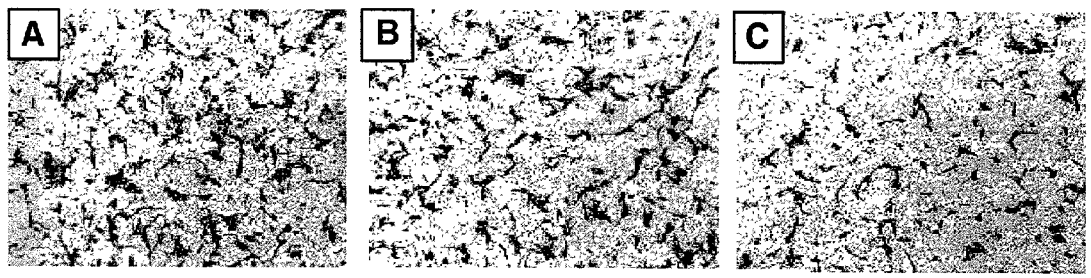
FIG. 16D
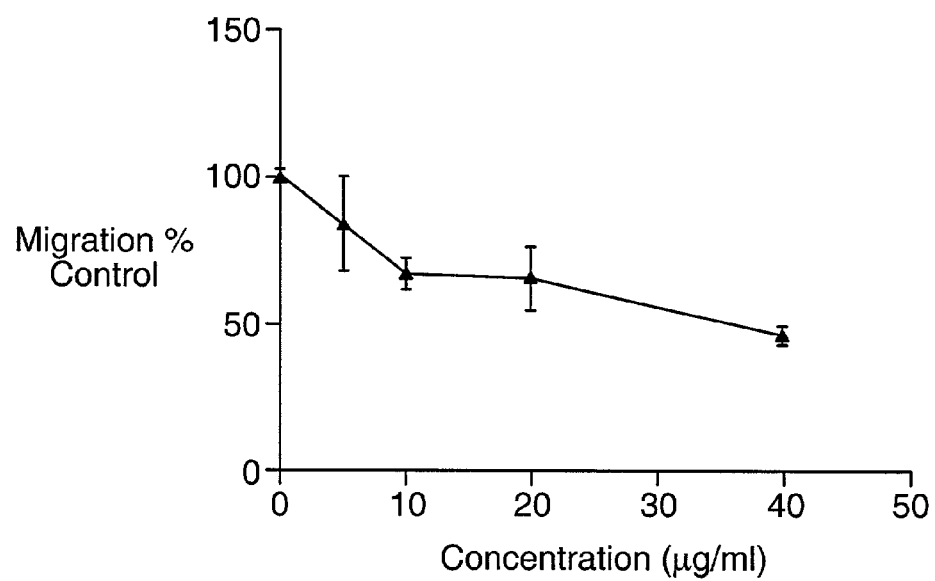

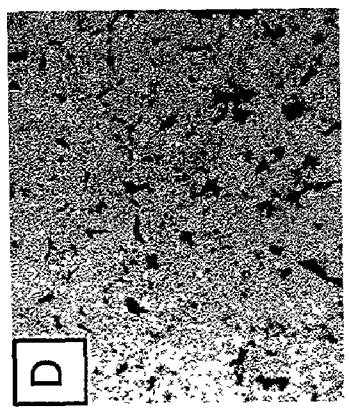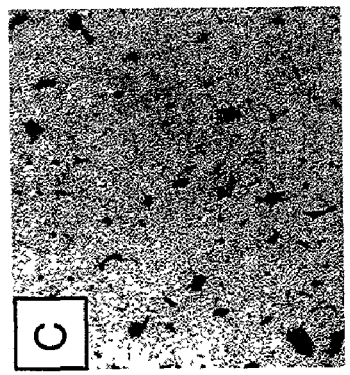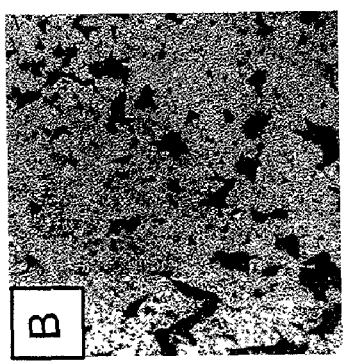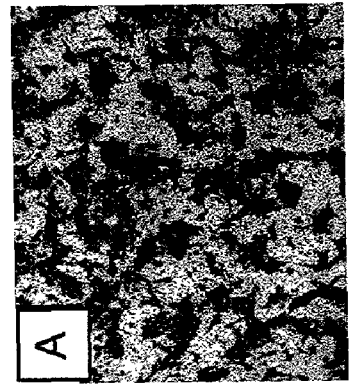
FIG. 20D
FIG. 20C
FIG. 20B
FIG. 20A

ANTI-DUAL INTEGRIN ANTIBODIES, COMPOSITIONS, METHODS AND USES

This application claims benefit of Ser. No. 60/223,363 filed Aug. 7, 2,000.

BACKGROUND OF THE INVENTION

1. Field of the Invention

This application is based in part on, and claims priority to, U.S. Provisional No. 60/223,363 filed Aug. 7, 2000, of which is entirely incorporated herein by reference.

The present invention relates to antibodies, including specified portions or variants, specific for at least one alpha-v-beta3, alpha-v-beta5 dual integrin (dual integrin) protein or fragment thereof, as well as nucleic acids encoding such anti-dual integrin antibodies, complementary nucleic acids, vectors, host cells, and methods of making and using thereof, including therapeutic formulations, administration and devices.

2. Related Art

There is now considerable evidence that progressive tumor growth is dependent upon angiogenesis, the formation of new blood vessels, to provide tumors with nutrients and oxygen, to carry away waste products and to act as conduits for the metastasis of tumor cells to distant sites (Gastl et al., Oncol. 54:177–184). Recent studies have further defined the roles of integrins in the angiogenic process. Integrins are heterodimeric transmembrane proteins that play critical roles in cell adhesion to the extracellular matrix (ECM) which, in turn, mediates cell survival, proliferation and migration through intracellular signaling. During angiogenesis, a number of integrins that are expressed on the surface of activated endothelial cells regulate critical adhesive interactions with a variety of ECM proteins to regulate distinct biological events such as cell migration, proliferation and differentiation. Specifically, the closely related but distinct integrins aVb 3 and aVb 5 have been shown to mediate independent pathways in the angiogenic process. An antibody generated against $\alpha V\beta 3$ blocked basic fibroblast growth factor (bFGF) induced angiogenesis, whereas an antibody specific to $\alpha V\beta 5$ inhibited vascular endothelial growth factor (VEGF) induced angiogenesis (Eliceiri, et al., J. Clin. Invest. 103: 1227–1230 (1999); Friedlander et al., Science 270: 1500–1502 (1995)).

Non-human mammalian, chimeric, polyclonal (e.g., antisera) and/or monoclonal antibodies (Mabs) and fragments (e.g., proteolytic digestion or fusion protein products thereof) are potential therapeutic agents that are being investigated in some cases to attempt to treat certain diseases. However, such antibodies or fragments can elicit an immune response when administered to humans. Such an immune response can result in an immune complex-mediated clearance of the antibodies or fragments from the circulation, and make repeated administration unsuitable for therapy, thereby reducing the therapeutic benefit to the patient and limiting the readministration of the antibody or fragment. For example, repeated administration of antibodies or fragments comprising non-human portions can lead to serum sickness and/or anaphalaxis. In order to avoid these and other problems, a number of approaches have been taken to reduce the immunogenicity of such antibodies and portions thereof, including chimerization and humanization, as well known in the art. These and other approaches, however, still can result in antibodies or fragments having some immunogenicity, low affinity, low avidity, or with problems in cell culture, scale up, production, and/or low yields. Thus, such antibodies or fragments can be less than ideally suited for manufacture or use as therapeutic proteins.

Accordingly, there is a need to provide anti-dual integrin antibodies or fragments that overcome one more of these problems, as well as improvements over known antibodies or fragments thereof.

SUMMARY OF THE INVENTION

The present invention provides isolated human, primate, rodent, mammalian, chimeric, humanized and/or CDR-grafted anti-dual integrin antibodies, immunoglobulins, cleavage products and other specified portions and variants thereof, as well as anti-dual integrin antibody compositions, encoding or complementary nucleic acids, vectors, host cells, compositions, formulations, devices, transgenic animals, transgenic plants, and methods of making and using thereof, as described and enabled herein, in combination with what is known in the art.

The present invention also provides at least one isolated anti-dual integrin antibody as described herein. An antibody according to the present invention includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that can be incorporated into an antibody of the present invention. An antibody of the invention can include or be derived from any mammal, such as but not limited to a human, a mouse, a rabbit, a rat, a rodent, a primate, or any combination thereof, and the like.

The present invention provides, in one aspect, isolated nucleic acid molecules comprising, complementary, or hybridizing to, a polynucleotide encoding specific anti-dual integrin antibodies, comprising at least one specified sequence, domain, portion or variant thereof. The present invention further provides recombinant vectors comprising said anti-dual integrin antibody nucleic acid molecules, host cells containing such nucleic acids and/or recombinant vectors, as well as methods of making and/or using such antibody nucleic acids, vectors and/or host cells.

At least one antibody of the invention binds at least one specified epitope specific to at least one dual integrin protein, subunit, fragment, portion or any combination thereof. The at least one epitope can comprise at least one antibody binding region that comprises at least one portion of said protein, which epitope is preferably comprised of at least 1–5 amino acids of at least one portion of a dual integrin, such as but not limited to, (a) 29–48, 58–63, 69–79, 82–85, 88–134, 140–157, 161–183, 186–190, 192–198, 202–212, 215–217, 223–237, 240–244, 248–255, 259–268, 287–301, 313–322, 326–328, 332–344, 348–351, 354–365, 376–387, 393–401, 407–414, 417–419, 422–433, 443–451, 458–461, 465–469, 472, (b) 32–41, 46–47, 53–55, 58–69, 72–74, 77–79, 85–88, 91–94, 96–105, 110–113, 117–125, 129–142, 145–153, 155–159, 161–163, 166–170, 172–174, 184–197, 200–209, 215–218, 221–225, 184–197, 200–209, 215–218, 221–225, 227–250, 259–261, 263–267, 269–270, 275–281; and (c) 29–35, 43–45, 48–63, 67–69, 72–74, 80–82, 84–87, 95–105, 108–113, 117–142, 145–163, 166–170, 172–176, 184–186, 191–201, 204–206, 216–219, 224–226, 229–251, 260–262, 264–268, 276–282, 286–288, 294–299, 301–318, 323–325, 328–330, 338–342, 345–349, 353–358, of SEQ ID NO:9, 16, and 17, respectively thereof, or such as but not limited to, at least one functional, extracellular, soluble, hydrophillic, external or cytoplasmic domain of said dual integrin protein, subunit or any portion thereof.

The at least one antibody can optionally comprise at least one specified portion of at least one complementarity determining region (CDR) (e.g., CDR1, CDR2 or CDR3 of the heavy or light chain variable region) and/or at least one constant or variable framework region or any portion thereof. The at least one antibody amino acid sequence can further optionally comprise at least one specified substitution, insertion or deletion as described herein or as known in the art.

The present invention also provides at least one isolated anti-dual integrin antibody as described herein, wherein the antibody has at least one activity, such as, but not limited to inhibition of vitronectin binding, inhbition of binding of alpha-v beta-3 to at least one of an alpha-v beta3 ligand or receptor, inhbition of binding of alpha-v beta-5 to at least one of an alpha-v beta-5 ligand or receptor, angiogenesis modulation, binding to dual integrin or single integrin expressing cells. A(n) anti-dual integrin antibody can thus be screened for a corresponding activity according to known methods, such as but not limited to, at least one biological activity towards a dual integrin protein.

The present invention further provides at least one dual integrin anti-idiotype antibody to at least one dual integrin antibody of the present invention. The anti-idiotype antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that can be incorporated into an antibody of the present invention. An antibody of the invention can include or be derived from any mammal, such as but not limited to a human, a mouse, a rabbit, a rat, a rodent, a primate, and the like.

The present invention provides, in one aspect, isolated nucleic acid molecules comprising, complementary, or hybridizing to, a polynucleotide encoding at least one dual integrin anti-idiotype antibody, comprising at least one specified sequence, domain, portion or variant thereof. The present invention further provides recombinant vectors comprising said dual integrin anti-idiotype antibody encoding nucleic acid molecules, host cells containing such nucleic acids and/or recombinant vectors, as well as methods of making and/or using such anti-idiotype antiobody nucleic acids, vectors and/or host cells.

The present invention also provides at least one method for expressing at least one anti-dual integrin antibody, or dual integrin anti-idiotype antibody, in a host cell, comprising culturing a host cell as described herein under conditions wherein at least one anti-dual integrin antibody is expressed in detectable and/or recoverable amounts.

The present invention also provides at least one composition comprising (a) an isolated anti-dual integrin antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition.

The present invention further provides at least one anti-dual integrin antibody method or composition, for administering a therapeutically effective amount to modulate or treat at least one dual integrin related condition in a cell, tissue, organ, animal or patient and/or, prior to, subsequent to, or during a related condition, as known in the art and/or as described herein.

The present invention also provides at least one composition, device and/or method of delivery of a therapeutically or prophylactically effective amount of at least one anti-dual integrin antibody, according to the present invention.

The present invention further provides at least one anti-dual integrin antibody method or composition, for diagnosing at least one dual integrin related condition in a cell, tissue, organ, animal or patient and/or, prior to, subsequent to, or during a related condition, as known in the art and/or as described herein.

The present invention also provides at least one composition, device and/or method of delivery for diagnosing of at least one anti-dual integrin antibody, according to the present invention.

DESCRIPTION OF THE FIGURES

FIG. 3 shows a graph of cell adhesion where MDAMB435L2 cells were harvested and pre-incubated with various concentrations of GenO95 for 10 minutes. Tumor cells were then added to vitronectin coated Linbro plates and incubated at 37° C. for one hour. Wells were washed three times and the MTT based Cell Titer AQ dye was added to each well. Cell adhesion was determined in an ELISA plate reader where OD490 nm is directly proportional to cell adhesion. Cell adhesion to BSA coated wells served as negative control (data not shown). Each data point is the mean of triplicate determinations.

FIG. 7A–C shows saturation binding curves with graphs binding to (FIG. 7A): A375S2; (FIG. 7B): HT-29; (FIG. 7C): M21. Cells were plated 2 days prior to experiment, and 1×10$^5$ cells/well at the time of study. 125-I GenO.95 (1 μCi/μg) was added in 1% growth media and incubated on cells for 1.5 h, 37° C. Nonspecific binding was determined using 100× cold mAb in media. Cells were washed 3× and counted for bound radioactivity. Each curve represents 4–5 separate studies, and each data point in an experiment was the mean of triplicate samples.

(FIG. 8B): HT-29; (FIG. 8C): M21. Cells were plated 2 days prior to the experiment, and 1×10$^5$ cells/well at the time of study. 125-I ReoPro (1 μCi/μg) was added in 1% growth media and incubated on cells for 1.5 h, 37° C. Nonspecific binding was determined using 100× cold mAb in media. Cells were washed 3× and counted for bound radioactivity. Each curve represents 4–5 separate studies, and each data point in an experiment was the mean of triplicate samples.

FIG. 11 shows a graph of quantification of capillary formation in a fibrin gel in complete media. The number of microcapillary sprouts were quantified as described in Methods of Example 4. Control indicates vehicle control. Mouse (m) and human (h)-IgG served as negative controls. LM-P1F6 is a combination of both LM609 and P1F6. Each bar represents the mean of 6 wells (+/−SD).

In FIG. 13, the extent of cell adhesion in the presence of various concentrations of antibody was plotted as a percent of cell adhesion in the absence of antibody that was considered as 100%. Each data point is the mean of triplicate determinations (+/−SD).

In FIG. 14 the extent of cell adhesion in the presence of various concentrations of antibody was plotted as a percent of cell adhesion in the absence of antibody that was considered as 100%. Each data point is the mean of triplicate determinations (+/−SD).

FIG. 15. Adhesion of human colon carcinoma HT29 cells to vitronectin. The adhesion assay was performed as described in Methods. Cell adhesion to BSA coated wells served as a negative control. Data in FIG. 15 are plotted as percent of maximum binding (absence of antibody), and are the mean of triplicate determinations (+/−SD).

FIG. 16A–D. Migration of HUVECS toward 2 μg/ml vitronectin. The assay was performed as described in Methods and cells were allowed to migrate for 6 h. Photomicrographs are representative fields (10× objective lens) of cell migration in FIG. 16A, absence of antibody, (16B), Gen095 (5 μg/ml), (16C), GenO95 (40 μg/ml). FIG. 16D is graphical representation of cell migration in the presence of varying concentrations of GenO95. The data were normalized to percent of control (no antibody) which was considered as 100%, and each point is the mean of three transwell filters (+/−SD).

FIG. 18(A) is a graphical representation of cell migration in the presence of LM609, P1F6, combination of LM609+P1F6, isotype matched control antibodies (human and mouse). The antibodies and proteins were used at a concentration of 10 μg/ml. FIG. 18(B) is a graphical representation of cell migration in the presence of ReoPro and GenO95. Photomicrographs are representative fields (10× objective lens) of cell migration in FIG. 18(C), the absence of antibody, FIG. 18(D), GenO95 (5 μg/ml), and FIG. 18(E), GenO95 (20 μg/ml). The data were normalized to percent of control (no antibody) which was considered as 100%, and each point is the mean of three transwell filters (+/−SD).

FIG. 19(A) is a graphical representation of cell migration in the presence of varying concentrations of GenO95. FIG. 19(B) is a graphical representation of cell migration in the presence of LM609, P1F6, combination of LM609+P1F6, isotype matched control antibodies (human and mouse). The data were normalized to percent of control, which was considered as 100%, and each point is the mean of three transwell filters (+/−SD). Photomicro-graphs are representative fields (10× objective lens) of cell migration in FIG. 19(C), absence of antibody, FIG. 19(D), Gen095 (5 μg/ml), and FIG. 19(E), Gen095 (20 μg/ml).

FIG. 20A–E. Migration of HUVECS towards vitronectin in the presence of bFGF. The undersides of migration chamber filters were coated with 2 μg/ml vitronectin, and the assay was performed as described in Methods. Cells were allowed to migrate for 6 h. In FIG. 20A–E, each data point is the mean of 3 transwell filters (+/−SD). FIG. 20(A), bFGF; FIG. 20(B), Gen095 (5 µg/ml); FIG. 20(C), Gen095 (40 µg/ml); FIG. 20(D), no-bFGF. FIG. 20(E), Inhibition of cell migration in the presence of various antibodies is shown graphically.

FIG. 21(D): The concentration of all antibodies and proteins is 10 µg/ml. The data were normalized to percent of control (no antibody) which was considered as 100%, and each point is the mean of three transwell filters (+/−SD).

DESCRIPTION OF THE INVENTION

Figure 1:
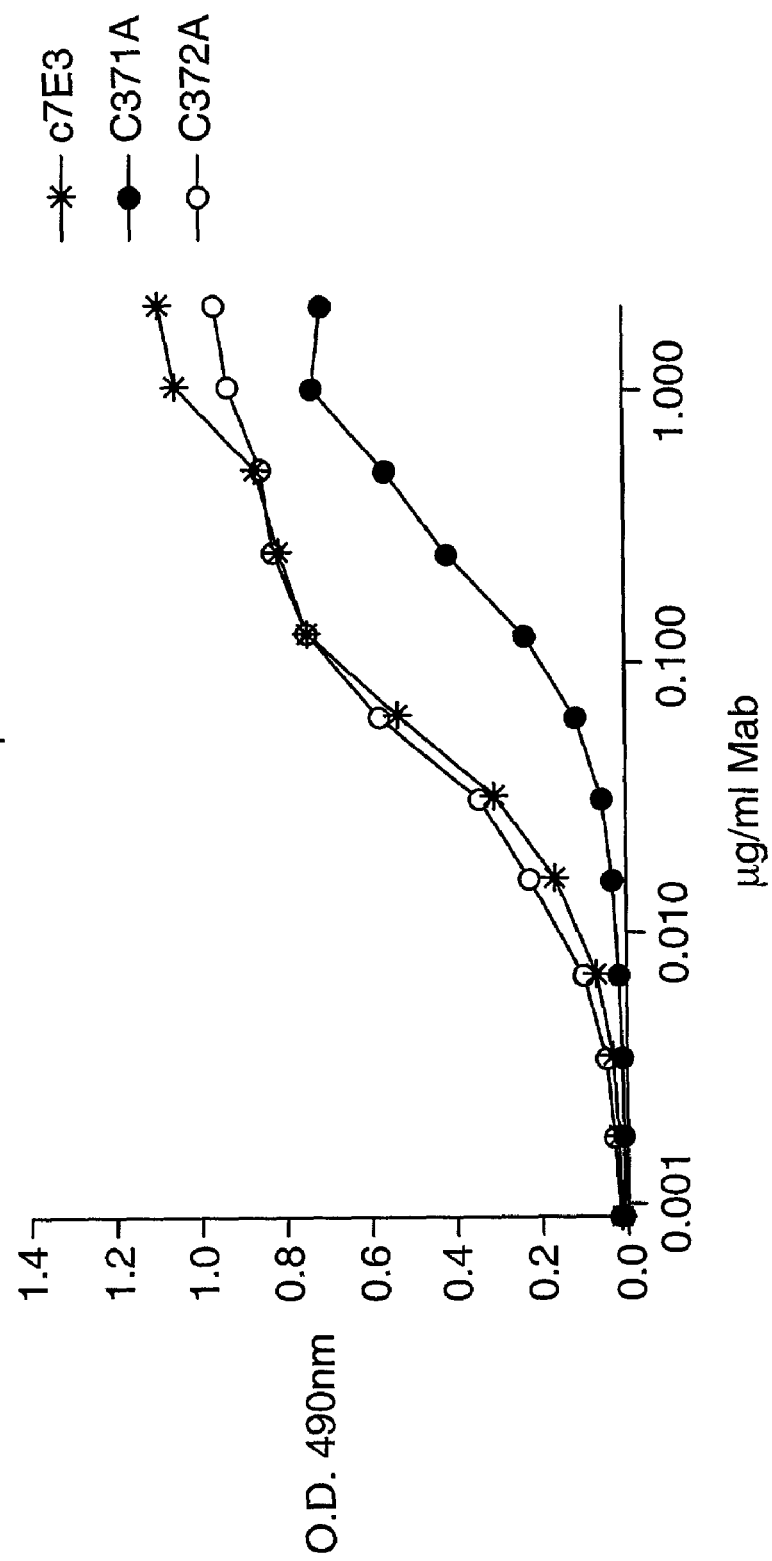
FIG. 1 shows a graph of doubling dilutions of anti-$\alpha V \beta 3$ Mabs were incubated on $\alpha V \beta 3$ coated plates for 1 hour at RT. Plates were washed twice and probed with HRP labeled goat anti-human IgG kappa specific antibody for 1 hour at RT. Plates were again washed, developed with OPD substrate and OD's measured at 490 nm.

The present invention provides isolated, recombinant and/or synthetic anti-dual integrin human, primate, rodent, mammalian, chimeric, humanized or CDR-grafted, antibodies and dual integrin anti-idiotype antibodies thereto, as well as compositions and encoding nucleic acid molecules comprising at least one polynucleotide encoding at least one anti-dual integrin antibody or anti-idiotype antibody. The present invention further includes, but is not limited to, methods of making and using such nucleic acids and antibodies and anti-idiotype antibodies, including diagnostic and therapeutic compositions, methods and devices.

As used herein, an "anti-alpha-v-beta3, alpha-v-beta5 dual integrin antibody," "anti-dual integrin antibody," "anti-dual integrin antibody portion," or "anti-dual integrin antibody fragment" and/or "anti-dual integrin antibody variant" and the like include any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, or at least one portion of an dual integrin receptor or binding protein, which can be incorporated into an antibody of the present invention. Such antibody optionally further affects a specific ligand, such as but not limited to where such antibody modulates, decreases, increases, antagonizes, angonizes, mitigates, aleviates, blocks, inhibits, abrogates and/or interferes with at least one dual integrin activity or binding, or with dual integrin receptor activity or binding, in vitro, in situ and/or in vivo. As a non-limiting example, a suitable anti-dual integrin antibody, specified portion or variant of the present invention can bind at least one dual integrin, or specified portions, variants or domains thereof. A suitable anti-dual integrin antibody, specified portion, or variant can also optionally affect at least one of dual integrin activity or function, such as but not limited to, RNA, DNA or protein synthesis, dual integrin release, dual integrin receptor signaling, membrane dual integrin cleavage, dual integrin activity, dual integrin production and/or synthesis. The term "antibody" is further intended to encompass antibodies, digestion fragments, specified portions and variants thereof, including antibody mimetics or comprising portions of antibodies that mimic the structure and/or function of an anitbody or specified fragment or portion thereof, including single chain antibodies and fragments thereof. Functional fragments include antigen-binding fragments that bind to a mammalian dual integrin. For example, antibody fragments capable of binding to dual integrin or portions thereof, including, but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH$_1$ domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. Similarly, antibodies designated primate (monkey, babboon, chimpanzee, etc.), rodent (mouse, rat, rabbit, guinea pid, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably human or humanized, antibodies that have binding specificities for at least two different antigens. In the present case, one of the binding specificities is for at least one dual integrin protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos., 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-dual integrin antibodies (also termed dual integrin antibodies) useful in the methods and compositions of the present invention can optionally be characterized by high affinity binding to dual integrin and optionally and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344:1125–1127 (1994), entirely incorporated herein by reference).

Utility

The isolated nucleic acids of the present invention can be used for production of at least one anti-dual integrin antibody or specified variant thereof, which can be used to measure or effect in an cell, tissue, organ or animal (including mammals and humans), to diagnose, monitor, modulate, treat, alleviate, help prevent the incidence of, or reduce the symptoms of, at least one dual integrin condition, selected from, but not limited to, at least one of an immune disorder or disease, a cardiovascular disorder or disease, an infectious, malignant, and/or neurologic disorder or disease, or other known or specified dual integrin related condition.

Such a method can comprise administering an effective amount of a composition or a pharmaceutical composition comprising at least one anti-dual integrin antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01–5000 µg/ml serum concentration per single, multiple, or continuous adminstration, or any effective range or value therein, as done and determined using known methods, as described herein or known in the relevant arts.

Citations

All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference:

Ausubel, et al., ed., Current Protocols in Molecular Biology, John Wiley & Sons, Inc., NY, N.Y. (1987–2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994–2001); Colligan et al., Current Protocols in Protein Science, John Wiley & Sons, NY, N.Y., (1997–2001).

Antibodies of the Present Invention

At least one anti-dual integrin antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987–2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994–2001); Colligan et al., Current Protocols in Protein Science, John Wiley & Sons, NY, N.Y., (1997–2001), each entirely incorporated herein by reference.

Human antibodies that are specific for human dual integrin proteins or fragments thereof can be raised against an appropriate immunogenic antigen, such as isolated and/or dual integrin protein or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybnrdoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromylomas, fusion products thereof, or any cell or fusion cell derived therefrom, or any other suitable cell line as known in the art. See, e.g., www.atcc.org, www.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350, 260 (May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); EP 614 989 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901–907 (1997); Sandhu et al., Crit. Rev. Biotechnol. 16:95–118 (1996); Eren et al., Immunol. 93:154–161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937–4942 (May 1997); Hanes et al., Proc. Natl. Acad. Sci. USA, 95:14130–14135 (November 1998)); single cell antibody producing technologies (e.g., selected lymphocyte antibody method ("SLAM") (U.S. Pat. No. 5,627,052, Wen et al., J. Immunol. 17:887–892 (1987); Babcook et al., Proc. Natl. Acad. Sci. USA 93:7843–7848 (1996)); gel microdroplet and flow cytometry (Powell et al., Biotechnol. 8:333–337 (1990); One Cell Systems, Cambridge, Mass.; Gray et al., J. Imm. Meth. 182:155–163 (1995); Kenny et al., Bio/Technol. 13:787–790 (1995)); B-cell selection (Steenbakkers et al., Molec. Biol. Reports 19:125–134 (1994); Jonak et al., Progress Biotech, Vol. 5, In Vitro Immunization in Hybridoma Technology, Borrebaeck, ed., Elsevier Science Publishers B. V., Amsterdam, Netherlands (1988)).

Methods for engineering or humanizing non-human or human antibodies can also be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., in a number of public databases such as the NCBI database of the National Institute of Health or publications such as Kabat et al., Sequences of Proteins of Immunological Interest, U.S. Dept. Health (1983).

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos: 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

The anti-dual integrin antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-dual integrin antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos: 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856–859 (1994), Taylor et al., *Int. Immunol.* 6(4)579–591 (1994), Green et al, *Nature Genetics* 7:13–21

(1994), Mendez et al., *Nature Genetics* 15:146–156 (1997), Taylor et al., *Nucleic Acids Research* 20(23):6287–6295 (1992), Tuaillon et al., *Proc Natl Acad Sci USA* 90(8) 3720–3724 (1993), Lonberg et al., *Int Rev Immunol* 13(1): 65–93 (1995) and Fishwald et al., *Nat Biotechnol* 14(7): 845–851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. antibody screening of peptide display libraries is well known in the art. The displayed peptide sequences can be from 3 to 5000 or more amino acids in length, frequently from 5–100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. Nos. 5,885,793, assigned to Cambridge antibody Technologies; 5,750,373, assigned to Genentech, U.S. Pat. Nos. 5,618,920, 5,595,898, 5,576,195, 5,698,435, 5,693,493, 5,698,417, assigned to Xoma, Colligan, supra; Ausubel, supra; or Sambrook, supra, each of the above patents and publications entirely incorporated herein by reference.

Antibodies of the present invention can also be prepared using at least one anti-dual integrin antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Antibodies of the present invention can additionally be prepared using at least one anti-dual integrin antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95–118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127–147 (1999) and references cited therein. antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101–109 (1998) and reference cited therein. Thus, antibodies of the present invention can also be produced using transgenic plants, according to know methods. See also, e.g., Fischer et al., Biotechnol. Appl. Biochem. 30:99–108 (October, 1999), Ma et al., Trends Biotechnol. 13:522–7 (1995); Ma et al., Plant Physiol. 109:341–6 (1995); Whitelam et al., Biochem. Soc. Trans. 22:940–944 (1994); and references cited therein. See, also generally for plant expression of antibodies, but not limited to, Each of the above references is entirely incorporated herein by reference.

The antibodies of the invention can bind human dual integrin with a wide range of affinities ($K_D$). In a preferred embodiment, at least one human mAb of the present invention can optionally bind human dual integrin with high affinity. For example, a human mAb can bind human dual integrin with a $K_D$ equal to or less than about $10^{-7}$ M, such as but not limited to, 0.1–9.9 (or any range or value therein) X $10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules

Using the information provided herein, such as the nucleotide sequences encoding at least 70–100% of the contiguous amino acids of at least one of SEQ ID NOS:1, 2, 3, 4, 5, 6, 7, 8, specified fragments, variants or consensus sequences thereof, or a deposited vector comprising at least one of these sequences, a nucleic acid molecule of the present invention encoding at least one anti-dual integrin antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NOS:1–3) or light chain (e.g., SEQ ID NOS: 4–6); nucleic acid molecules comprising the coding sequence for an anti-dual integrin antibody or variable region (e.g., SEQ ID NOS:7,8); and nucleic acid molecules which comprise a nucleotide sequence substantially different from those described above but which, due to the degeneracy of the genetic code, still encode at least one anti-dual integrin antibody as described herein and/or as known in the art. Of course, the genetic code is well known in the art. Thus, it would be routine for one skilled in the art to generate such degenerate nucleic acid variants that code for specific anti-dual integrin antibodies of the present invention. See, e.g., Ausubel, et al., supra, and such nucleic acid variants are included in the present invention. Non-limiting examples of isolated nucleic acid molecules of the present inveniton include SEQ ID NOS:10, 11, 12, 13, 14, 15, corresponding to non-limiting examples of a nucleic acid encoding, respectively, HC CDR1, HC CDR2, HC CDR3, LC CDR1, LC CDR2, LC CDR3, HC variable region and LC variable region.

In another aspect, the invention provides isolated nucleic acid molecules encoding a(n) anti-dual integrin antibody having an amino acid sequence as encoded by the nucleic acid contained in the plasmid designated clone C371A.

As indicated herein, nucleic acid molecules of the present invention which comprise a nucleic acid encoding an anti-dual integrin antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Which Selectively Hybridize to a Polynucleotide as Described Herein The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70–100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and U.S. Pat. Nos. 4,921,794 to Tabor, et al; U.S. Pat. Nos. 5,142,033 to Innis; U.S. Pat. Nos. 5,122,464 to Wilson, et al.; U.S. Pat. Nos. 5,091,310 to Innis; U.S. Pat. Nos. 5,066,584 to Gyllensten, et al; U.S. Pat. Nos. 4,889,818 to Gelfand, et al; U.S. Pat. Nos. 4,994,370 to Silver, et al; U.S. Pat. Nos. 4,766,067 to Biswas; U.S. Pat. Nos. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors And Host Cells

The present invention also relates to vectors that include isolated nucleic acid molecules of the present invention, host cells that are genetically engineered with the recombinant vectors, and the production of at least one anti-dual integrin antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1–4 and 16–18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29–17.42 and 18.1–18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773–781 (1983)). Additionally, gene sequences to control replication in the host cell can be incorporated into the vector, as known in the art.

Purification of an Antibody

An anti-dual integrin antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997–2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37–17.42; Ausubel, supra, Chapters 10, 12, 13, 16, 18 and 20, Colligan, Protein Science, supra, Chapters 12–14, all entirely incorporated herein by reference.

Anti-Dual Integrin Antibodies

The isolated antibodies of the present invention comprise an antibody amino acid sequences disclosed herein encoded by any suitable polynucleotide, or any isolated or prepared antibody. Preferably, the human antibody or antigen-binding fragment binds human dual integrin and, thereby partially or substantially neutralizes at least one biological activity of the protein. An antibody, or specified portion or variant thereof, that partially or preferably substantially neutralizes at least one biological activity of at least one dual integrin protein or fragment can bind the protein or fragment and thereby inhibit activitys mediated through the binding of dual integrin to the dual integrin receptor or through other dual integrin-dependent or mediated mechanisms. As used herein, the term "neutralizing antibody" refers to an antibody that can inhibit an dual integrin-dependent activity by about 20–120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-dual integrin antibody to inhibit an dual integrin-dependent activity is preferably assessed by at least one suitable dual integrin protein or receptor assay, as described herein and/or as known in the art. A human antibody of the invention can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4. Antibodies of this type can be prepared by employing a transgenic mouse or other trangenic non-human mammal comprising at least one human light chain (e.g., IgG, IgA and IgM (e.g., γ1, γ2, γ3, γ4) transgenes as described herein and/or as known in the art. In another embodiment, the anti-human dual integrin human antibody comprises an IgG1 heavy chain and a IgG1 light chain.

At least one antibody of the invention binds at least one specified epitope specific to at least one dual integrin protein, subunit, fragment, portion or any combination thereof. The at least one epitope can comprise at least one antibody binding region that comprises at least one portion of said protein, which epitope is preferably comprised of at least one extracellular, soluble, hydrophillic, external or cytoplasmic portion of said protein. The at least one specified epitope can comprise any combination of at least one amino acid sequence of at least 1–3 amino acids to the entire specified portion of contiguous amino acids of the SEQ ID NOS:9, 16 or 17.

Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. As a non-limiting example, the antibody or antigen-binding portion or variant can comprise at least one of the heavy chain CDR3 having the amino acid sequence of SEQ ID NO:3, and/or a light chain CDR3 having the amino acid sequence of SEQ ID NO:6. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs1, 2 and/or 3 (e.g., SEQ ID NOS: 1, 2, and/or 3). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (e.g., SEQ ID NOS: 4, 5, and/or 6). In a preferred embodiment the three heavy chain CDRs and the three light chain CDRs of the anitbody or antigen-binding fragment have the amino acid sequence of the corresponding CDR of at least one of mAb Gen095, Gen0101, CNTO 95, C372A, as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-dual integrin antibody can comprise at least one of a heavy or light chain variable region having a defined amino acid sequence. For example, in a preferred embodiment, the anti-dual integrin antibody comprises at least one of at least one heavy chain variable region, optionally having the amino acid sequence of SEQ ID NO:7 and/or at least one light chain variable region, optionally having the amino acid sequence of SEQ ID NO:8. antibodies that bind to human dual integrin and that comprise a defined heavy or light chain variable region can be prepared using suitable methods, such as phage display (Katsube, Y., et al., *Int J Mol. Med*, 1(5):863–868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human dual integrin or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human dual integrin with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g, charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up anti-dual integrin antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
| --- | --- | --- | --- |
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |

-continued

| SINGLE LETTER CODE | THREE LETTER CODE | NAME | THREE NUCLEOTIDE CODON(S) |
|---|---|---|---|
| W | Trp | Tryptophan | UGG |
| Y | Tyr | Tyrosine | UAC, UAU |

An anti-dual integrin antibody of the present invention can include one or more amino acid substitutions, deletions or additions, either from natural mutations or human manipulation, as specified herein.

Of course, the number of amino acid substitutions a skilled artisan would make depends on many factors, including those described above. Generally speaking, the number of amino acid substitutions, insertions or deletions for any given anti-dual integrin antibody will not be more than 40, 30, 20, 19, 18, 17, 16, 15, 14, 13, 12, 11, 10, 9, 8, 7, 6, 5, 4, 3, 2, 1, such as 1–30 or any range or value therein, as specified herein.

Amino acids in an anti-dual integrin antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081–1085 (1989)). The latter procedure introduces single alanine mutations at every residue in the molecule. The resulting mutant molecules are then tested for biological activity, such as, but not limited to at least one dual integrin neutralizing activity. Sites that are critical for antibody binding can also be identified by structural analysis such as crystallization, nuclear magnetic resonance or photoaffinity labeling (Smith, et al., J. Mol. Biol. 224:899–904 (1992) and de Vos, et al., Science 255:306–312 (1992)).

Anti-dual integrin antibodies of the present invention can include, but are not limited to, at least one portion, sequence or combination selected from 5 to all of the contiguous amino acids of at least one of SEQ ID NOS:1, 2, 3, 4, 5, 6.

A(n) anti-dual integrin antibody can further optionally comprise a polypeptide of at least one of 70–100% of the contiguous amino acids of at least one of SEQ ID NOS:7, 8.

In one embodiment, the amino acid sequence of an immunoglobulin chain, or portion thereof (e.g., variable region, CDR) has about 70–100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of SEQ ID NOS:7, 8. For example, the amino acid sequence of a light chain variable region can be compared with the sequence of SEQ ID NO:8, or the amino acid sequence of a heavy chain CDR3 can be compared with SEQ ID NO:7. Preferably, 70–100% amino acid identity (i.e., 90, 91, 92, 93, 94, 95, 96, 97, 98, 99, 100 or any range or value therein) is determined using a suitable computer algorithm, as known in the art.

Exemplary heavy chain and light chain variable regions sequences are provided in SEQ ID NOS: 7, 8. The antibodies of the present invention, or specified variants thereof, can comprise any number of contiguous amino acid residues from an antibody of the present invention, wherein that number is selected from the group of integers consisting of from 10–100% of the number of contiguous residues in an anti-dual integrin antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%–1000% of that of the native (non-synthetic), endogenous or related and known antibody. Methods of assaying and quantifying measures of enzymatic activity and substrate specificity, are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include monoesters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —(CH$_2$)$_3$—, —NH—(CH$_2$)$_6$—NH—, —(CH$_2$)$_2$—NH— and —CH$_2$—O—CH$_2$—CH$_2$—O—CH$_2$—CH$_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodjimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147–153 (1992); Werlen et al., *Bioconjugate Chem.*, 5:411–417 (1994); Kumaran et al., *Protein Sci.* 6(10):2233–2241 (1997); Itoh et al., *Bioorg. Chem.*, 24(1): 59–68 (1996); Capellas et al., *Biotechnol. Bioeng.*, 56(4): 456–463 (1997)), and the methods described in Hermanson, G. T., *Bioconjugate Techniques*, Academic Press: San Diego, Calif. (1996).

Anti-Idiotype Antibodies to Anti-Dual Integrin Antibody Compositions

In addition to monoclonal or chimeric anti-dual integrin antibodies, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g. mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Anti-Dual Integrin Antibody Compositions

The present invention also provides at least one anti-dual integrin antibody composition comprising at least one, at least two, at least three, at least four, at least five, at least six or more anti-dual integrin antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-dual integrin antibody amino acid sequence selected from the group consisting of 70–100% of the contiguous amino acids of SEQ ID NOS:1, 2, 3, 4, 5, 6, 7, 8, or specified fragments, domains or variants thereof. Preferred anti-dual integrin antibody compositions include at least one or two full length, fragments, domains or variants as at least one CDR or LBR containing portions of the anti-dual integrin antibody sequence of 70–100% of SEQ ID NOS:1, 2, 3, 4, 5, 6, or specified fragments, domains or variants thereof. Further preferred compositions comprise 40–99% of at least one of 70–100% of SEQ ID NOS:1, 2, 3, 4, 5, 6, or specified fragments, domains or variants thereof. Such composition percentages are by weight, volume, concentration, molarity, or molality as liquid or dry solutions, mixtures, suspension, emulsions or colloids, as known in the art or as described herein.

Anti-dual integrin antibody compositions of the present invention can further comprise at least one of any suitable and effective amount of a composition or pharmaceutical composition comprising at least one anti-dual integrin antibody to a cell, tissue, organ, animal or patient in need of such modulation, treatment or therapy, optionally further comprising at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist or antibody. Non-limiting examples of such cytokines include, but are not limted to, any of IL-1 to IL-23, IL-6, anti-tumor antibodies, chemotherapeutic agents or radiation therapies. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), *Staphylococcal* enterotoxin A (SEA), B (SEB), or C (SEC), *Streptococcal* enterotoxins and the like. Such bacteria include, but are not limited to, strains of a species of enterotoxigenic *E. coli* (ETEC), enterohemorrhagic *E. coli* (e.g., strains of serotype 0157: H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholera-suis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa,* and *Streptococci*. See, e.g., Stein, ed., INTERNAL MEDICINE, 3rd ed., pp 1–13, Little, Brown and Co., Boston, (1990); Evans et al., eds., Bacterial Infections of Humans: Epidemiology and Control, 2d. Ed., pp 239–254, Plenum Medical Book Co., New York (1991); Mandell et al, Principles and Practice of Infectious Diseases, 3d. Ed., Churchill Livingstone, N.Y. (1990); Berkow et al, eds., *The Merck Manual,* 16th edition, Merck and Co., Rahway, N.J., 1992; Wood et al, FEMS Microbiology Immunology, 76:121–134 (1991); Marrack et al, Science, 248:705–711 (1990), the contents of which references are incorporated entirely herein by reference.

Anti-dual integrin antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* $18^{th}$ Edition, Mack Publishing Co. (Easton, Pa.) 1990. Pharmaceutically acceptable carriers can be routinely selected that are suitable for the mode of administration, solubility and/or stability of the anti-dual integrin antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1–99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-dual integrin antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, anti-dual integrin antibody compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-dual integrin antibody, portion or variant compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferrred carrier or excipient materials are carbohydrates (e.g., saccharides and alditols) and buffers (e.g., citrate) or polymeric agents.

Formulations

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one anti-dual integrin antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001–5%, or any range or value therein, such as, but not limited to 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1–2% m-cresol (e.g., 0.2, 0.3. 0.4, 0.5, 0.9, 1.0%), 0.1–3% benzyl alcohol (e.g., 0.5, 0.9, 1.1., 1.5, 1.9, 2.0, 2.5%), 0.001–0.5% thimerosal (e.g., 0.005, 0.01), 0.001–2.0% phenol (e.g., 0.05, 0.25, 0.28, 0.5, 0.9, 1.0%), 0.0005–1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-dual integrin antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-dual integrin antibody, and a second vial comprising an aqueous diluent of prescribed buffer or preservative, wherein said packaging material comprises a label that instructs a patient to reconstitute the at least one anti-dual integrin antibody in the aqueous diluent to form a solution that can be held over a period of twenty-four hours or greater.

The at least one anti-dual integrinantibody used in accordance with the present invention can be produced by recombinant means, including from mammalian cell or transgenic preparations, or can be purified from other biological sources, as described herein or as known in the art.

The range of at least one anti-dual integrin antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-dual integrin antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-dual integrin antibody and preservative in an aqueous diluent is carried out using conventional dissolution and mixing procedures. To prepare a suitable formulation, for example, a measured amount of at least one anti-dual integrin antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-dual integrin antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1–12 months, one-half, one and a half, and/or two years.

The solutions of at least one anti-dual integrin antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-dual integrin antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-dual integrin antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject® NovoPen®, B-D®Pen, AutoPen®, and OptiPen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com). Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one anti-dual integrin antibody in the aqueous diluent to form a solution and to use the solution over a period of 2–24 hours or greater for the two vial, wet/dry, product. For the single vial, solution product, the label indicates that such solution can be used over a period of 2–24 hours or greater. The presently claimed products are useful for human pharmaceutical product use.

The formulations of the present invention can be prepared by a process that comprises mixing at least one anti-dual integrin antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-dual integrin antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one anti-dual integrin antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating at least one dual integrin related disease, in a cell, tissue, organ, animal, or patient, as known in the art or as described herein, using at least one dual integrin antibody of the present invention.

The present invention also provides a method for modulating or treating at least one dual integrin related disease, in a cell, tissue, organ, animal, or patient including, but not limited to, at least one of obesity, an immune related disease, a cardiovascular disease, an infectious disease, a malignant disease or a neurologic disease.

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), chronic salicylate intoxication, and the like. See, e.g., the Merck Manual, 12th–17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one anti-dual integrin antibody to a cell, tissue, organ, animal or patient in need of such modulation, treatment or therapy.

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A,B or C, or the like), septic arthritis, peritonitis, pneumonia, epiglottitis, e. coli 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, mycobacterium tuberculosis, mycobacterium avium intracellulare, pneumocystis carinii pneumonia, pelvic inflammatory disease, orchitis/epidydimitis, legionella, lyme disease, influenza a, epstein-barr virus, vital-associated hemaphagocytic syndrome, vital encephalitis/aseptic meningitis, and the like;

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

The present invention also provides a method for modulating or treating at least one neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16$^{th}$ Edition, Merck & Company, Rahway, N.J. (1992)

Any method of the present invention can comprise administering an effective amount of a composition or pharmaceutical composition comprising at least one anti-dual integrin antibody to a cell, tissue, organ, animal or patient in need of such modulation, treatment or therapy. Such a method can optionally further comprise co-administration or combination therapy for treating such immune diseases, wherein the administering of said at least one anti-dual integrin antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a syrnpathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, 2$^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

TNF antagonists suitable for compositions, combination therapy, co-administration, devices and/or methods of the present invention (further comprising at least one anti body, specified portion and variant thereof, of the present invention), include, but are not limited to, anti-TNF antibodies, antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNFα antibody," or fragment and the like decreases, blocks, inhibits, abrogates or interferes with TNFα activity in vitro, in situ and/or preferably in vivo. For example, a suitable TNF human antibody of the present invention can bind TNFα and includes anti-TNF antibodies, antigen-binding fragments thereof, and specified mutants or domains thereof that bind specifically to TNFα. A suitable TNF anttibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

Chimeric antibody cA2 consists of the antigen binding variable region of the high-affinity neutralizing mouse anti-human TNFα IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric antibody cA2 is derived from the variable region of the murine antibody A2. In a particular embodiment, a preferred source for nucleic acids encoding the variable region of the murine antibody A2 is the A2 hybridoma cell line.

Chimeric A2 (cA2) neutralizes the cytotoxic effect of both natural and recombinant human TNFα in a dose dependent manner. From binding assays of chimeric antibody cA2 and recombinant human TNFα, the affinity constant of chimeric antibody cA2 was calculated to be $1.04 \times 10^{10} M^{-1}$. Preferred methods for determining monoclonal antibody specificity and affinity by competitive inhibition can be found in Harlow, et al., *antibodies: A Laboratory Manual,* Cold Spring Harbor Laboratory Press, Cold Spring Harbor, N.Y. 1988; Colligan et al., eds., *Current Protocols in Immunology,* Greene Publishing Assoc. and Wiley Interscience, New York, (1992–2000); Kozbor et al., *Immunol, Today,* 4:72–79 (1983); Ausubel et al., eds. *Current Protocols in Molecular Biology,* Wiley Interscience, New York (1987–2000); and Muller, *Meth. Enzymol.,* 92:589–601 (1983), which references are entirely incorporated herein by reference.

In a particular embodiment, murine monoclonal antibody A2 is produced by a cell line designated c134A. Chimeric antibody cA2 is produced by a cell line designated c168A.

Additional examples of monoclonal anti-TNF antibodies that can be used in the present invention are described in the art (see, e.g., U.S. Pat. No. 5,231,024; Möller, A. et al., *Cytokine* 2(3):162–169 (1990); U.S. application Ser. No. 07/943,852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., *Biochem. Biophys. Res. Comm.* 137:847–854 (1986); Meager, et al., *Hybridoma* 6:305–311 (1987); Fendly et al., *Hybridoma* 6:359–369 (1987); Bringman, et al., *Hybridoma* 6:489–507 (1987); and Hirai, et al., *J. Immunol. Meth.* 96:57–62 (1987), which references are entirely incorporated herein by reference).

TNF Receptor Molecules

Preferred TNF receptor molecules useful in the present invention are those that bind TNFα with high affinity (see, e.g., Feldmann et al., International Publication No. WO 92/07076 (published Apr. 30, 1992); Schall et al., *Cell* 61:361–370 (1990); and Loetscher et al., *Cell* 61:351–359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J. Biochem.* 223:831–840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., *J. Biol. Chem.* 265:1531–1536 (1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high affinity, as well as other undefined properties, can contribute to the therapeutic results achieved.

TNF receptor multimeric molecules useful in the present invention comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883–2886 (1991); Ashkenazi et al., *Proc. Natl. Acad. Sci. USA* 88:10535–10539 (1991); Peppel et al., *J. Exp. Med.* 174:1483–1489 (1991); Kolls et al., *Proc. Natl. Acad. Sci. USA* 91:215–219 (1994); Butler et al., *Cytokine* 6(6):616–623 (1994); Baker et al., *Eur. J. Immunol.* 24:2040–2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116,964; Capon et al., U.S. Pat. No. 5,225,538; and Capon et al., *Nature* 337:525–531 (1989), which references are entirely incorporated herein by reference.

A functional equivalent, derivative, fragment or region of TNF receptor molecule refers to the portion of the TNF receptor molecule, or the portion of the TNF receptor molecule sequence which encodes TNF receptor molecule, that is of sufficient size and sequences to functionally resemble TNF receptor molecules that can be used in the present invention (e.g., bind TNFα with high affinity and possess low immunogenicity). A functional equivalent of TNF receptor molecule also includes modified TNF receptor molecules that functionally resemble TNF receptor molecules that can be used in the present invention (e.g., bind TNFα with high affinity and possess low immunogenicity). For example, a functional equivalent of TNF receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology,* Greene Publishing Assoc. and Wiley-Interscience, New York (1987–2000).

Cytokines include any known cytokine. See, e.g., CopewithCytokines.com. Cytokine antagonists include, but are not limited to, any antibody, fragment or mimetic, any soluble receptor, fragment or mimetic, any small molecule antagonist, or any combination thereof.

Therapeutic Treatments. Any method of the present invention can comprise a method for treating a dual integrin mediated disorder, comprising administering an effective amount of a composition or pharmaceutical composition comprising at least one anti-dual integrin antibody to a cell, tissue, organ, animal or patient in need of such modulation, treatment or therapy. Such a method can optionally further comprise co-administration or combination therapy for treating such immune diseases, wherein the administering of said at least one anti-dual integrin antibody, specified portion or variant thereof, further comprises administering, before concurrently, and/or after, at least one selected from at least one at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, dacliuzumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist.

Typically, treatment of pathologic conditions is effected by administering an effective amount or dosage of at least one anti-dual integrin antibody composition that total, on average, a range from at least about 0.01 to 500 milligrams of at least one anti-dual integrinantibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1–5000 µg/ml serum concentration per single or multiple adminstration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100–500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5,16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5–99.999% by weight based on the total weight of the composition.

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1–10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes of can be used according to the present invention for administering pharmaceutically effective amounts of at least one anti-dual integrin antibody according to the present invention. While pulmonary administration is used in the following description, other modes of administration can be used according to the present invention with suitable results.

dual integrin antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aquous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semi-synthtetic mono- or di- or tri-glycerids. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery

The invention further relates to the administration of at least one anti-dual integrin antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one anti-dual integrin antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59–90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration

For pulmonary administration, preferably at least one anti-dual integrin antibody composition is delivered in a particle size effective for reaching the lower airways of the lung or sinuses. According to the invention, at least one anti-dual integrin antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458, 135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404, 871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one anti-dual integrin antibody is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 µm, preferably about 1–5 µm, for good respirability.

Administration of Dual Integrin Antibody Compositions as a Spray

A spray including dual integrin antibody composition protein can be produced by forcing a suspension or solution of at least one anti-dual integrin antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-dual integrin antibody composition protein delivered by a sprayer have a particle size less than about 10 µm, preferably in the range of about 1 µm to about 5 µm, and most preferably about 2 µm to about 3 µm.

Formulations of at least one anti-dual integrin antibody composition protein suitable for use with a sprayer typically include antibody composition protein in an aqueous solution at a concentration of about 0. 1 mg to about 100 mg of at least one anti-dual integrin antibody composition protein per ml of solution or mg/gm, or any range or value therein, e.g., but not lmited to, 0.1, 0.2., 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as dual integrin antibodies, or specified portions or variants, can also be included in the formulation.

Administration of Dual Integrin Antibody Compositions by a Nebulizer antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 μm, preferably in the range of about 1 μm to about 5 μm, and most preferably about 2 μm to about 3 μm.

Formulations of at least one anti-dual integrin antibody suitable for use with a nebulizer, either jet or ultrasonic, typically include a concentration of about 0.1 mg to about 100 mg of at least one anti-dual integrin antibody protein per ml of solution. The formulation can include agents such as an excipient, a buffer, an isotonicity agent, a preservative, a surfactant, and, preferably, zinc. The formulation can also include an excipient or agent for stabilization of the at least one anti-dual integrin antibody composition protein, such as a buffer, a reducing agent, a bulk protein, or a carbohydrate. Bulk proteins useful in formulating at least one anti-dual integrin antibody composition proteins include albumin, protamine, or the like. Typical carbohydrates useful in formulating at least one anti-dual integrin antibody include sucrose, mannitol, lactose, trehalose, glucose, or the like. The at least one anti-dual integrin antibody formulation can also include a surfactant, which can reduce or prevent surface-induced aggregation of the at least one anti-dual integrin antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

Administration of Dual Integrin Antibody Compositions by a Metered Dose Inhaler

In a metered dose inhaler (MDI), a propellant, at least one anti-dual integrin antibody, and any excipients or other additives are contained in a canister as a mixture including a liquefied compressed gas. Actuation of the metering valve releases the mixture as an aerosol, preferably containing particles in the size range of less than about 10 μm, preferably about 1 μm to about 5 μm, and most preferably about 2 μm to about 3 μm. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one anti-dual integrin antibody for use with a metered-dose inhaler device will generally include a finely divided powder containing at least one anti-dual integrin antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably the propellant is a hydrofluorocarbon. The surfactant can be chosen to stabilize the at least one anti-dual integrin antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein such as protein can also be included in the formulation.

One of ordinary skill in the art will recognize that the methods of the current invention can be achieved by pulmonary administration of at least one anti-dual integrin antibody compositions via devices not described herein.

Oral Formulations and Administration

Formulations for oral rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. No. 5,879,681 and U.S. Pat. No. 5,5,871,753 are used to deliver biologically active agents orally are known in the art.

Mucosal Formulations and Administration

For absorption through mucosal surfaces, compositions and methods of administering at least one anti-dual integrin antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Transdermal Formulations and Administration

For transdermal administration, the at least one anti-dual integrin antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

EXAMPLE 1

Cloning and Expression of Dual Integrin Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES lneo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277–279 (1991); Bebbington, et al., Bio/Technology 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Molec. Cell. Biol. 5:438–447 (1985)) plus a fragment of the CMV-enhancer (Boshart, et al., Cell 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

The vector pC4 is used for the expression of dual integrin antibody. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253: 1357–1370 (1978); J. L. Hamlin and C. Ma, Biochem. et Biophys. Acta 1097:107–143 (1990); and M. J. Page and M. A. Sydenham, Biotechnology 9:64–68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438–447 (1985)) plus a fragment isolated from the enhancer of the immediate early gene of human cytomegalovirus (CMV) (Boshart, et al., Cell 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the dual integrin in a regulated way in mammalian cells (M. Gossen, and H. Bujard, Proc. Natl. Acad. Sci. USA 89: 5547–5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The DNA sequence encoding the complete dual integrin antibody is used, corresponding to HC and LC variable regions of a dual integrin antibody of the present invention, according to known method steps. Isolated nucleic acid encoding a suitable human constant region (i.e., HC and LC regions) is also used in this.

The isolated variable and constant region encoding DNA and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 μg of the expression plasmid pC4 is cotransfected with 0.5 μg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 μg /ml G418. After 2 days, the cells are trypsinized and seeded in hybridoma cloning plates (Greiner, Germany) in alpha minus MEM supplemented with 10, 25, or 50 ng/ml of methotrexate plus 1 μg /ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100–200 mM. Expression of the desired gene product is analyzed, for instance, by SDS-PAGE and Western blot or by reverse phase HPLC analysis.

EXAMPLE 2

Method of Making and Characterization of Non-limiting Example of Fully Human Dual Integrin Antibody Summary. (CBA/J×C57/BL6/J) $F_2$ hybrid mice (Taylor et al., International Immunology 6:579–591 (1993); Lonberg et al., Nature 368:856–859 (1994); Neuberger, Nature Biotechnology 14:826 (1996); Fishwild et al., Nature Biotechnology 14:845–851 (1996)) containing human variable and constant region antibody transgenes for both heavy and light chains were immunized with human placental αVβ3. One fusion yielded 2 totally human αVβ3 reactive IgG1κ monoclonal antibodies, named GenO.95 and GenO.101. The totally human anti-αVβ3 antibodies were further characterized and both were found to be reactive to the αVβ3 and αVβ5 heterodimers suggesting specificity for the shared alpha chain of both molecules. One Mab, GenO.95, also known as CNTO 95, inhibits the binding of both αVβ3 and αVβ5 to vitronectin in cell based assays.

Abbreviations:
BSA—bovine serum albumin
$CO_2$—carbon dioxide
DMSO—dimethyl sulfoxide
EIA—enzyme immunoassay
FBS—fetal bovine serum
$H_2O_2$—hydrogen peroxide
HC—heavy chain
HRP—horseradish peroxidase
Ig—immunoglobulin
IP—intraperitoneal
IV—intravenous
Mab—monoclonal antibody
OD—optical density
OPD—o-Phenylenediamine dihydrochloride
PEG—polyethylene glycol
PSA—penicillin, streptomycin, amphotericin
RT—room temperature
SQ—subcutaneous
TBS—Tris buffered saline
v/v—volume per volume
w/v—weight per volume Introduction We have utilized transgenic mice that contain human heavy and light chain immunoglobulin genes to generate totally human monoclonal antibodies that are specific to the αV integrins. These novel antibodies can be used therapeutically to inhibit the angiogenic process by blocking the binding of αV integrins to their respective ECM ligands and provide additional tools in the treatment of various cancers.

Materials and Methods

Animals

Transgenic mice have been developed by GenPharm International that express human immunoglobulins but not mouse IgM or Igκ. These mice contain human sequence transgenes that undergo V(D)J joining, heavy-chain class switching and somatic mutation to generate a repertoire of human sequence immunoglobulins (Taylor et al., International Immunology 6:579–591 (1993)). The light chain transgene is derived in part from a yeast artificial chromosome clone that includes nearly half of the germline human Vκ region. In addition to several VH genes, the heavy-chain (HC) transgene encodes both human μ and human γ1 (Lonberg et al., Nature 368:856–859 (1994)) and/or γ3 constant regions. A mouse derived from the HC012 genotypic lineage was used in the immunization and fusion process to generate these monoclonal antibodies.

Purification of Human αVβ3

Human placenta (disrupted using a meat grinder) or M21 human melanoma cells expressing the αVβ3 integrin were extracted with saline containing 20 mM Tris pH 7.5, 1 mM $CaCl_2$, 1 mM $MnCl_2$, 100 mM Octylthioglucoside (OTG from Pierce), 0.05% sodium azide and 1 mM phenylmethylsulfonyl fluoride (Sigma). The mixture was stirred for 1 hr at room temperature and clarified by centrifugation at 10,000×g. The supernatant from placental extracts was applied to an affinity column consisting of Mab 10E5 coupled to sepharose (Pharmacia) to remove GPIIb/IIIa and the flow-through fraction was applied to an affinity column consisting of Mab c7E3 Fab coupled to sepharose (Pharmacia) to bind αVβ3. The c7E3 column was washed with PBS containing 1 mM $CaCl_2$, 1 mM $MnCl_2$, and 0.1% OTG followed by 0.1M sodium acetate pH 4.5, 1 mM $CaCl_2$, 1 mM $MnCl_2$, and 0.1% OTG, pH 3.0. The column was eluted with 0.1M glycine, 2% acetic acid, 1 mM $CaCl_2$, 1 mM $MnCl_2$, and 0.1% OTG. The eluate containing purified αVβ3 was neutralized using 2M Tris pH 8.5. Purity of the preparations was characterized by SDS-PAGE analysis and ELISA to rule out GPIIb/IIIa contamination (Wayner, et al., J. Cell Biol. 113: 919–929 (1991)).

Immunizations

A fifteen to 17 week old surgically castrated male mouse obtained from GenPharm was immunized IP (200 μL) and in 2 sites SQ (100 μL per site) with a total of 20 μg of placental αVβ3 (prep V fraction, JG21197) emulsified with an equal volume of complete Freund's adjuvant (day 0). The mouse was immunized two weeks later in the same manner with αVβ3 emulsified with an equal volume of incomplete Freund's adjuvant. Three subsequent 10 μg IP/10 μg SQ injections with incomplete Freund's adjuvant were administered on days 28, 42, and 56. The mouse was then bled on days 42 and 56 by retro-orbital puncture without anti-coagulant. The blood was allowed to clot at RT for one hour and the serum was collected and titered using an αVβ3 solid phase EIA assay. The fusion, named GenO, was performed when repeated injections did not cause titers to increase. At that time, the mouse with a specific human IgG titer of 1:1280 against αVβ3 was given a final IV booster injection of 10 μg αVβ3 diluted in 100 μL physiological saline. Three days later, the mouse was euthanized by cervical dislocation and the spleen was removed aseptically and immersed in 10 mL of cold phosphate buffered saline (PBS) containing 100 U/mL penicillin, 100 μg/mL streptomycin, and 0.25 μg/mL amphotericin B (PSA). The splenocytes were harvested by sterilely perfusing the spleen with PSA-PBS. The cells were washed once in cold PSA-PBS, counted using Trypan blue dye exclusion and resuspended in RPMI 1640 media containing 25 mM Hepes.

Cell Lines

The non-secreting mouse myeloma fusion partner, SP2/0 was received into Cell Biology Services (CBS) group on Sep. 1, 1993. The cell line was expanded in αMEM (modified) medium (JRH Biosciences) supplemented with 10% (v/v) FBS (Cell Culture Labs), 1 mM sodium pyruvate, 0.1 mM NEAA, 2 mM L-glutamine (all from JRH Biosciences) and cryopreserved in 95% FBS and 5% DMSO (Sigma), then stored in a vapor phase liquid nitrogen freezer in CBS. The cell bank was sterile (Quality Control Centocor, Malvern) and free of mycoplasma (Bionique Laboratories). Cells were maintained in log phase culture until fusion. They were washed in PBS, counted, and viability determined (>95%) via trypan blue dye exclusion prior to fusion.

The M21 cell line, a human melanoma expressing the αVβ3 and αVβ5 integrins, was expanded and cryopreserved. The 10-vial research cell bank was received into Cell Biology Services and stored in liquid nitrogen. The cell bank was sterile and free of mycoplasma (Bionique Laboratories). The MDAMB435L2 cell line, a human breast carcinoma, was a gift from Dr. Janet Price (MD Anderson, Houston Tex.) expresses the integrin αVβ3. The cell line was cryopreserved in Cell Biology Services. The cell bank was sterile and free of mycoplasma (Bionique Laboratories). M21 and MDAMB435L2 cells were thawed, propagated in appropriate media and maintained in log phase for several days prior to use in bioassays or allowed to reach confluency for use in the purification of αVβ3 protein (M21 cells).

Cell Fusion

Fusion was carried out at a 1:1 ratio of murine myeloma cells (SP2/0) to viable spleen cells. Briefly, spleen cells and myeloma cells were pelleted together. The pellet was slowly resuspended, over 30 seconds, in 1 mL of 50% (w/v) PEG/PBS solution (PEG molecular weight 3,000, Sigma) at 37° C. The fusion was stopped by slowly adding 1 mL of Dulbecco's PBS (JRH) (37° C.) over 1 minute. An additional 19 mL of PBS was added over the next 90 seconds. The fused cells were centrifuged for 5 minutes at 750 rpm. The cells were then resuspended in HAT medium (αMEM medium containing 20% Fetal Bovine Serum (JRH), 1 mM sodium pyruvate, 2 mM L-glutamine, 0.1 mM Non-essential amino acids, 10 µg/mL gentamicin, 2.5% Origen culturing supplement (Fisher), 50 µM 2-mercaptoethanol, 100 µM hypoxanthine, 0.4 µM aminopterin, and 16 µM thymidine) and then plated at 200 µL/well in thirteen 96-well flat bottom tissue culture plates. The plates were then placed in a humidified 37° C. incubator containing 5% $CO_2$ and 95% air for 7–10 days.

Detection of Human IgG Anti-αVβ3 Antibodies in Mouse Serum

Solid phase EIAs were used to screen mouse sera for human IgG antibodies specific for human αVβ3. Briefly, plates were coated with αVβ3 at 1 µg/mL in PBS overnight. After washing in 0.15M saline containing 0.02% (v/v) Tween 20, the wells were blocked with 1% (w/v) BSA in HBSS with $Ca^{++}$ and $Mg^{++}$, 200 µL/well for 1 hour at RT. Plates were used immediately or frozen at −20° C. for future use. Mouse sera were incubated in doubling dilutions on the αVβ3 coated plates at 50 µL/well at RT for 1 hour. The plates were washed and then probed with 50 µL/well HRP-labeled goat anti-human IgG, Fc specific (Accurate) diluted 1:30,000 in 1% BSA-PBS for 1 hour at RT. The plates were again washed and 100 µL/well of the citrate-phosphate substrate solution (0.1M citric acid and 0.2M sodium phosphate, 0.01% $H_2O_2$ and 1 mg/mL OPD) was added for 15 minutes at RT. Stop solution (4N sulfuric acid) was then added at 25 µL/well and the OD's were read at 490 nm via an automated plate spectrophotometer.

Detection of Totally Human Immunoglobulins in Hybridoma Supernatants

Because the GenPharm mouse is capable of generating both mouse and human immunoglobulin chains, growth positive hybridomas secreting fully human immunoglobulins were detected using two separate EIA sysetms. Plates were coated as described above and undiluted hybridoma supernatants were incubated on the plates for one hour at 37° C. The plates were washed and probed with either HRP labeled goat anti-human kappa (Southern Biotech) antibody diluted 1:10,000 in 1% BSA-HBSS or HRP labeled goat anti-human IgG Fc specific antibody diluted to 1:30,000 in 1% BSA-HBSS for one hour at 37° C. The plates were then incubated with substrate solution as described above.

Isotyping

Isotype determination of the antibodies was accomplished using an EIA in a format similar to that used to screen the mouse immune sera for specific titers. αVβ3 was coated on 96-well plates as described above and purified antibody at 2 µg/mL was incubated on the plate for one hour at RT. The plate was washed and probed with HRP labeled goat anti-human $IgG_1$ (Binding Site) or HRP labeled goat anti-human $IgG_3$ diluted at 1:4000 (Zymed) in 1% BSA-HBSS for one hour at RT. The plate was again washed and incubated with substrate solution as described above.

Binding Characteristics of Human Monoclonal Antibodies by EIA

Binding characteristics for the antibodies were assessed using an αVβ3 capture EIA. Linbro plates were coated with αVβ3 at 1 µg/mL in TBS with 2mM calcium overnight at 4° C. Plates were washed and blocked with TBS/1% BSA/calcium for at least one hour at room temperature. Purified antibodies were incubated in doubling dilutions from a starting concentration of 2 µg/mL. Plates were washed and conjugated antibodies (HRP-labeled goat anti-human IgG Fc at 1:30,000) were added and incubated on plates for one hour at room temperature. Plates were washed OPD substrate was added to wells. Plates were read via an automated plate spectrophotometer.

Competition of Binding of Gen095 to M21 Cells by Various Commercial anti-Integrin Mabs M21 Cells were trypsinized from culture flasks, washed and resuspended in HBSS/calcium to $2 \times 10^6$ cell/mL. Gen095 was prelabeled with FITC-goat anti-human Fc (Jackson) for 30 minutes at RT. 10× concentrations of Gen095 of 200 µg/mL or 20 µg/mL were incubated with FITC-goat anti-human IgG at 250 µg/mL. Aliquots of 100 µL of M21 cells ($2 \times 10^5$ cells) were incubated with 12 µL 10× Gen095 at high (20 µg/mL final) and low (2 µg/mL final) concentrations ±12 µL of the following murine antibodies: m7E3 IgG, anti-αVβ3 (clone LM609, Chemicon), anti-αVβ5 (clone PIF6, Gibco), anti-β3 (Chemicon, AMAC), or anti-αV (clone VNR139, Gibco) antibodies (at 20 µg/mL) for 45 minutes at 37° C. An aliquot was removed from each tube (for two-color analysis) and the remainder was fixed with 1% paraformaldehyde and analyzed on a flow cytometer. For two-color analysis, an aliquot (50 µL) was incubated with PE-goat anti-mouse IgG for 30 minutes at RT to label murine anti-αVβ3, anti-αVβ3, anti-α3, or anti-αV antibodies for two-color analysis. All tubes were fixed with 1% paraformaldehyde.

Inhibition of αVβ3 or αVβ5 Dependent M21 Cell or MDAMB435L2 Cell Adhesion to Vitronectin Coated Plates by αVβ3/αVβ5 Specific Mabs Linbro plates were coated for 1 hour at room temperature 50 µL/well of vitronectin (Collaborative, Becton Dickinson) at 5 µg/mL in TBS with 2 mM calcium. Plates were washed with HBSS/calcium and blocked with TBS containing 2 mM calcium and 1% BSA for 30 minutes at RT. M21 cells were trypsinized, washed once with media containing FCS and resuspended in 3 mL HBSS without calcium. All washes were done with 10 minute spins at 1000 rpm in the Sorvall tabletop centrifuge. To fluorescently label the cells, calcein (Molecular Probes) (5 mg/mL in DMSO) was added to the cells to a final concentration of 100 µg/mL in a 50 mL conical tube (wrapped in foil). Cells were incubated 10 to 15 minutes at 37° C. Calcein labeled cells were washed once with HBSS and resuspended in HBSS supplemented with 0.1% BSA and 1 mM $MgCl_2$. Antibodies were titrated (14-fold dilution series) in HBSS/0.1% BSA/2 mM calcium at 10× final concentration. Cells (300 µL at $7.5 \times 10^6$/mL) were preincubated with antibody titrations (37 µL of 10× solution)±anti-αVβ5 (P1F6) ascites (Chemicon) (37 µL of 1:600 (10×)) for 15 min at 37° C. The cell-antibody mixture was added to the vitronectin-coated plates at 100 µL/well in triplicate (approximately $6 \times 10^5$ cells/well). Plates were incubated for 45 minutes at 37° C. Unbound cells were removed by two washes with HBSS/calcium (150 µL/well).

100 μl HBSS/calcium was added to each well and the plate read on the Fluoroskan at 485–538 nm.

In a separate assay, MDAMB435L2 human breast carcinoma cells were harvested with versene and suspended in serum free media at 500,000 cells/mL and incubated with various concentrations of GenO95. After 10 minutes of incubation tumor cell suspension (100 μL) was added to vitronectin (10 μg/mL) coated Linbro plates and incubated at 37° C. After 1 hour, wells were washed three times with serum free media (200 μL/wash) and the MTT based Cell Titer AQ dye (Promega) was added to each well. Extent of cell adhesion was determined in an ELISA plate reader where OD490 nm is directly proportional to cell adhesion. Cell adhesion to BSA coated wells served as negative control.

Figure 4A:
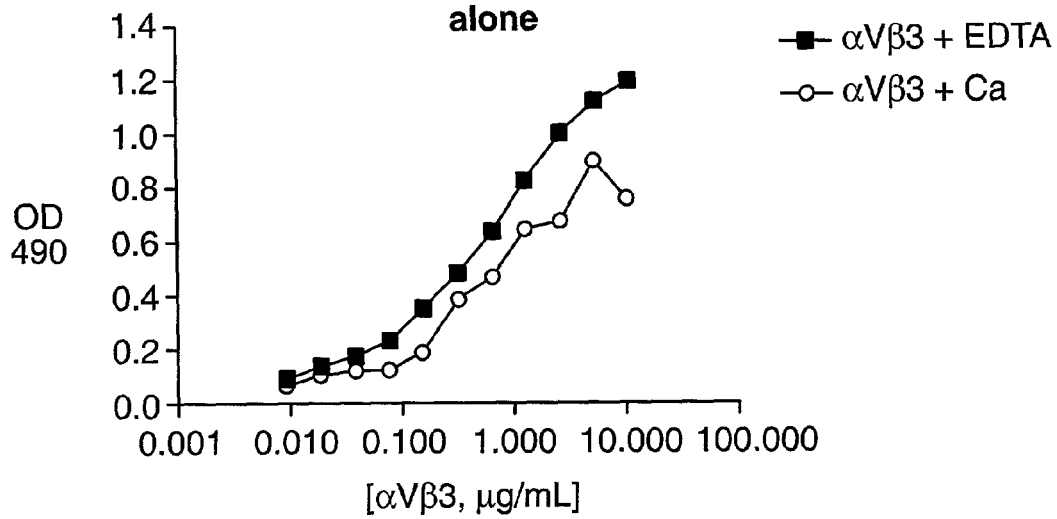
FIGS. 4A–D show graphs of antibody binding to $\alpha V \beta 3$ where this ligand was preincubated in doubling dilutions starting at 10 :g/mL with 50 mM EDTA in 1% BSA-HBSS (in the absence of Ca++) or with 1% BSA-HBSS (with Ca++) for 30 min, 37EC. Mixtures added to plates coated with CNTO 95, C372, c7E3 or LM609 IgG and incubated for 1 hour, 37° C. LM609 or CNTO 95 added a 20 :g/mL in appropriate buffer (+/–Ca++) for 30 min, 37° C. Plates probed with goat anti-mouse IgG Fc, HRP or goat anti-human IgG Fc, HRP.
Figure 4B:
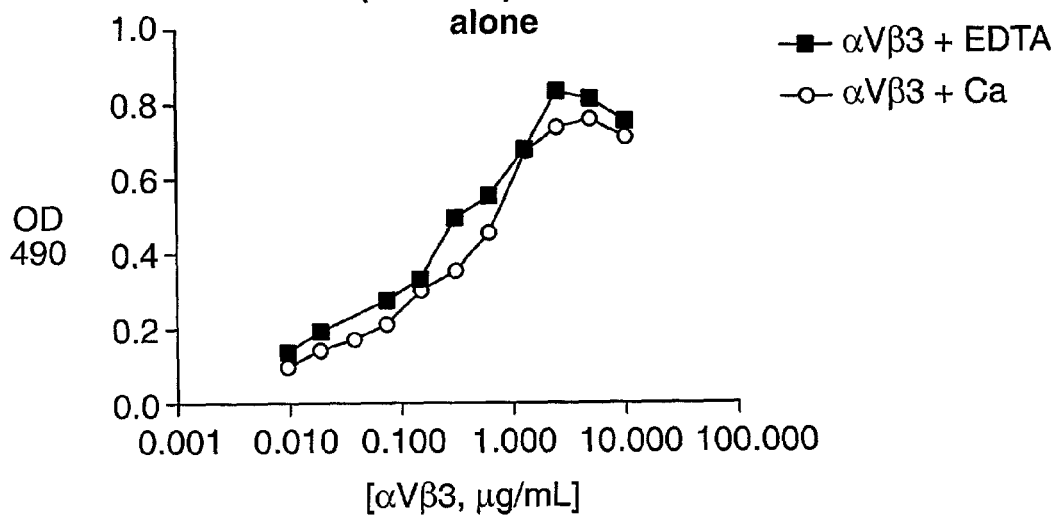
Figure 4C:
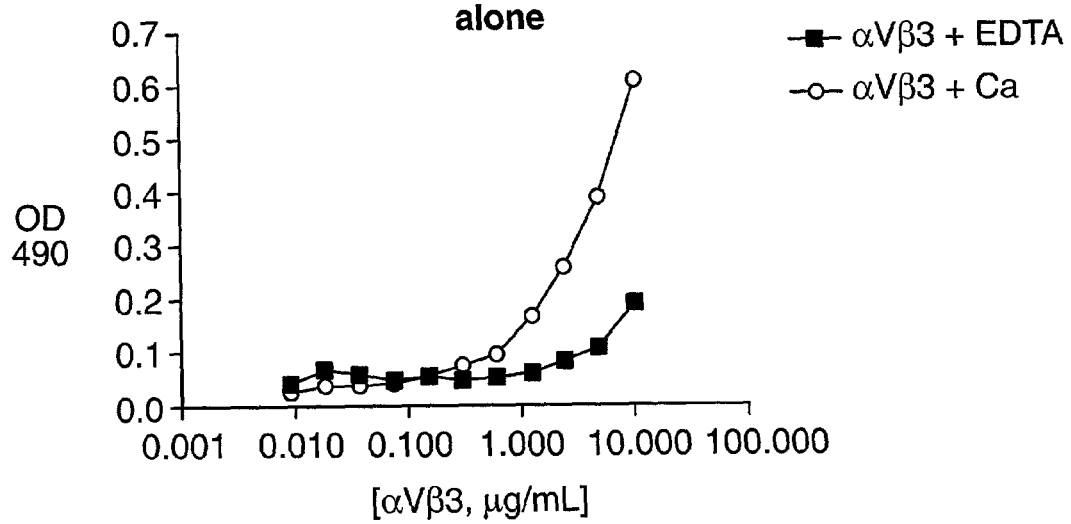
Figure 4D:
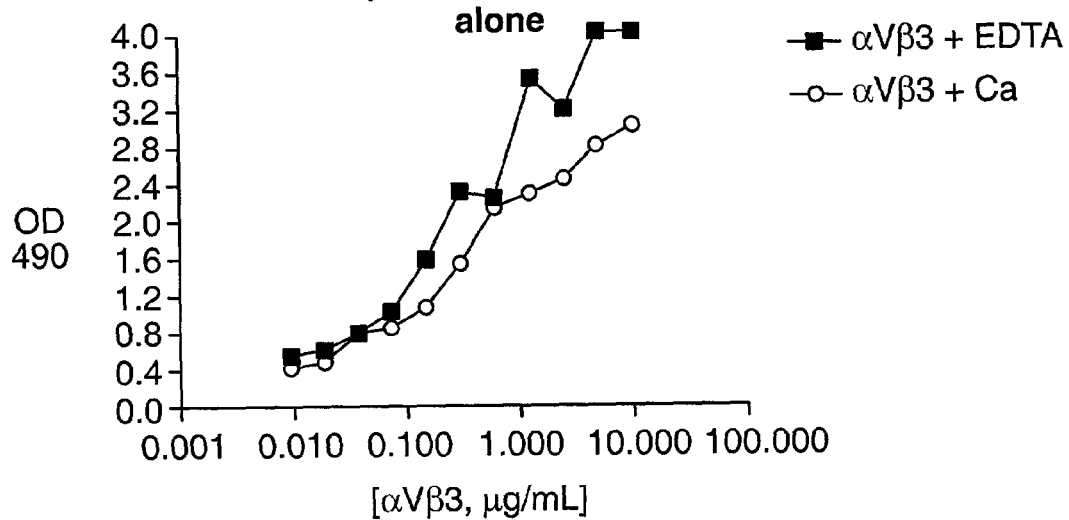
Figure 4E:
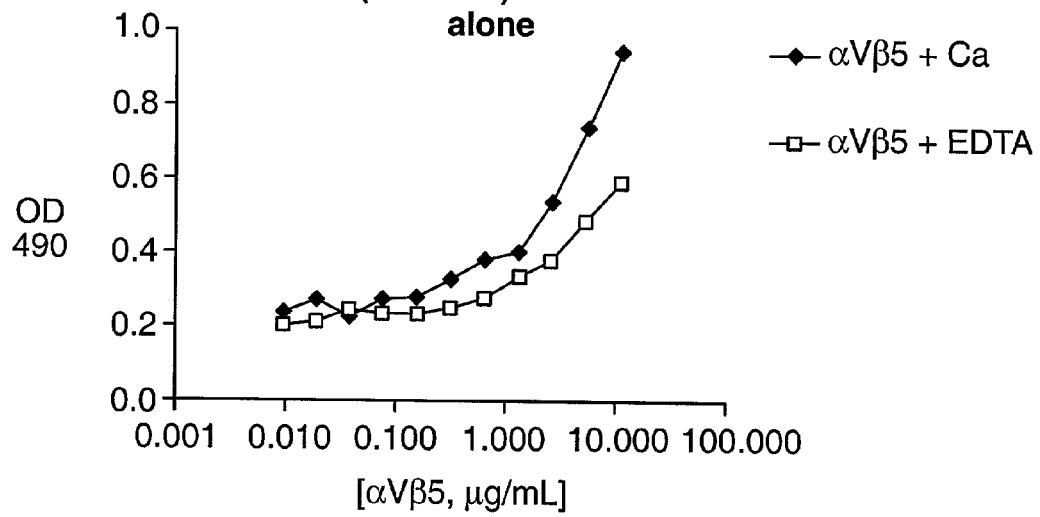
FIGS. 4E–G show graphs of antibody binding to a $\alpha V \beta 5$, where this ligand was preincubated in doubling dilutions starting at 10 :g/mL with 50 mM EDTA in 1% BSA-HBSS (in the absence of Ca++) or with 1% BSA-HBSS (with Ca++) for 30 min, 37° C. Mixtures added to plates coated with CNTO 95, C372, c7E3 IgG and incubated for 1 hour, 37° C. VNR139 was added at 10 :g/mL in appropriate buffer (+/–Ca++) for 30 min, 37° C. Plates probed with goat anti-mouse IgG Fc, HRP.
Figure 4F:
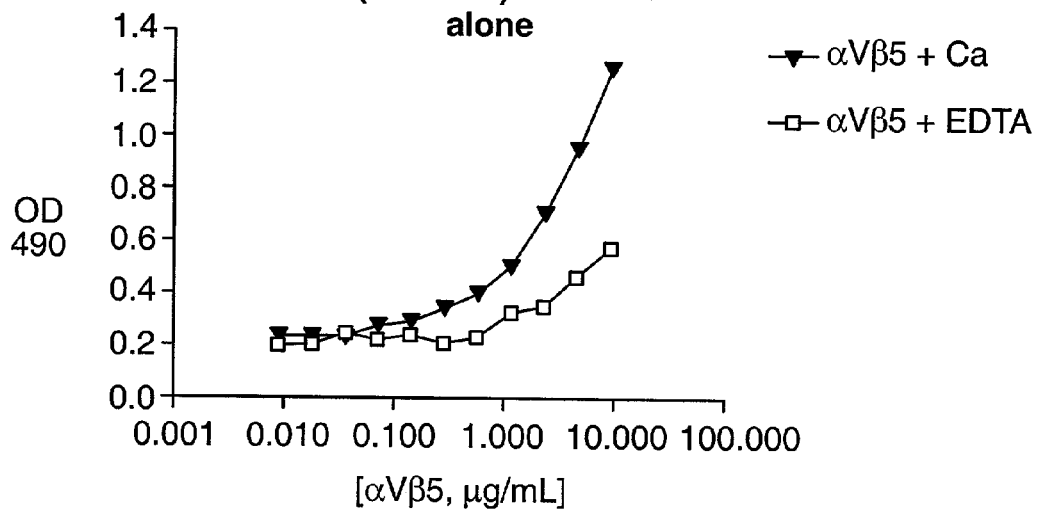
Figure 4G:
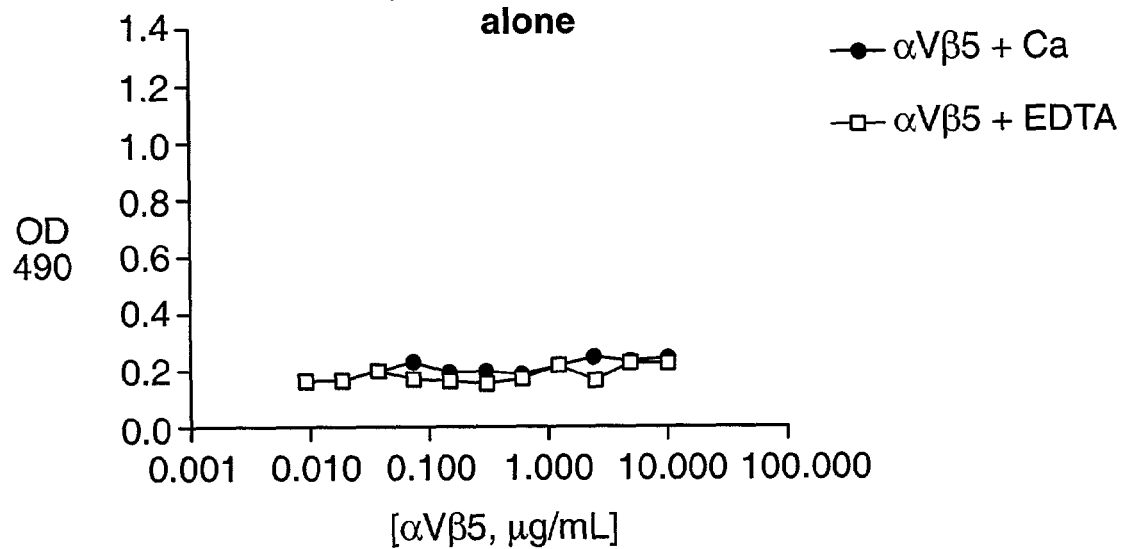

Determination of $Ca^{++}$ Dependence for Binding of anti-Human αVβ3/αVβ5 Mabs to Their Ligands It is known that the presence of the cation calcium is necessary for the Mab c7E3 to bind αVβ3 and is not a requirement for binding of Mab LM609 to αVβ3 as demonstrated in FIGS. 4c and 4d respectively. This experiment was conducted to assess whether calcium dependence also applies to the binding characteristics of CNTO 95 or C372 for αVβ3 or αVβ5 integrins. An excess concentration of EDTA was introduced into the assay format to chelate the Ca present within the binding pocket of the integrin heterodimers and therefore, binding was assessed in the absence of the cation. It was found that CNTO 95 and C372 binding to αVβ3 is not dependent upon the presence of Ca (FIG. 4a, 4b). The same is true for CNTO 95 binding to αVβ5 but not so, however, for C372 binding to αVβ5 (FIG. 4e, 4f) as binding appears to be increased in the presence of Ca.

Results and Discussion

Generation of Totally Human Anti-Human αVβ3 Integrin Monoclonal Antibodies

One fusion, named GenO, was performed from a GenPharm mouse immunized with αVβ3 protein. From this fusion, 129 growth positive hybrids were screened. Two hybridoma cell lines were identified that secreted totally human IgG antibodies reactive with human αVβ3. These two cell lines, GenO.95.9.12 and GenO.101.17.22, each secrete immunoglobulins of the human IgG1κ isotype and both were subcloned twice by limiting dilution to obtain stable cell lines (>90% homogeneous). GenO.95.9.12 was assigned C-code #CNTO 95 and GenO.101.17.22 was assigned C-code #C372A. Each of the cell lines was frozen in 12-vial research cell banks stored in LN2.

Binding Characteristics of Human Monoclonal Antibodies by EIA

ELISA analysis confirmed that purified antibody from the two hybridomas, CNTO 95 and C372A, bind αVβ3 in a concentration-dependent manner. FIG. 1 shows the results of the relative binding efficiency of the antibodies. Fifty percent binding is achieved at 0.07 and 0.7 μg/mL for C372A and CNTO 95 respectively. In the same assay, c7E3 IgG demonstrated fifty-percent maximal binding at 0.07 μg/mL.

Competition of Binding of Mab GenO95 to M21 Cells by Commercially Available anti-Integrin Mabs By single-color analysis, none of the murine anti-$α_vβ_3$, anti-$α_vβ_5$, anti-$β_3$, or anti-$α_v$ antibodies competed with CNTO 95 for binding to M21 cells (Table 1). This experiment also demonstrates that CNTO 95 binds to M21 cells in a dose dependent manner. The two-color analysis demonstrated that the murine anti-$α_vβ_3$, anti-$α_vβ_5$, anti-$β_3$, or anti-$α_v$ antibodies were able to bind to M21 cells (data not shown).

TABLE 1

Competition of Binding of GenO95 to M21 Cells by Murine anti-Integrin Mabs

| | FITC-goat anti-human Fc-labeled GenO95 | | | |
|---|---|---|---|---|
| | 2 μg/mL | | 20 μg/mL | |
| Competing Antibody | MCF | % Positive | MCF | % Positive |
| negative (no GenO95) | 2.69 | | 2.69 | |
| Positive (saline) | 4.33 | 100% | 14.33 | 100% |
| m7E3 IgG | 5.73 | 132% | 14.72 | 103% |
| LM609 (anti-$α_vβ_3$) | 4.78 | 110% | 13.34 | 93% |
| anti-$β_3$ (Chemicon) | 5.42 | 125% | 13.10 | 91% |
| anti-$β_3$ (AMAC) | 4.61 | 106% | 13.10 | 91% |
| P1F6 (anti-$α_vβ_5$) | 4.87 | 112% | 14.46 | 101% |
| VNR139 (anti-$α_v$) | 4.61 | 106% | 14.86 | 104% |

MCF = Median Channel Fluorescence

Figure 2:
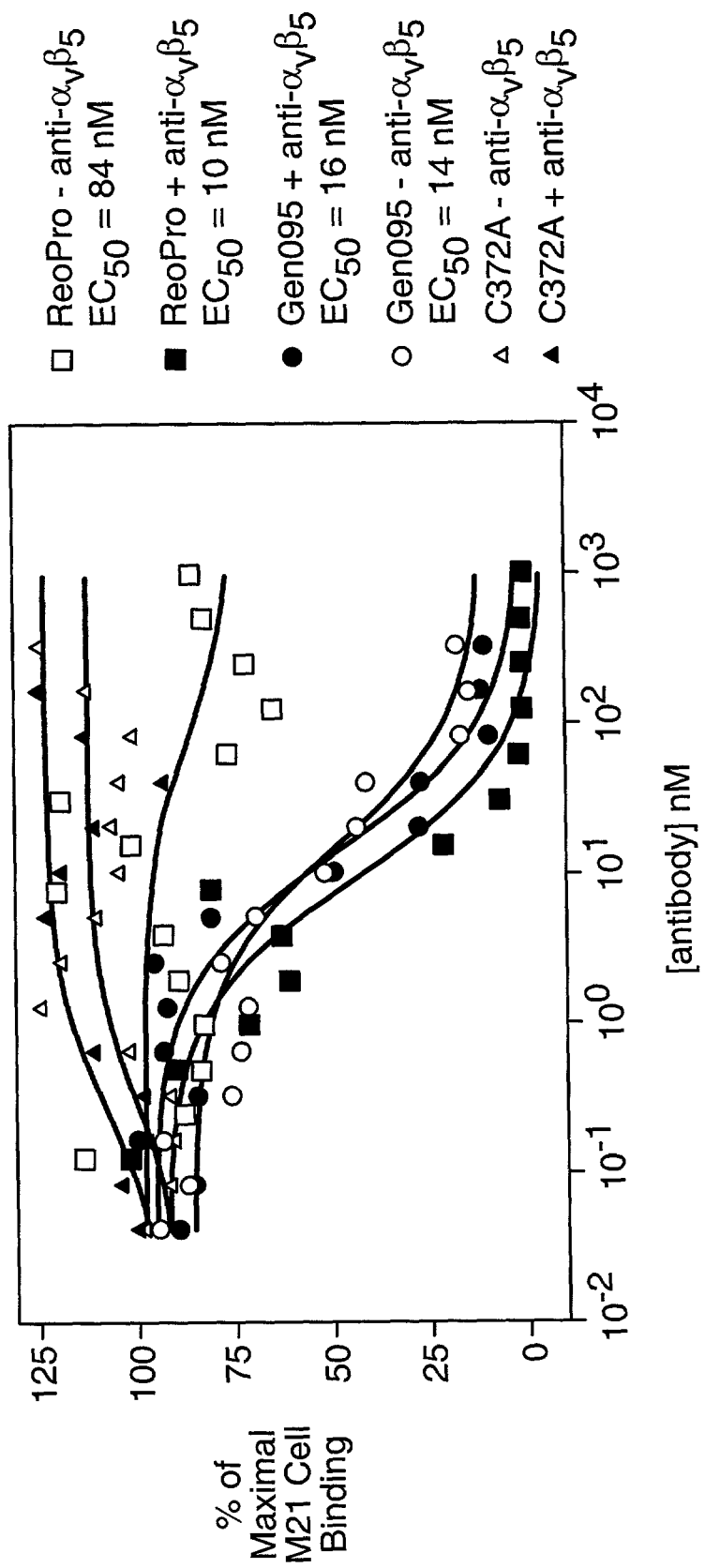
FIG. 2 show a graph of calcein-labeled M21 cells were preincubated with antibody samples in the absence or presence of P1F6, anti-$\alpha V \beta 5$ ascites for 30 minutes, then added to vitronectin coated plates for 45 minutes. Non-bound M21 cells were removed with two 150 μL/well washes with HBSS with calcium. Plate was read on a fluorometer at 485–538 nm.

Inhibition of αVβ3 or αVβ5 Dependent M21 Cell or MDAMB435L2 Cell Adhesion to Vitronectin Coated Plates by αVβ3/αVβ5 Specific Mabs M21 cells adhere to vitronectin coated plates in an αVβ3 and αVβ5 dependent manner. Therefore, blockade of both αVβ3 and αVβ5 is required to completely inhibit M21 cell adhesion to vitronectin coated plates. C372A did not inhibit M21 cell adhesion in the presence or absence of P1F6, anti-αVβ5 ascites (FIG. 2). GenO95 (CNTO 95) completely inhibited M21 cell adhesion to vitronectin coated plates both with and without anti-αvβ5 (P1F6) ascites, indicating that the antibody blocks both αVβ3 and αVβ5. As a control for the assay parameters, ReoPro (c7E3 Fab) which blocks αVβ3 (in addition to GPIIb/IIIa) was included. ReoPro alone only partially inhibited M21 cell adhesion, ReoPro in the presence of anti-$α_vβ_5$ (P1 F6) ascites completely inhibited adhesion, which demonstrates that M21 cells bind to vitronectin through both $α_vβ_3$ or $α_vβ_5$ integrins. Data were normalized to percent of maximal M21 cell binding in the absence of antagonist+/−anti-αVβ5 (P1F6) ascites. For antagonist titration without P1 F6, data were normalized to maximal M21 cell binding in the absence of antagonist or P1F6. For antagonist titration in the presence of P1F6, data were normalized to maximal binding in the absence of antagonist but in the presence of P1 F6. Data were graphed as percent of maximal binding (no antibody) and non-linear regression performed using GraphPad Prism.

Gen095 Mab also demonstrated the ability to completely inhibit MDAMB435L2 cell adhesion to vitronectin at a minimal concentration of 1.5 μg/mL (FIG. 3). These data, in combination with the data indicating inhibition of M21 cell adhesion, confirm the ability of GenO95 to functionally inhibit the αVβ3 and/or αVβ5 receptor interaction with vitronectin.

Determination of $Ca^{++}$ Dependence for Binding of anti-Human ∀V∃3/∀V∃5 Mabs to Their Ligands It is known that the presence of the cation calcium is necessary for the Mab c7E3 to bind ∀V∃3 and is not a requirement for binding of Mab LM609 to αVβ3 as demonstrated in FIGS. 4c and 4d respectively. This experiment was conducted to assess whether calcium dependence also applies to the binding characteristics of CNTO 95 or C372 for ∀V∃3 or ∀V∃5 integrins. An excess concentration of EDTA was introduced into the assay format to chelate the Ca present within the binding pocket of the integrin heterodimers and therefore, binding was assessed in the absence of the cation. It was found that CNTO 95 and C372 binding to ∀V∃3 is not dependent upon the presence of Ca (FIG. 4a, 4b). The same is true for CNTO 95 binding to ∀V∃5 but not so, however, for C372 binding to ∀V∃5 (FIG. 4e, 4f) as binding appears to be increased in the presence of Ca.

CONCLUSION

The GenO fusion was performed utilizing splenocytes from a hybrid mouse containing human variable and constant region antibody transgenes that was immunized with human αVβ3. Two totally human αVβ3 reactive IgG monoclonal antibodies of the IgG1 κ isotype were generated. These Mabs were further characterized and it was found that both bind αVβ3 and αVβ5 integrins. The binding of the two Mabs was demonstrated to be calcium independent to ∀V∃3 and calcium dependent to ∀V∃5 only for C372 binding. Moreover, one Mab, GenO95 (CNTO 95), is able to completely inhibit the binding of αVβ3 and αVβ5 to the ligand vitronectin in cell based assays. This Mab may prove useful in anti-angiogenic and other cancer related applications.

REFERENCES

1. Taylor et al., International Immunology 6:579–591 (1993).
2. Lonberg et al., Nature 368:856–859 (1994).
3. Neuberger, Nature Biotechnology 14:826 (1996).
4. Fishwild et al., Nature Biotechnology 14:845–851 (1996).
5. Gastl et al., Oncology 54: 177–184 (1997).
6. Eliceiri, et al., J. Clin. Invest. 103: 1227–1230 (1999).
7. Friedlander et al., Science 270: 1500–1502 (1995).
8. Wayner, et al., J. Cell Biol. 113: 919–929 (1991).

EXAMPLE 3

Binding Affinities for Dual Integrin Antibody

Introduction

GenO.95, also known as CNTO 95, is a human monoclonal antibody generated by immunizing (CBA/J×C57/BL6/J, GenPharm International) F2 hybrid mice with $\alpha_v\beta_3$ integrin purified from human placenta. The antibody is composed of human variable and IgG1 kappa constant regions and found to be reactive to both $\alpha_v\beta_3$ and $\alpha_v\beta_5$, suggesting a specificity for the alpha chain shared by both integrin molecules.

Objective

The purpose of this study is to characterize the binding affinity of GenO.05 for $\alpha_v\beta_3$ and $\alpha_v\beta_5$ purified integrins and for beta integrin expressing cell lines. For further characterization, the binding values will be compared between GenO.95 and ReoPro.

Abbreviations

Kd, equilibrium dissociation constant, expressed in M
Bmax=maximal number of binding sites Materials and Methods Cell Lines A375S2 cells, a human melanoma cell line expressing $\alpha_v\beta_3$ and $\alpha_v\beta_5$ integrins, were cultured in Dulbelcco's minimal media (DMEM) containing 10% fetal bovine serum (FBS, Cell Culture Labs), 1 mM sodium pyruvate, 0.1 mM nonessential amino acids, and 2 mM L-glutamine (all from JRH Biosciences).

HT29 cells, a human colon carcinoma cell line expressing $\alpha_v\beta_5$ and minimal $\alpha_v\beta_3$ (NB 4546, p207) were cultured in DMEM containing 10% FBS, 1 mM sodium pyruvate, 0.1 mM nonessential amino acids, and 2 mM L-glutamine.

M21 cells, a human melanoma expressing $\alpha_v\beta_3$ and $\alpha_v\beta_5$ integrins, obtained from Dr. J. Jakubowski (Eli Lilly, Inc.), were cultured in RPMI media (JRH Biosciences) containing 10% FBS, 1 mM sodium puruvate, 0.1 mM nonessential amino acids, and 2 mM L-glutamine.

Integrins $\alpha_v\beta_3$ lot JG22499 was purified at Centocor from human placenta. Another $\alpha_v\beta_3$ integrin lot (octyl formulation, lot 19100991) was purchased from Chemicon. $\alpha_v\beta_5$ (Triton formulation, lot 20030055, lot 1910990 and octyl formulation, lot 19060747) was purchased from Chemicon.

Antibodies

GenO.95 was purified from cell culture supernatant by Protein A chromatography. ReoPro was manufactured at Centocor, Inc. LM609, a murine anti-human $\alpha_v\beta_3$ antibody, (1976ZK, lot 20020559 and lot 1910329) and P1F6, a murine anti-human $\alpha_v\beta_5$ antibody (1961 P-K, lot 17110560) were purchased from Chemicon.

Radiolabeling

Antibodies were radiolabeled with 125-I Na (Amersham, Ill.) using Iodobeads (Pierce Chemicals, Ill.) to a specific activity of 1–2 μCi/μg. Antibody concentration (mg/ml) was determined by dividing the adsorption (OD/ml) at 280 nm by 1.4. Specific activity of the iodinated antibody was determined by diluting the antibody and counting an aliquot in the gamma counter or Topcounter (Packard).

$$\text{Specific activity (cpm/\mu g)} = \frac{\text{cpm/volume (ml)} \times \text{dilution factor}}{\text{concentration (\mu g/ml determined by } OD_{280} \text{ reading)}}$$

Integrin-coated Plate Binding Assay $\alpha_v\beta_3$ or $\alpha_v\beta_5$ integrin was diluted to 1 μg/ml in Tris-buffered saline (TBS, 10 mM Tris, 100 mM NaCl, pH 7.5) containing 2 mM calcium chloride (TBS/Ca$^{++}$) and coated at 50 μl per well onto 96 well polystyrene Linbro plates (Flow/ICN) overnight at 4° C. Plates were washed with TBS/Ca$^{++}$ and blocked with 1% bovine serum albumin (BSA) in TBS/Ca$^{++}$ for 1 h at room temperature. Fifty microliters of diluted antibody was added in triplicate to coated wells and incubated for 2 h at 37° C. After three washes with TBS-Tween buffer (TBS+0.1% Tween 20), peroxidase conjugated goat anti-human IgG F(ab')$_2$ (H+L, Jackson lot 16869), at 1:40:000 dilution in 1% BSA-TBS was added and incubated for 1 h at room temperature. Plates were washed three times, and developed with o-phenylenediamine dihydrochloride substrate solution (OPD, Sigma) consisting of 0.1 M citric acid, 0.2M sodium phosphate, 0.01% H$_2$O$_2$ and 1 mg/ml OPD. Color development was stopped after 15 min at room temperature with 0.3 N H$_2$SO$_4$, and plates were read at OD$_{490}$ nm in the Molecular Dynamics plate reader.

Binding curves were generated with GraphPad PRISM (version 3, GraphPad Software). Results were expressed as % maximal binding of the saturation value. Kd, the equilibrium dissociation binding constant (expressed as M), was determined from a non-linear regression fit of the data using PRISM.

Cell Binding Assay

Fifty microliters of diluted radiolabeled antibody in 2% RPMI media containing 2% bovine serum albumin (JRH Biosciences) were added in triplicate to confluent cells cultured in 96 well tissue culture plates (Packard). Cells were incubated for 1.5 h at 37° C.; gently washed three times with Hanks buffered saline containing calcium and magnesium (HBSS++, JRH Biosciences) and then aspirated. One hundred microliters of Mycosinct 20 (Packard) was added per well, and cell-bound radioactivity was quantified in the TopCounter (Packard).

To determine nonspecific binding, experiments were performed with a similar set of dilutions in the presence of 100-fold excess of unlabeled antibody.

To determine the number of cells plated in each well, cells from several wells were removed with trypsin, pooled and counted under the microscope. The receptor number per cell was calculated as follows:

$$\text{Receptor number/cell} = \frac{\text{specific bound cpms} \times 6.023 \times 10^{23} \text{ molecules/mole}}{\text{specific activity (cpm/g)} \times \text{mol. wt. (g/mole)} \times \text{cell number}}$$

Bmax, the maximal binding sites per cell, and the Kd were determined from a nonlinear regression fit of the data using PRISM.

Results and Discussion

Figure 5A:
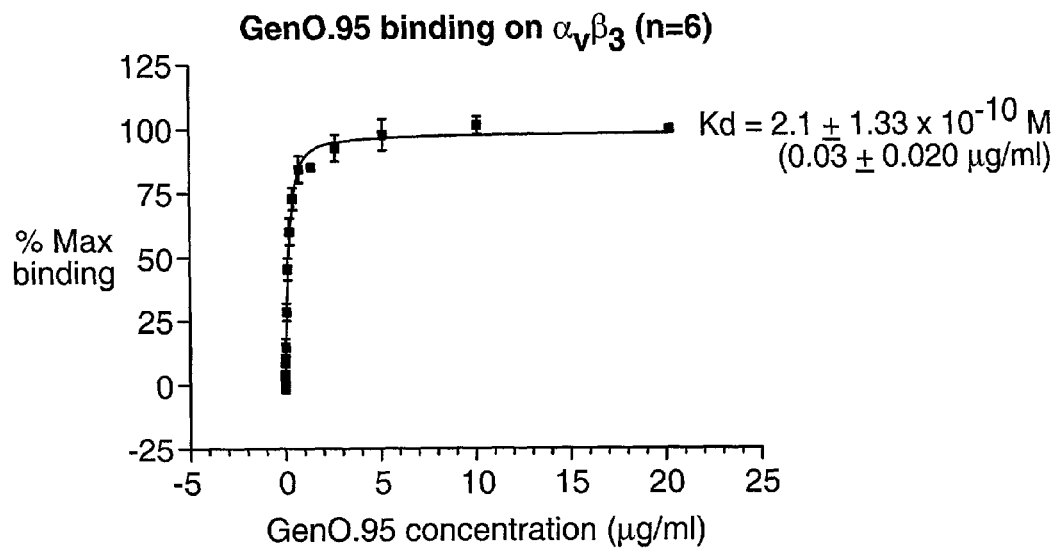
FIG. 5A–B shows a graph of saturation binding curve of GenO.95 (FIG. 5A) and ReoPro (FIG. 5B) on $\alpha v \beta 3$ coated plates.
Figure 5B:
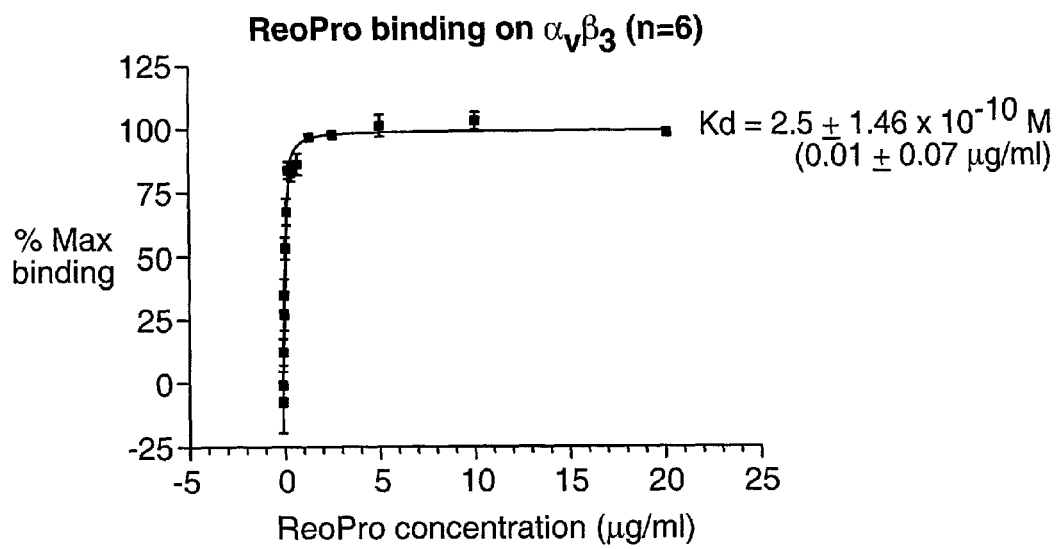
Figure 6A:
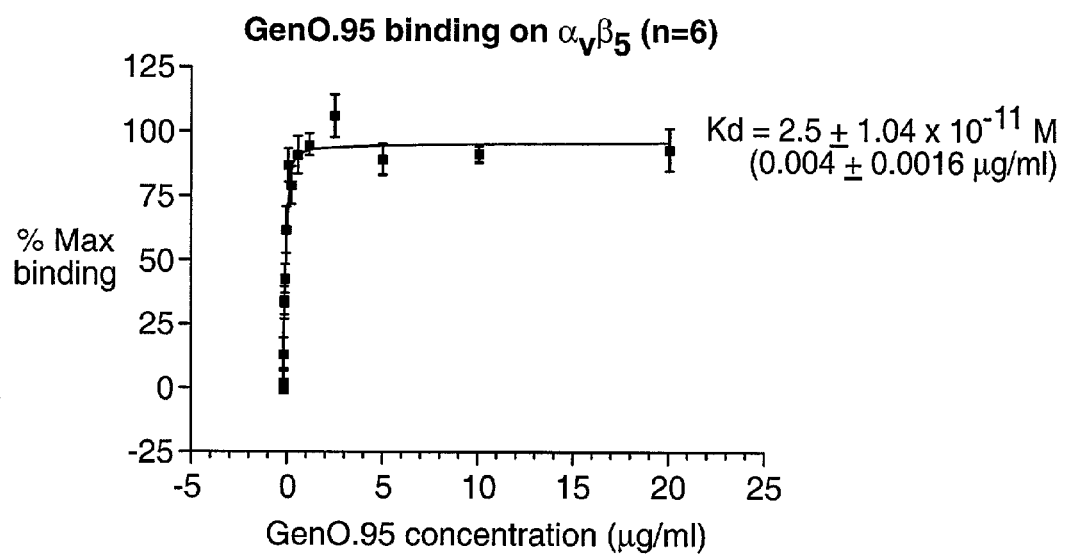
FIG. 6A–B shows a graph of saturation binding curve of GenO.95 (FIG. 5A) and ReoPro (FIG. 5B) on αvβ5 coated plates.
Figure 6B:
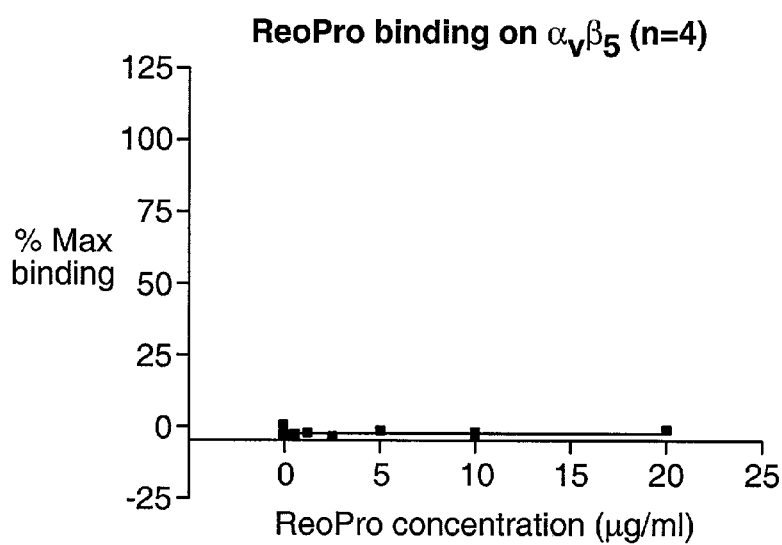

Determination of the binding affinity values was performed by measuring the binding of various concentrations of GenO.95 (and ReoPro) to purified $\alpha_v\beta_3$ and $\alpha_v\beta_5$ integrins and to cell surface receptors at equilibrium. The saturation binding curves were rectangular hyperbolas, suggesting a single receptor binding site for GenO.95 and ReoPro (FIGS. 5–6; Motulsky H, 1999). Analysis of these saturation binding data (sometimes called Scatchard experiments) were performed using a one-site hyperbola nonlinear regression fit in PRISM to obtain an affinity, Kd, and receptor number, Bmax (Motulsky H, 1999).

Several lots of GenO.95, ReoPro and purified integrins were used to ensure an accurate determination of binding affinity values. The saturation binding curve of GenO.95 on an $\alpha_v\beta_3$, coated plate (FIG. 5A) and the binding curve of ReoPro on an $\alpha_v\alpha_5$ coated plate (FIG. 5B) represent the mean and standard deviation of six separate experiments. Results obtained with Triton formulation of $\alpha_v\beta_3$ were found to be more reproducible than those obtained from the octyl formulation. On $\alpha_v\beta$ coated plates, the GenO.95 mean Kd was $2.1 \pm 1.33 \times 10^{-10}$ M; and the mean ReoPro Kd was $2.5 \pm 1.46 \times 10^{-10}$ M.

The saturation binding curve of GenO.95 on an $\alpha_v\beta_5$ coated plate (FIG. 6A) and the binding curve of ReoPro on an $\alpha_v\beta_5$ coated plate (FIG. 6B) are shown as the mean and standard deviation of six separate experiments. Results obtained with the octyl formulation were more consistent than those obtained with the Triton formulation. The GenO.95 mean Kd on $\alpha_v\beta_5$ was $2.5 \pm 1.04 \times 10^{-11}$ M. ReoPro showed no binding and no dose-response on $\alpha_v\beta_5$ coated plates.

The binding affinity values for purified integrins were compared to binding to receptors expressed on various cell lines. FIG. 7A–C shows the binding of 125-I GenO.95 with A375S2 cells which express $\alpha_v\beta_3$ and $\alpha_v\beta_5$ (FIG. 7A). Mean affinity values on A375S2 cells were: Kd=$5.2 \pm 2.04 \times 10^{-9}$ M; and $120,000 \pm 37,000$ receptors/cell. HT-29 cells express $\alpha_v\beta_5$ Affinity values for 125-I GenO.95 binding to HT-29 cells were: Kd=$1.3 \pm 3.76 \times 10^{-10}$ M; and $81,000 \pm 24,000$ receptors/cell (FIG. 7B). M21 cells express $\alpha_v\beta_3$ and $\alpha_v\beta_5$ integrins. 125-I GenO.95 binding to M21 cellls were: Kd=$8.5 \pm 3.03 \times 10^{-9}$ M; and $200,000 \pm 80,000$ receptors/cell (FIG. 7C).

Figure 8A:
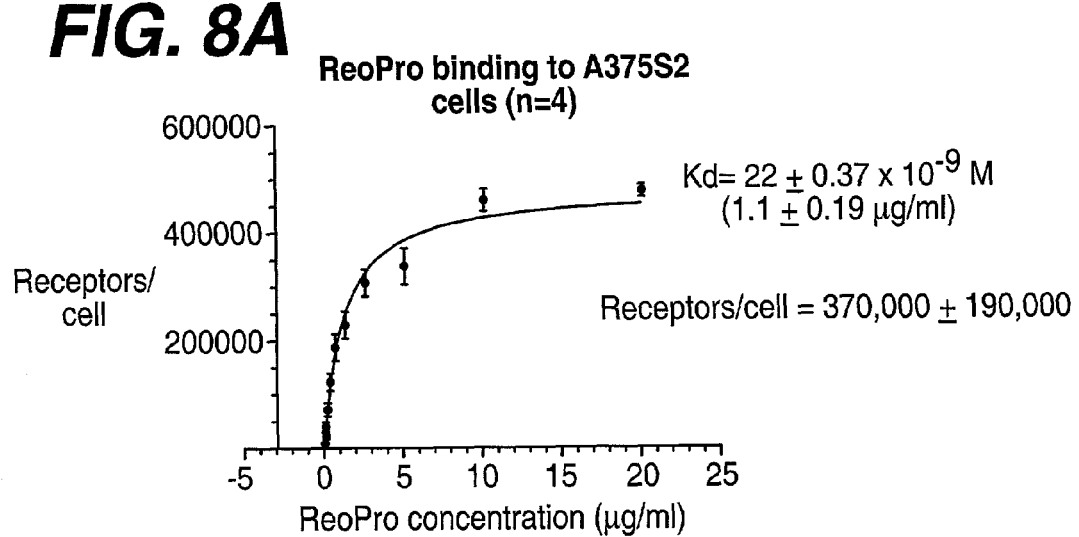
FIG. 8A–C shows saturation binding curves with graphs binding to (FIG. 8A): A375S2.
Figure 8B:
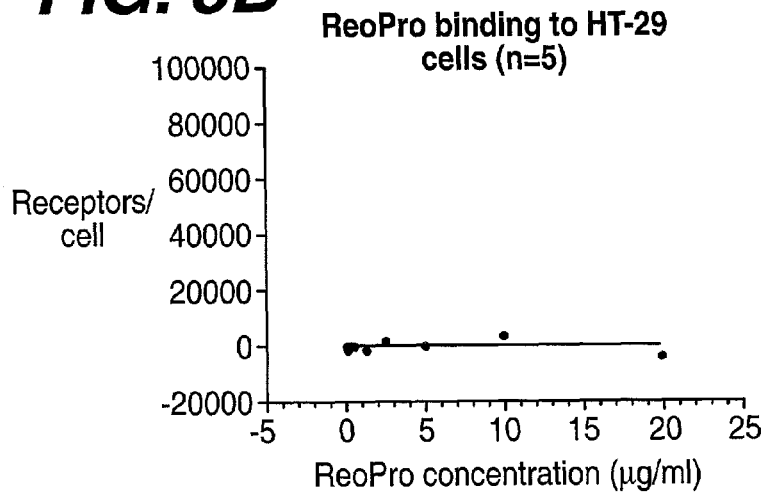
Figure 8C:
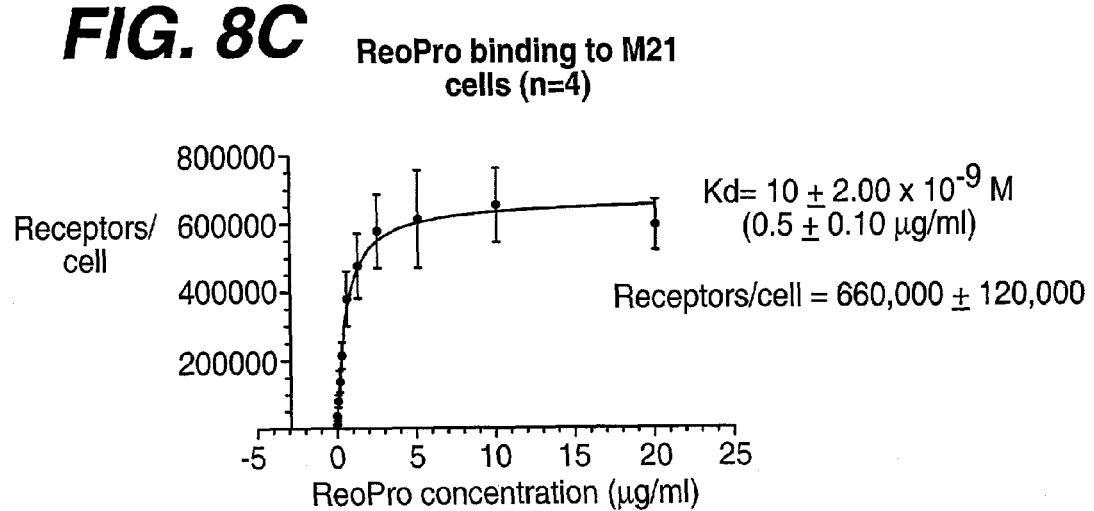

Similar cell binding studies were performed with 125-I ReoPro on various cell lines. FIG. 8A–C shows the binding of 125-I ReoPro with A375S2 cells and the mean values obtained were: Kd=$22 \pm 3.7 \times 10^{-9}$ M; and $370,000 \pm 190,000$ receptors/cell (FIG. 8A). On HT-29 cells, 125-I ReoPro showed minimal binding (FIG. 8B). 125-I ReoPro binding to M21 cells showed: Kd=$10 \pm 2.00 \times 10^{-9}$ M and $660,000 \pm 120,000$ receptors/cell (FIG. 8C). The binding values of 125-I ReoPro on M21 cells are consistent with values previously published (Tam et al, 1998).

A summary of binding results is shown in Tables 2–3.

TABLE 2

Summary of GenO.95 and ReoPro affinities to purified integrins

| | $\alpha_v\beta_3$ coated plate (n = 6) Kd (M) | $\alpha_v\beta_5$ coated plate (n = 6) Kd (M) |
|---|---|---|
| GenO.95 | $2.1 \pm 1.33 \times 10^{-10}$ | $2.5 \pm 1.04 \times 10^{-11}$ |
| ReoPro | $2.5 \pm 1.46 \times 10^{-10}$ | Negligible |

TABLE 3

Summary of GenO.95 and ReoPro affinities to cells

| | A375S2 cells Kd (M) | A375S2 cells Receptors per cell | HT-29 cells Kd (M) | HT-29 cells Receptors per cell | M21 cells Kd (M) | M21 cells Receptors Per cell |
|---|---|---|---|---|---|---|
| GenO.95 | $5.2 \pm 2.04 \times 10^{-9}$ (n = 5) | $120,000 \pm 37,000$ (n = 7) | $1.3 \pm 0.38 \times 10^{-9}$ (n = 5) | $81,000 \pm 24,000$ (n = 7) | $8.5 \pm 3.03 \times 10^{-9}$ (n = 4) | $200,000 \pm 80,000$ (n = 8) |
| ReoPro | $22 \pm 3.7 \times 10^{-9}$ (n = 3) | $370,000 \pm 190,000$ (n = 6) | Negligible (n = 4) | Negligible (n = 4) | $10 \pm 2.00 \times 10^{-9}$ (n = 3) | $660,000 \pm 120,000$ (n = 7) |
| anti $\alpha_v\beta_3$ LM609 | nd | $300,000$ (n = 2) | nd | nd | nd | nd |
| anti-$\alpha_v\beta_5$ P1F6 | nd | $70,000 \pm 50,000$ (n = 4) | nd | $73,000$ (n = 1) | nd | $44,000$ (n = 2) |

Several observations were notable in the binding characterizations. Affinity values (Kd) of GenO.95 on $\alpha_v\beta_5$ were lower than on $\alpha_v\beta_3$ Lower Kd values indicate a higher affinity; thus the affinity for GenO.95 binding to $\alpha_v\beta_5$ purified integrin was about 8-fold higher than binding to $\alpha_v\beta_3$ purified integrin. However, when both integrin receptors are present on the same cells, the overall affinity value more closely approximates the value corresponding to the integrin in greater abundance. Thus, on A375S2 and M21 cells where there is more $\alpha_v\beta_3$ than $\alpha_{v\beta5}$ the affinity of GenO.95 binding to these cells was similar to the affinity on $\alpha_v\beta_3$, $\sim 7\times 10^{-9}$ M. In contrast, on HT-29 cells which express $\alpha_v\beta_5$, the GenO.95 affinity was slightly higher, $1\times 10^{-9}$ M. The approximately 2-fold discrepancy in receptor sites per cell between GenO.95 and ReoPro binding may be explained by the difference in antibody valency. GenO.95 (IgG) is bivalent and likely binds two adjacent receptors, whereas ReoPro (Fab) is monovalent and can only bind to one receptor (BRD930001).

References

Fraker D J, Speck J C. Protein and cell membrane iodination with a sparingly soluble chloramide 1,3,4,5-tetrachloro-3a-diphenyl-glycoluril. *Biochem Biophys Res Commun.* 80:849, 1978.

Motulsky H. *Analyzing Data with GraphPad Prism.* GraphPad Software, Inc. San Diego, Calif. 1999.

Tam S H, Sassoli P M, R Jordan, M T Nakada. *Circulation,* 1999.

EXAMPLE 4

Effect of Dual Integrin Antibody on Angiogenesis Modulation

Summary

Gen095 is a human IgG1κ monoclonal antibody that recognizes integrins αvβ3 and αvβ5. These integrins participate in endothelial cell adhesion, migration, survival and proliferation, processes that are important for angiogenesis. Endothelial cell sprouting mimics angiogenesis in vitro because it involves cell adhesion, migration, proliferation and survival. We utilized the sprouting assay to determine whether Gen095 could inhibit αvβ3 and αvβ5 function. This example describes that Gen095 is an inhibitor of sprouting of endothelial cells that are cultured in three dimensional fibrin matrix, thereby demonstrating that this antibody may have potential anti-angiogenic properties.

Introduction

There is now considerable evidence that progressive tumor growth is dependent upon angiogenesis, the formation of new blood vessels. These blood vessels provide tumors with nutrients and oxygen, carry away waste products and act as conduits for the metastasis of tumor cells to distant sites (1). Recent studies have further defined various roles of integrins in the angiogenic process. Integrins are heterodimeric transmembrane proteins that play an important role in mediating cell adhesion, migration, survival, and proliferation (2). Expression of integrin αvβ3 is minimal on resting or normal blood vessels but is significantly up-regulated on angiogenic vascular cells (1–3). The closely related but distinct integrin αvβ5 has also been shown to mediate the angiogenic process. An antibody generated against αvβ3 blocked basic fibroblast growth factor (bFGF) induced angiogenesis, whereas an antibody specific to αvβ5 inhibited vascular endothelial growth factor (VEGF) induced angiogenesis (1–5).

Angiogenesis can be mimicked in vitro by an endothelial sprouting assay. This system involves endothelial cell migration and proliferation. Gen095 is a human monoclonal antibody that recognizes integrins αvβ3 and αvβ5, and these integrins regulate endothelial cell migration and proliferation. Therefore, we determined whether Gen095 could inhibit sprouting of endothelial cells. This example describes experiments that demonstrate that Gen095 inhibits sprouting of human endothelial cells growing in a fibrin matrix.

Materials

Human basic fibroblast growth factor (bFGF) and human vascular endothelial growth factor 165 ($VEGF_{165}$) were obtained from R&D Systems (Minneapolis, Minn). MAB 1976Z (LM609), a monoclonal antibody against integrin αvβ3 and MAB 1961 (PIF6), a monoclonal antibody against integrin αvβ5 were purchased from Chemicon (Temecula, Calif.). ReoPro and Gen095 were obtained from Centocor's Clinical Pharmacology and Antibody Technology Department. Human fibrinogen (plasminogen free, >95% clottable protein) and bovine skin gelatin were purchased from Sigma (Saint Louis, Mich.).

Cell Lines

Huvecs, Human umbilical vein endothelial cells, were purchased from Clonetics (Walkersville, Mass.). Huvecs were cultured in endothelial basal media (EBM) kit (Clonetics) containing 10% FBS, long R insulin-like growth factor-1, ascorbic acid, hydrocortisone, human epidermal growth factor, human vascular endothelial growth factor, hFGF-b, gentamicin sulfate, and amphotericin-B. Cells were incubated at 37° C. and 5% $CO_2$ and media was changed every 2 to 3 days. Only passages 3 to 8 were used in all experiments.

Fibrin Microcarrier-based Sprouting Assay

A modification of the methods of Nehls and Drenckhahn (6) was used to measure capillary tube formation in three-dimensional fibrin-based matrix. Gelatin-coated cytodex-3 microcarriers (MCs, Sigma) were prepared according to recommendations of the supplier. Freshly autoclaved MCs were suspended in EBM-2+20% FBS and endothelial cells were added to a final concentration of 40 cells/MC. The cells were allowed to attach to the MCs during a 4-hour incubation at 37° C. The MCs were then suspended in a large volume of medium and cultured for 2 to 4 days at 37° C. in 5% $CO_2$ atmosphere. MCs were occasionally agitated to prevent aggregation of cell coated beads. MCs were embedded in a fibrin gel that was prepared as follows: human fibrinogen (2 mg/ml) was dissolved in plain, bFGF or serum containing EBM-2 media. This solution also contained various antibodies. To prevent excess fibrinolysis by fibrin-embedded cells, aprotinin was added to the fibrinogen solution and to growth media at 200 U/ml. Cell-coated microcarriers were added to the fibrinogen solution at a density of 100 to 200 MCs/ml (50–100 beads/per well-48 well plate) and clotting was induced by addition of thrombin (0.5 U/ml). After clotting was complete, 0.5 ml solution (containing all components described above except fibrinogen and thrombin) was added to the fibrin matrices. The plates were incubated at 37° C. and 5% $CO_2$ for 1 to 3 days. After 1–3 days, gels were fixed with 3% paraformaldehyde dissolved in PBS, and the number of capillary sprouts with length exceeding the diameter of the MC bead (150 μm) was quantified.

Results and Discussion

Figure 9:
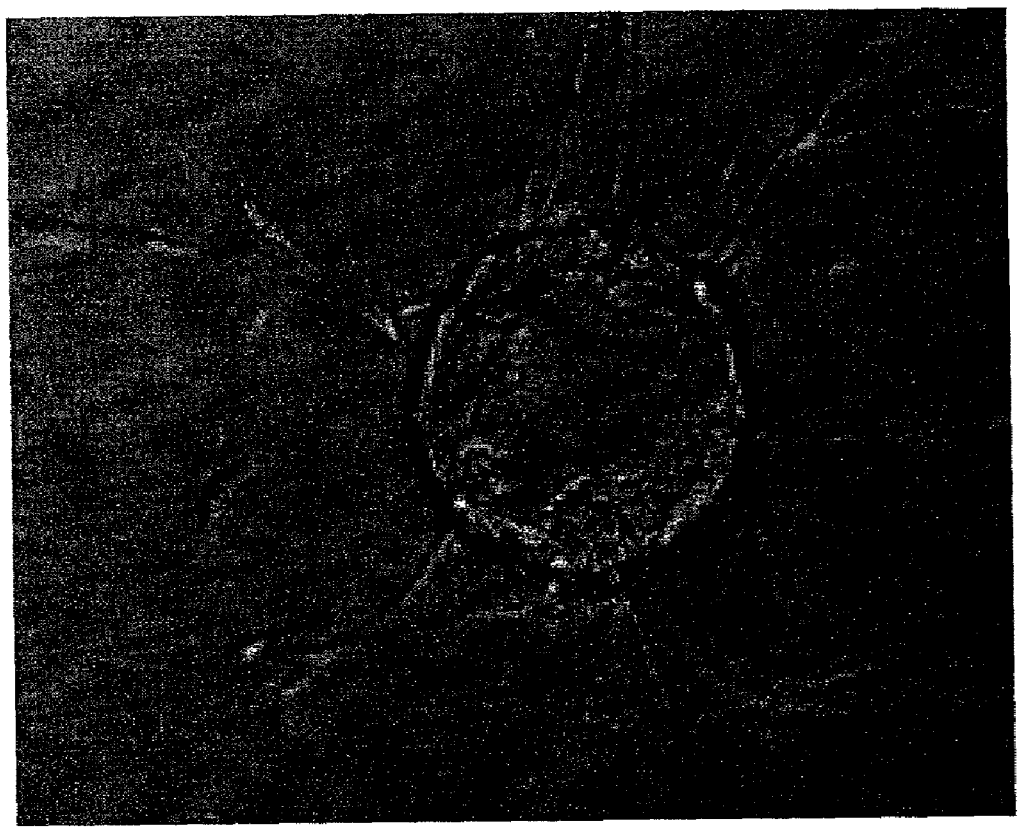
FIG. 9 shows a representation of microcapillary formation of endothelial cells from MC beads cultured in fibrin gels. Objective lens: 40×. The assay was performed as described in Methods of Example 4.
Figure 10:
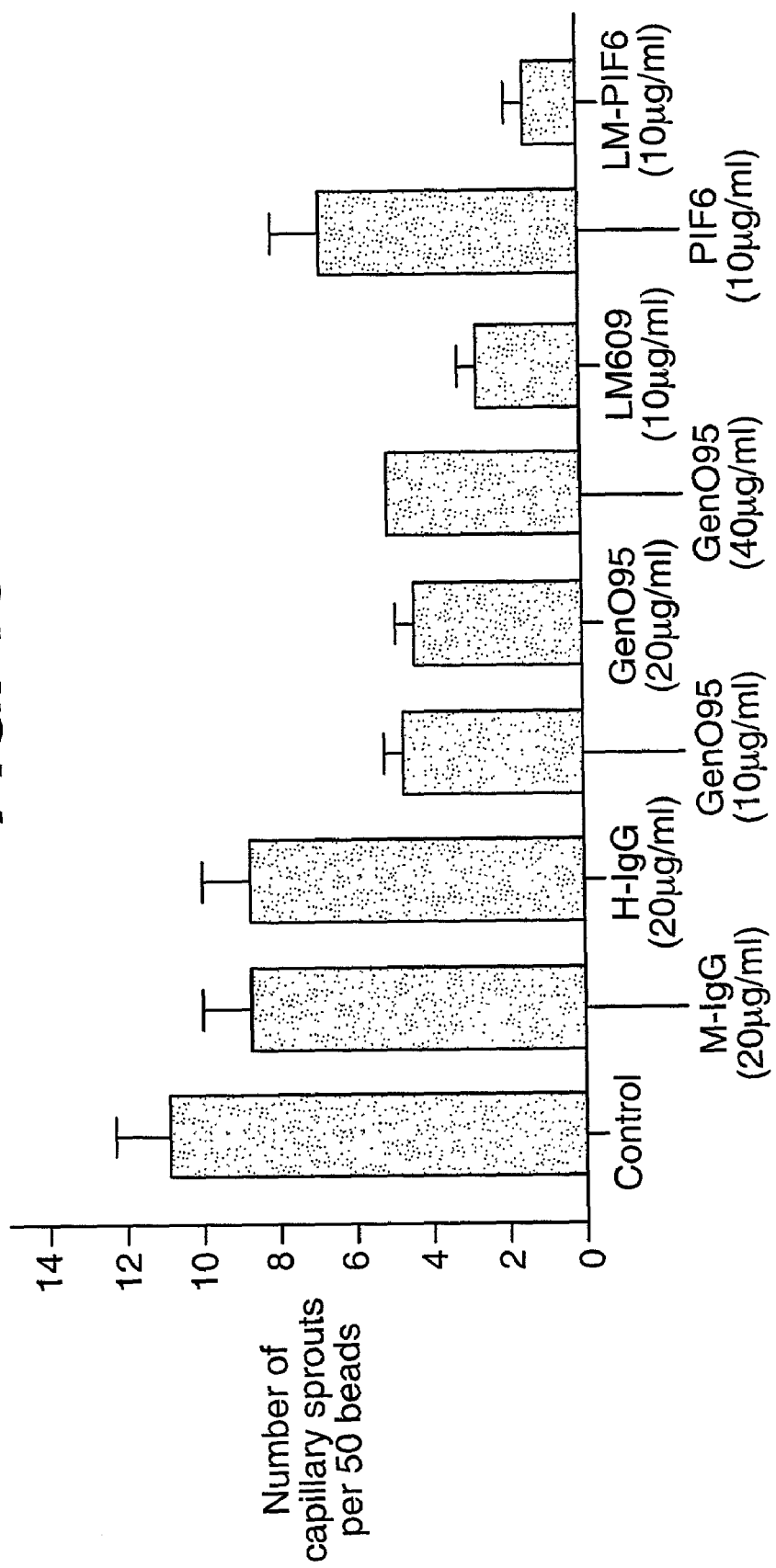
FIG. 10 shows a graph of quantification of capillary formation in a fibrin gel in media containing 30 ng/ml bFGF dissolved in 0.1% serum. The number of microcapillary sprouts were quantified as described in Methods of Example 4. Control indicates vehicle control, mouse (M) and human (H) IgG served as negative controls. LM-P1F6 is a combination of both LM609 and P1F6. Each bar represents the mean of 6 wells (+/−SD).
Figure 12A:
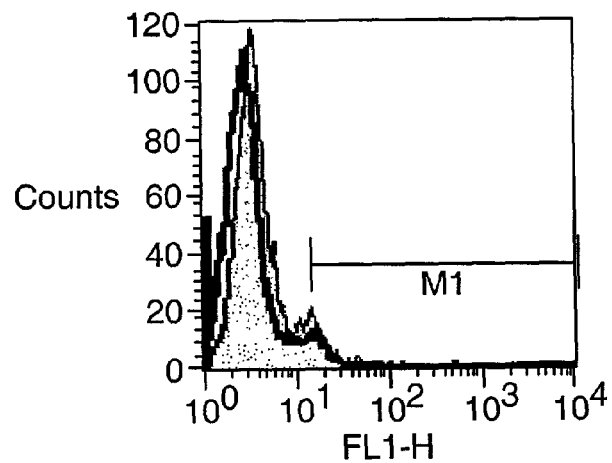
FIG. 12. HT29 cells (FIGS. 12A, B and C) express αvβ5, but not αvβ3 integrin on their surface. HUVEC (FIGS. 12D, E and F) and A375S.2 (FIGS. 12G, H and I) cells express (αvβ5 and αvβ3 integrin on their surface. Tumor cells and endothelial cells were stained by immunofluorescence and analyzed by flow cytometry. The histogram on the left represents background fluorescence in the presence of isotype matched antibody. The histogram on the right indicates positive staining. A, D, G, LM609 (mAb directed to αvβ3, 10 μg/ml); B, E, H, PIF6 (mAb directed to αvβ5, S 10 μg/ml); and C, F, I, GenO95 (10 μg/ml).
Figure 12B:
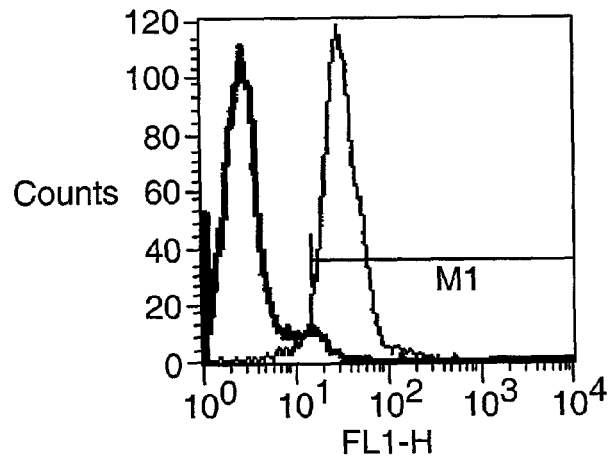
Figure 12C:
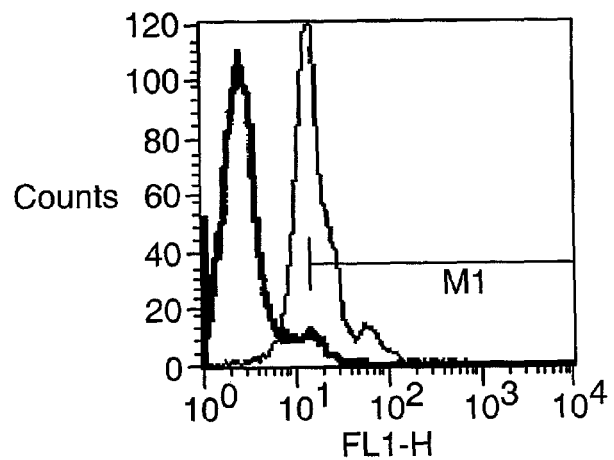
Figure 12D:
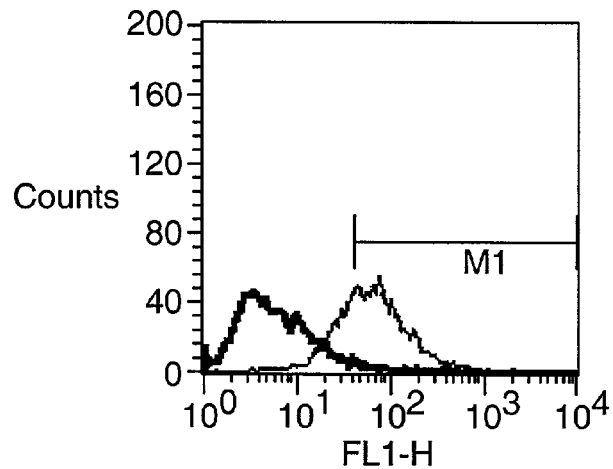
Figure 12E:
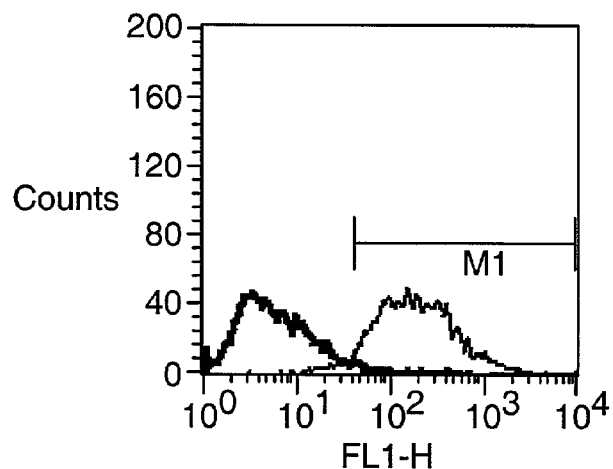
Figure 12F:
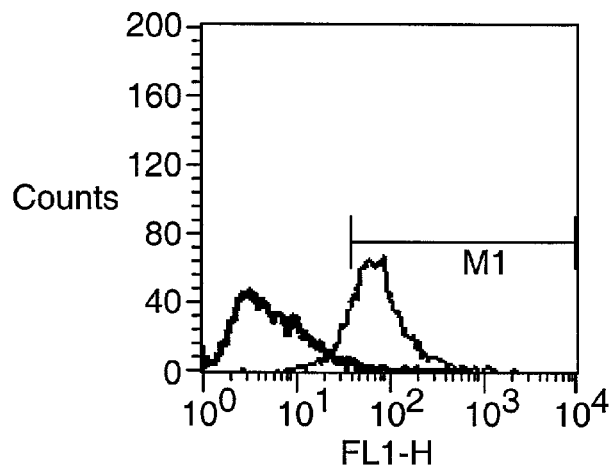
Figure 12G:
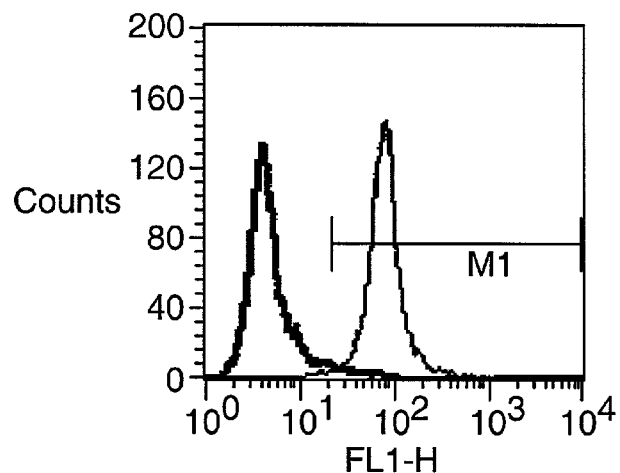
Figure 12H:
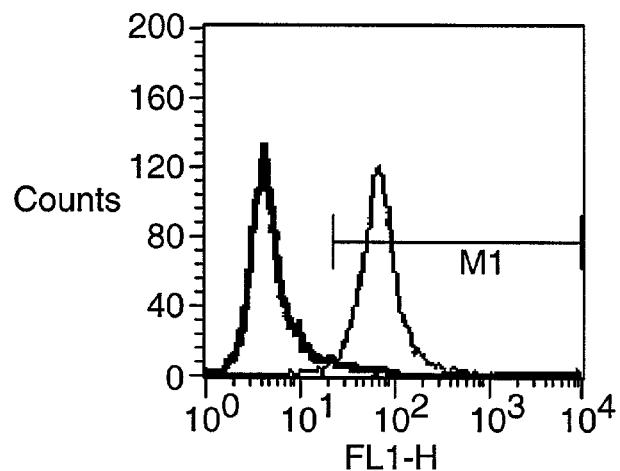
Figure 12I:
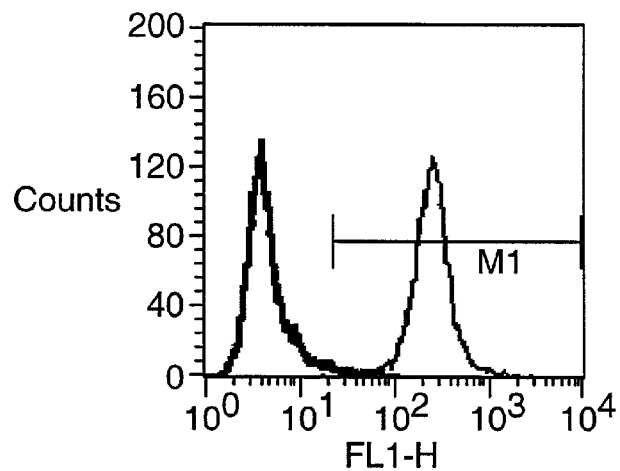

Huvecs can form capillary-like sprouts when cultured in a fibrin gel (FIG. 9). Endothelial cells migrate outwards from the gelatin coated beads and extend into long filopodia. The long sprouts consist of several cells forming a lumen. This process resembles microcapillary formation in vivo, because it involves endothelial cell migration, invasion and cell proliferation. Quantification of sprout formation revealed that Gen095 inhibited endothelial cell sprout formation in bFGF or complete media (FIG. 10). Combination of LM609 and P1F6 routinely inhibited sprouting more effectively than Gen095 (FIG. 11).

Conclusion

Formation of new blood vessels from existing blood vessels is a hallmark of angiogenesis. This process can be mimicked in vitro by the endothelial sprouting assay. These sprouts represent microcapillaries that are formed in response to angiogenic stimuli such as bFGF or a variety of stimuli that are present in serum. Gen095 dose dependently inhibited bFGF- and complete media-stimulated endothelial cell sprouting, suggesting that this antibody can effectively inhibit $\alpha v\beta 3$ and $\alpha v\beta 5$ function. Why Gen095 was not as effective as the combination of LM609 and P1F6 is unknown, but it is possible that Gen095 recognizes $\alpha v\beta 3$ and $\alpha v\beta 5$ with lower affinity when compared to LM609 and P1F6, respectively. Collectively, these data demonstrate that Gen095 can inhibit the complex process of microcapillary formation in vitro.

References

1. Gastl G, Hermann T, Steurer M, Zmija J, Gunsilius E, Unger C, and Kraft A. 1997. Angiogenesis as a Target for Tumor Treatment. *Oncology* 54:177–184.
2. Eliceiri B P, and Cheresh D A. 1999. The role of $\alpha V$ integrins during angiogenesis: insights into potential mechanisms of action and clinical development. *The Journal of Clinical Investigation* 103:1227–1230.
3. Brooks P C, Montgomery A M, Rosenfeld M, Reisfeld R A, 1994. Integrin $\alpha v\beta 3$ antagonists promote tumor regression by inducing apoptosis of angiogenic blood vessels. *Cell* 79: 1157–1164.
4. Enenstein J, Walweh N S, and Kramer R H. 1992. Basic FGF and TGF-$\beta$ differentially modulate integrin expression of human microvascular endothelial cells. *Exp. Cell Res.* 203:499–503.
5. Friedlander M, Brooks P C, Shaffer R W, Kincaid C M, Varner J A, and Cheresh D A. 1995. Definition of two angiogenic pathways by distinct $\alpha V$ integrins. *Science* 270:1500–1502.
6. Nehls, V and Drenckhahn, D. 1995. A novel, microcarrier-based in vitro assay for rapid and reliable quantification of three-dimensional cell migration and angiogenesis. *Microvascular Res.* 50:311–322.

EXAMPLE 5

Effect of Dual Integrin Antibody on Endothelial and Tumor Cell Adhesion, Mirgration and Invasion Summary (CBA/J×C57/BL6/J) $F_2$ hybrid mice (1–4) containing human variable and constant region antibody transgenes for both heavy and light chains were immunized with human placental $\alpha V\beta 3$. One fusion yielded a totally human $\alpha V\beta 3$ reactive IgG1κ monoclonal antibody named Gen095. The totally human antibody was found to be reactive to the $\alpha V\beta 3$ and $\alpha V\beta 5$ integrins (5). These integrins participate in endothelial and tumor cell adhesion, migration, and invasion. Therefore, we characterized the effect of Gen095 on integrin mediated cell motility. Gen095 inhibits human umbilical vein endothelial (HUVEC) and human melanoma cell binding to vitronectin, denatured collagen, fibrinogen and fibrin, but it does not block cell adhesion to fibronectin and type I collagen. Gen095 also inhibits migration of endothelial cells that have been stimulated with basic fibroblast growth factor and low-dose serum. Gen095 inhibits invasion of tumor cells through a fibrin gel. In conclusion, Gen095 functionally blocks $\alpha V\beta 3$ and $\alpha V\beta 5$ in a variety of cell-based assays in vitro.

Abbreviations

BSA—bovine serum albumin
$CO_2$—carbon dioxide
DMSO—dimethyl sulfoxide
FBS—fetal bovine serum
Ig—immunoglobulin
Mab—monoclonal antibody
OD—optical density
RT—room temperature
HUVECS—human umbilical vein endothelial cells
bFGF—bovine basic fibroblast growth factor Introduction There is now considerable evidence that progressive tumor growth is dependent upon angiogenesis. The formation of new blood vessels provide tumors with nutrients and oxygen, carry away waste products and act as conduits for the spread of tumor cells to distant sites. Several studies have defined the role of integrins in the angiogenic process. Integrins are heterodimeric trans-membrane proteins that play a critical role in cell adhesion to the extracellular matrix (ECM) and mediate cell survival, proliferation and migration (6). During the angiogenic process, $\alpha v\beta 3$ and $\alpha v\beta 5$ are upregulated on the surface of activated endothelial cells, which in turn helps these cells to migrate and proliferate (6). An antibody generated against $\alpha V\beta 3$ blocks basic fibroblast growth factor (bFGF) induced angiogenesis, whereas an antibody specific to $\alpha V\beta 5$ inhibits vascular endothelial growth factor (VEGF) induced angiogenesis (6,7). In addition to regulating angiogenesis, $\alpha V\beta 5$ and $\alpha V\beta 3$ regulate tumor cell adhesion, migration and invasion, processes required for tumor cell metastases. Previous studies indicated that Gen095 binds to purified $\alpha V\beta 5$ and $\alpha V\beta 3$ integrins, therefore, we determined whether this antibody could functionally block $\alpha V\beta 3$- and $\alpha V\beta 5$-mediated endothelial and tumor cell adhesion, migration and invasion.

Materials and Methods

Materials

Bovine fibroblast growth factor (bFGF) and human vascular endothelial growth factor 165 ($VEGF_{165}$) were obtained from R&D Systems (Minneapolis, Minn.). MAB 1976Z (LM609), a monoclonal antibody against integrin $\alpha v\beta 3$ and MAB1961 (PIF6), a monoclonal antibody against integrin $\alpha v\beta 5$ were purchased from Chemicon (Temecula, Calif.). ReoPro (lot: 94A04ZE) and Gen095 (lot: JG100899) were obtained from Centocor. BIOCOAT cell culture inserts (pore size: 8 μm) were purchased from Becton Dickinson (Bedford, Mass.). Vybrant™ cell adhesion assay kit (V-13181) was purchased from Molecular Probes (Eugene, Oreg.). Human plasminogen free fibrinogen (VWF/Fn depleted) was purchased from Enzyme Research Labs (South Bend, Ind.). Bovine skin gelatin was purchased from Sigma (Saint Louis, Mo.). Human vitronectin was purchased from Promega (Madison, Wis.), and type I collagen was purchased from GIBCO BRL (Gaithersburg, Md.).

Cell Lines

Human umbilical vein endothelial cells (HUVECS), were purchased from Clonetics (Walkersville, Mass.), and they were cultured in EBM medium kit (Clonetics) containing 10% FBS, long R insulin-like growth factor-1, ascorbic acid, hydrocortisone, human epidermal growth factor, human vascular endothelial growth factor, gentamicin sulfate and amphotericin-B. Cells were grown at 37° C. and 5% $CO_2$ and media was changed every 2 to 3 days. Cells were passaged when they reached 80% confluence. Passages 3 to 8 were used in all experiments.

The A375S.2 human melanoma cell line expressing the $\alpha V\beta 3$ and $\alpha V\beta 5$ integrins was obtained from Centocor Cell Bank where the cell line was deemed free of mycoplasma and bacterial contaminants. The cells were cultured in DMEM medium supplemented with 10% FBS, 2 mM L-glutamine, 1 mM sodium pyruvate, and 0.1 mM non-essential amino acids.

Human colon carcinoma HT29 cells were obtained from Centocor Cell Biology Service Department, where the cell line was deemed free of mycoplasma and bacterial contaminant. The cells were cultured in ($\alpha$-MEM medium supplemented with 10% FBS, 2 mM L-glutamine, 1 mM sodium pyruvate, and 0.1 mM nonessential amino acids.

Flow Cytometry

For the detection of surface integrins, cells were harvested, rinsed, suspended in unsupplemented RPMI media, and sequentially incubated for 60 minutes on ice with anti-integrin mAb (10 μg/ml) and FITC-labeled goat anti-mouse antibody (1:100) or FITC-labeled anti-integrin antibody (10 μg/ml). Absence of primary antibody or substitution of primary antibody with isotype matched antibody served as negative controls. Cells were immediately analyzed with a FACS Scan II flow cytometer (Becton Dickinson, Mountain View, Calif.).

Adhesion Assay

Microtiter plates (Linbro-Titertek, ICN Biomedicals, Inc) were coated at 4° C. overnight with vitronectin (1 μg/ml), gelatin (0.1%), fibrinogen (100 μg/ml), type I collagen (10 μg/ml), or fibronectin (10 μg/ml). Immediately before use plates were rinsed with PBS and blocked for 1 hour with 1% BSA/PBS (pH 7.4). Fibrin-coated Microtiter wells were formed by thrombin treatment (1 U/ml) of fibrinogen. Adherent cells (HUVECS HT29 and A375S.2) were labeled with Calcein AM fluorescent dye (Molecular Probes, Eugene, Oreg.) according to the manufacturer's instructions, harvested, washed twice, and suspended in 0.1% BSA in DMEM medium. After cell density was adjusted to $5 \times 10^5$/ml, cells were incubated with various concentrations of antibodies for 15 min at 37° C. The cell-antibody mixture was added to wells (100 μl per well) and incubated for 1 h at 37° C. Plates were rinsed twice with PBS to remove unbound cells and adhesion was measured in a fluorescence plate reader (Fluoroskan) at 485–538 nm. Cell adhesion to BSA-coated wells served as a negative control. Isotype matched antibodies served as a negative control.

Chemotactic Migration Assay

Cell migration assays were performed in 24-Transwell chambers with a polystyrene membrane (6.5 mm diameter, 10 μm thickness, and a pore size of 8 μm). Sub-confluent 24-hr cell cultures (HUVECS or A375S.2) were harvested with trypsin-EDTA, washed twice, and resuspended in their respective serum free medium containing 0.1% BSA. Cells (100,000/500 μl) were added to the upper chamber in the presence or absence of antibodies. To facilitate chemotactic cell migration, 750 μl of medium containing 0.1% BSA and vitronectin (2 μg/ml) or serum (2% for HUVECS and 10% for A375S2 cells) was added to the bottom chambers and the plate was placed in a tissue culture incubator. Migration was terminated after 4 to 8 hrs by removing the cells on the top with a cotton swab and then the filters were fixed with 3% paraformaldehyde and stained with Crystal Violet. The extent of cell migration was determined by light microscopy and images were analyzed using the Phase 3 image analysis software (Glen Mills, Pa.). The software analyzes the total area occupied by the stained cells on the bottom side of the filter and this is directly proportional to the extent of cell migration.

Haptotactic Migration Assay

Cell migration assays were performed using the transwell chambers as described above with slight modifications. Briefly, the underside of the membrane was coated with vitronectin (2 μg/ml) for 60 minutes at room temperature, and then blocked with a solution of 1% BSA/PBS at room temperature for 60 min. Next, membranes were washed with PBS and air dried. Serum free medium (750 μl) containing 0.1% BSA and bFGF (20 ng/ml) was added to the lower chambers. Sub-confluent 24 h cultures were harvested with trypsin-EDTA, washed twice, and resuspended in serum free medium. Cells (100,000/500 μl) were added to the upper chambers in the presence or absence of antibodies. The chambers were placed in a tissue culture incubator and migration was allowed to proceed for 6 h. Extent of cell migration was determined as described above.

Invasion Assay

Fibrinogen (Plasminogen-free, 100 μl of 10 mg/ml) and 100 μl of 1 U/ml thrombin was mixed and immediately added to the top chamber of 24 well transwell plates (6.5 mm diameter, 10 μm thickness and a pore size of 8.0 μm, Costar). The plates were incubated at 37° C. for 30 minutes to form a fibrin gel. Confluent tumor cells (A375S.2) were trypsinized, centrifuged, resuspended in basal medium supplemented with 0.1% BSA and 10 μg/ml plasminogen (Enzyme Research Labs, South Bend, Ind.) with various concentrations of antibodies, and incubated for 15 minutes at room temperature. Cells (100,000/500 μl) were added to the upper chamber in the presence or absence of antibodies. The lower compartment of the invasion chamber was filled with 0.75 ml of 10% FBS-DMEM, which served as a chemoattractant and the plate was transferred to a tissue culture incubator. After 24 hours, invasion was terminated by removing the cells on the top with a cotton swab, and the filters were fixed with 3% paraformaldehyde and stained with Crystal Violet. The extent of cell migration was analyzed using the Phase 3 image analysis software as described above.

Results and Discussion

Gen095 Inhibits αvβ3- and αvβ5-mediated Cell Adhesion

Since Gen095 binds to αVβ3 and αVβ5 integrins, we determined whether our tumor cells (A375S.2 and HT29) and endothelial cells express these integrins. Flow cytometry indicated that A375S.2 and HUVEC cells express both αVβ3 and αVβ5 integrins, but HT29 cells express αVβ5, but not αVβ3 integrin (FIG. 12A–I).

HT29 cells (12A, B and C) express αvβ5, but not αvβ3 integrin on their surface. HUVEC (12D, E and F) and A375S.2 (12G, H and I) cells express αvβ5 and αvβ3 integrin on their surface. Tumor cells and endothelial cells were stained by immunofluorescence and analyzed by flow cytometry. The histogram on the left represents background fluorescence in the presence of isotype matched antibody. The histogram on the right indicates positive staining. A, D, G, LM609 (mAb directed to αvβ3, 10 μg/ml); B, E, H, PIF6 (mnAb directed to αvβ5, 10 μg/ml); and C, F, I, Gen095 (10 μg/ml).

The effect of Gen095 on adhesion of HUVEC, A375S.2 and HT 29 cells to various matrix proteins was determined in detail. Gen095 completely inhibited adhesion of HUVEC and A375S.2 cells to vitronectin, and partially to fibrinogen, gelatin and fibrin coated plates, indicating that the antibody can block αVβ3 and αVβ5 (FIGS. 2 and 3, Table 1 and 2). Gen095 completely inhibited HT-29 cell adhesion to vitronectin coated plates, indicating that the antibody blocks αVβ5 (FIG. 4). Gen095 completely inhibited adhesion of HUVEC anid A375S.2 cells to vitronectin coated plates, indicating that the antibody blocks αVβ3 and αVβ5 (FIGS. 2 and 3). Data were graphed as percent of maximal binding (no antibody) and non-linear regression performed using GraphPad Prism.

Figure 13:
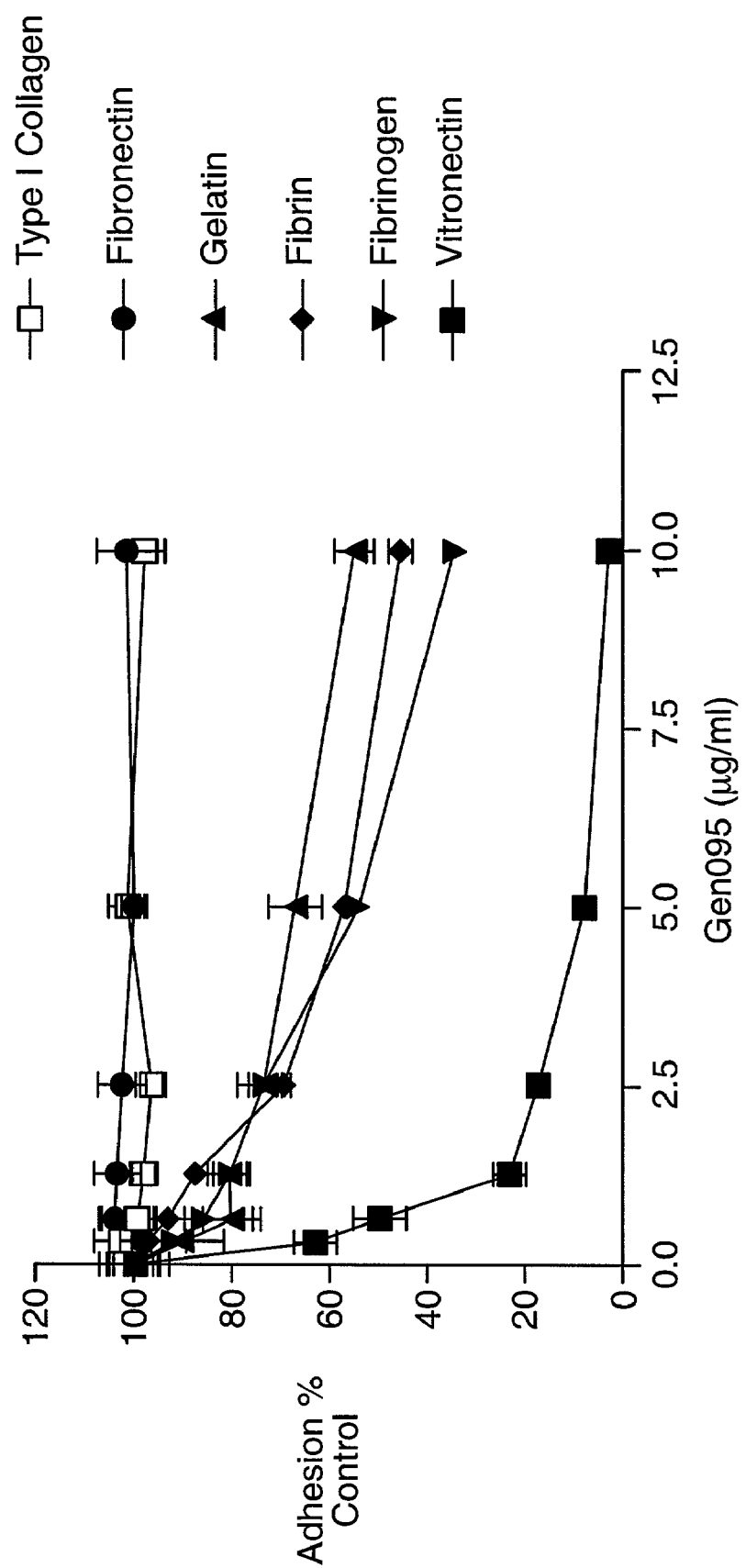
FIG. 13. Adhesion of HUVECS to matrix protein-coated plates. Adhesion assay was performed as described in Methods of Example 5. Plate was read on a fluorometer at 485–538 nm. Cell adhesion to BSA coated wells served as a negative control.

Adhesion of HUVECS to matrix protein-coated plates. Adhesion assay was performed as described in Methods. Plate was read on a fluorometer at 485–538 nm. Cell adhesion to BSA coated wells served as a negative control. In FIG. 13, the extent of cell adhesion in the presence of various concentrations of antibody was plotted as a percent of cell adhesion in the absence of antibody that was considered as 100%. Each data point is the mean of triplicate determinations (+/−SD).

Figure 14:
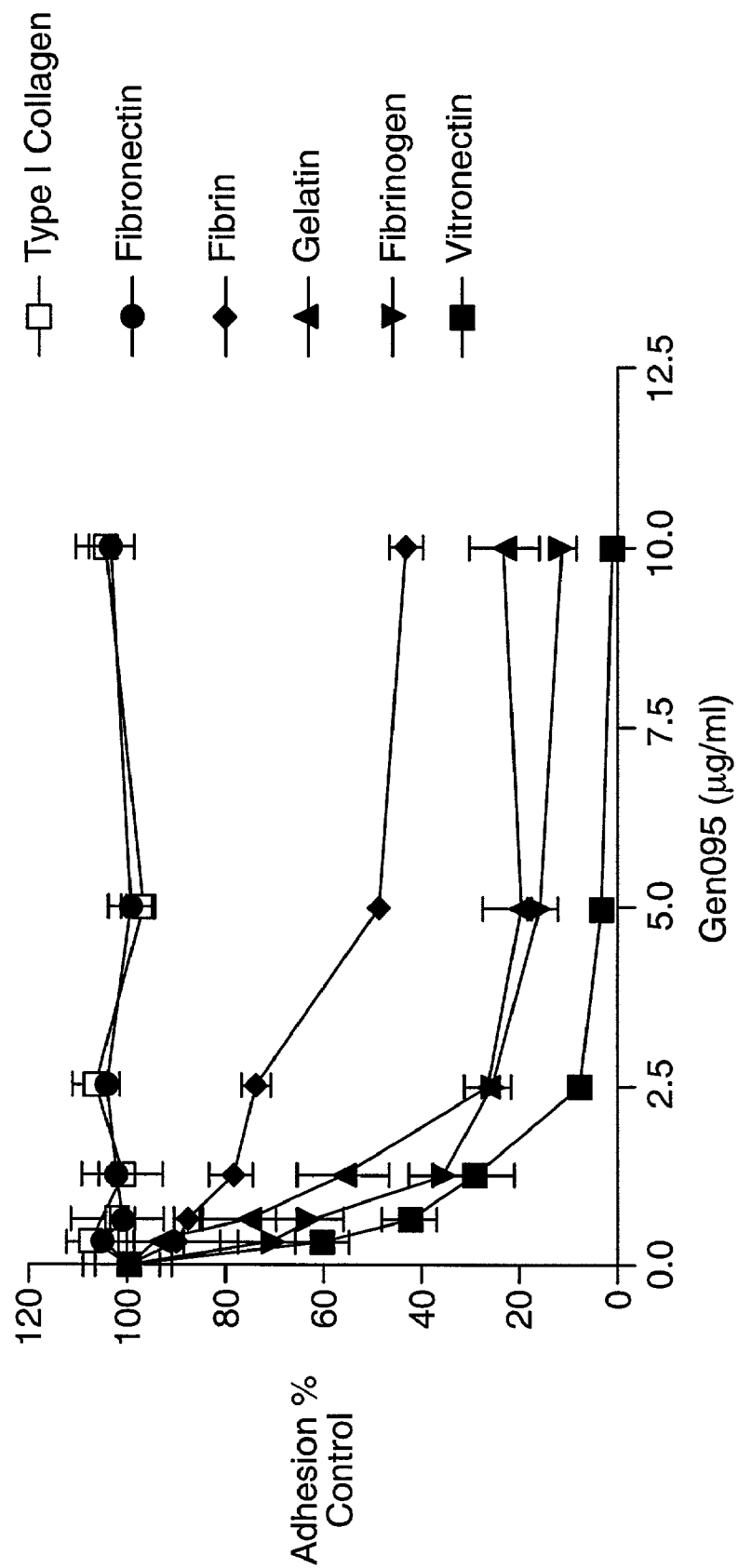
FIG. 14. Adhesion of human melanoma cells to matrix protein-coated plates. Adhesion assay was performed as described in Methods. Cell adhesion to BSA coated wells served as a negative control.

Adhesion of human melanoma cells to matrix protein-coated plates. Adhesion assay was performed as described in Methods. Cell adhesion to BSA coated wells served as a negative control. In FIG. 14 the extent of cell adhesion in the presence of various concentrations of antibody was plotted as a percent of cell adhesion in the absence of antibody that was considered as 100%. Each data point is the mean of triplicate determinations (+/−SD).

Table 4. Adhesion of HUVECs to vitronectin, gelatin, fibrinogen, fibrin, fibronectin and type I collagen. Extent of cell adhesion in the presence of various concentration of antibody was plotted as a percent of cell adhesion in the absence of antibody that was considered as 100%. Each data point is the mean of triplicate determinations (+/−SD). The concentration of antibodies used was 10 μg/ml.

| | Adhesion (%) +/− SD | | | | | |
|---|---|---|---|---|---|---|
| | Vitronectin | Gelatin | Fibrinogen | Fibrin | Fibronectin | Type I collagen |
| Human IgG | 96.3 ± 11.4 | 109.0 ± 8.8 | 108.0 ± 6.3 | 99.7 ± 4.5 | 96.8 ± 4.7 | 99.3 ± 4.1 |
| LM609 | 26.3 ± 3.7 | 36.5 ± 4.7 | 14.3 ± 2.5 | 48.1 ± 1.5 | 102.8 ± 7.2 | 108.8 ± 12.7 |
| PIF6 | 39.8 ± 5.9 | 94.4 ± 15.1 | 94.5 ± 4.2 | 96.7 ± 4.5 | 103.2 ± 3.8 | 115.7 ± 8.1 |
| LM609-PIF6 | 3.7 ± 0.4 | 32.2 ± 5.2 | 10.7 ± 1.1 | 30.7 ± 8.9 | 99.6 ± 4.7 | 116.2 ± 4.1 |
| Gen095 | 3.3 ± 0.6 | 54.8 ± 4.0 | 34.5 ± 1.7 | 45.1 ± 2.4 | 101.6 ± 6.1 | 97.7 ± 3.9 |
| ReoPro | 54.9 ± 0.9 | 2.5 ± 2.3 | 8.7 ± 2.9 | 35.8 ± 3.0 | 96.3 ± 2.8 | 99.6 ± 6.0 |

Table 5. Adhesion of A375S.2 cells to vitronectin, gelatin, fibrinogen, fibrin, fibronectin and type I collagen. Extent of cell adhesion in the presence of various concentration of antibody was plotted as a percent of cell adhesion in the absence of antibody that was considered as 100%. Each data point is the mean of triplicate determinations (+/−SD). The concentration of antibodies used is 10 μg/ml.

| | Adhesion (%) +/− SD | | | | | |
|---|---|---|---|---|---|---|
| | Vitronectin | Gelatin | Fibrinogen | Fibrin | Fibronectin | Type I collagen |
| Human IgG | 104.0 ± 5.3 | 94.6 ± 12.4 | 102.5 ± 5.9 | 99.5 ± 4.0 | 100.0 ± 5.5 | 99.1 ± 3.3 |
| LM609 | 42.1 ± 6.1 | 25.2 ± 7.1 | 14.0 ± 1.8 | 50.0 ± 1.9 | 104.0 ± 8.1 | 100.0 ± 1.5 |
| PIF6 | 28.5 ± 3.8 | 87.4 ± 7.8 | 99.4 ± 3.6 | 92.9 ± 4.7 | 101.0 ± 5.7 | 101.0 ± 7.3 |
| LM609-PIF6 | 0.9 ± 0.3 | 1.1 ± 1.5 | 10.3 ± 2.6 | 47.6 ± 3.2 | 109.0 ± 4.1 | 102.0 ± 4.6 |
| Gen095 | 1.4 ± 0.4 | 23.2 ± 7.2 | 11.4 ± 2.8 | 43.3 ± 3.5 | 103.0 ± 4.5 | 104.0 ± 5.9 |
| ReoPro | 38.1 ± 0.7 | 6.0 ± 1.0 | 6.5 ± 2.1 | 12.9 ± 3.8 | 104.0 ± 5.6 | 93.1 ± 3.1 |

Adhesion of human colon carcinoma HT29 cells to vitronectin. The adhesion assay was performed as described in Methods. Cell adhesion to BSA coated wells served as a negative control. Data in FIG. 15 are plotted as percent of maximum binding (absence of antibody), and are the mean of triplicate determinations (+/−SD).

Gen095 Blocks Human Melanoma and Endothelial Cell Migration

Integrins αVβ3 and αVβ5 participate in cell migration, therefore we determined whether Gen095 could block vitronectin-stimulated cell migration. Vitronectin-stimulated cell migration involves αVβ3 and αVβ5. Gen095 dose dependently inhibited endothelial cell migration when vitronectin was used as a chemoattractant (FIGS. 5 & 6). Interestingly, Gen095 also inhibited migration of both HUVECS and A375S.2 cells to serum (FIGS. 7–8). These findings could be potentially important for angiogenic and tumor therapy because they suggest that the targets for Gen095, αVβ3 and αVβ5, are central receptors that are activated by a variety of migratory factors that are present in serum.

Migration of HUVECS toward 2 µg/ml vitronectin. The assay was performed as described in Methods and cells were allowed to migrate for 6 h. Photomicrographs are representative fields (10× objective lens) of cell migration in FIG. 16A, absence of antibody, (16B), Gen095 (5 µg/ml), (16C), Gen095 (40 µg/ml). FIG. 16D is graphical representation of cell migration in the presence of varying concentrations of Gen095. The data were normalized to percent of control (no antibody) which was considered as 100%, and each point is the mean of three transwell filters (+/−SD).

Figure 17:
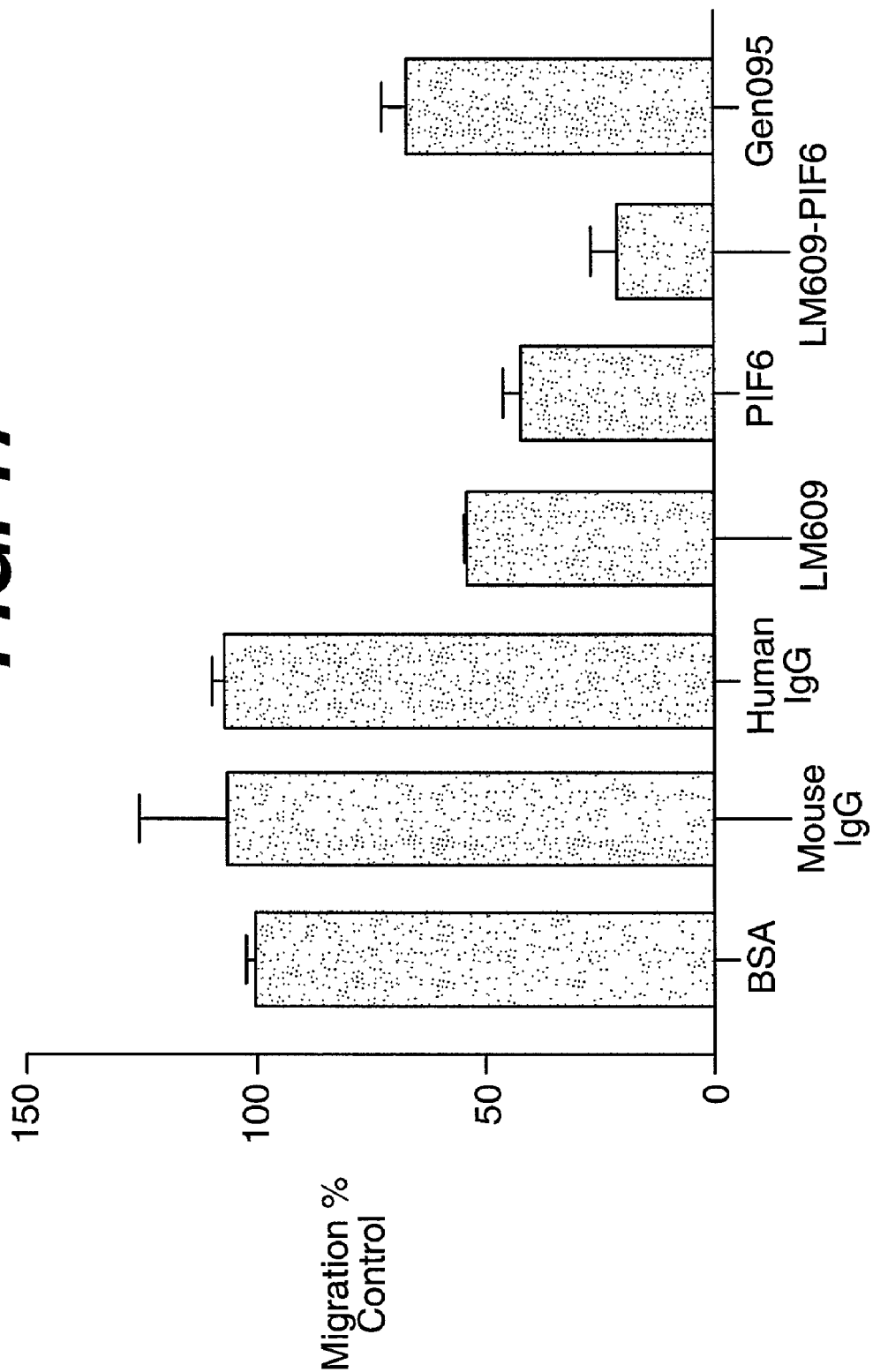
FIG. 17. Migration of HUVECS toward 2 μg/ml vitronectin in the presence of antibodies to αvβ3 and αvβ5. The migration assay was performed as described in Methods, and cells were allowed to migrate for 6 hours. LM609 and P1F6 are mAbs directed to αvβ3 and αvβ5, respectively. The data shown in FIG. 17 were normalized to percent of control (no antibody) which was considered as 100%, and each bar is the mean of three transwell filters (+/−SD). BSA, mouse IgG and human IgG served as negative controls. LM609-PIF6 represents combinations of both antibodies. The antibodies and BSA were used at a concentration of 10 μg/ml.

Migration of HUVECS toward 2 µg/ml vitronectin in the presence of antibodies to αvβ3 and αvβ5. The migration assay was performed as described in Methods, and cells were allowed to migrate for 6 hours. LM609 and P1F6 are mAbs directed to αvβ3 and αvβ5, respectively. The data shown in FIG. 17 were riormalized to percent of control (no antibody) which was considered as 100%, and each bar is the mean of three transwell filters (+/−SD). BSA, mouse IgG and human IgG served as negative controls. LM609-PlF6 represents combinations of both antibodies. The antibodies and BSA were used at a concentration of 10 µg/ml.

Figure 18A:
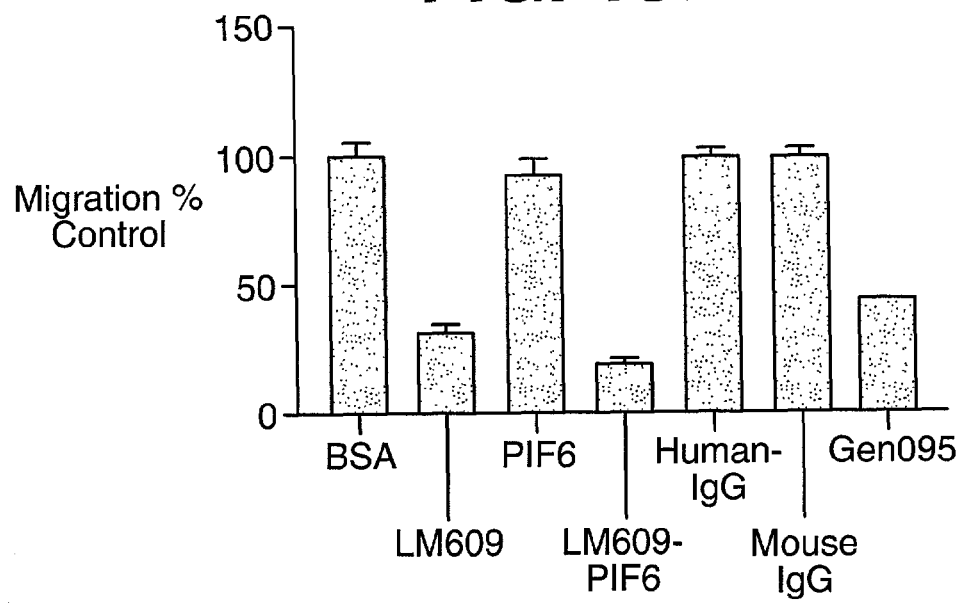
FIG. 18A–E. Migration of HUVECS towards 2% FBS. Migration assay was allowed to proceed for 4 h and the data was captured as described in Methods.
Figure 18B:
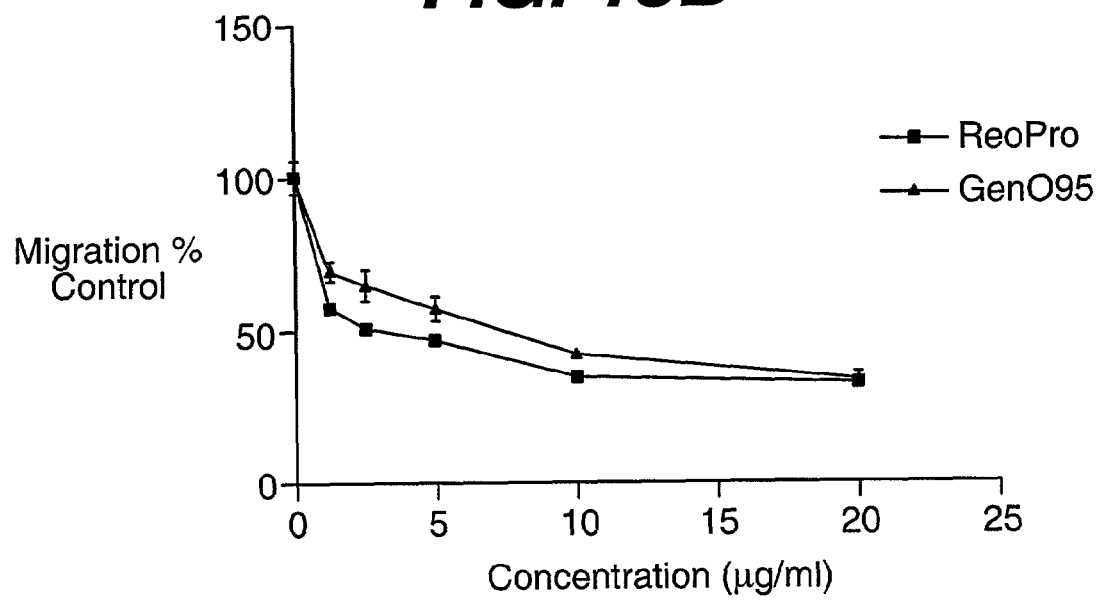
Figure 18C:
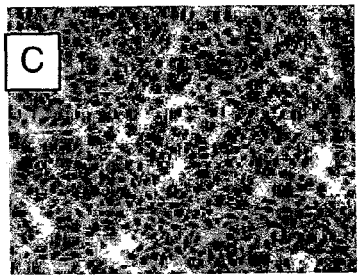
Figure 18D:
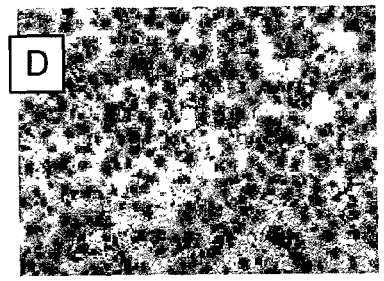
Figure 18E:
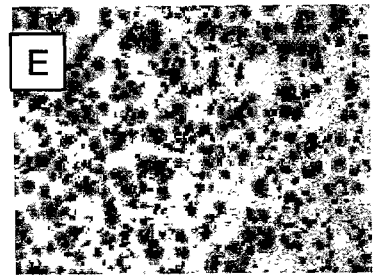

Migration of HUVECS towards 2% FBS. Migration assay was allowed to proceed for 4 h and the data was captured as described in Methods. FIG. 18(A) is a graphical representation of cell migration in the presence of LM609, P1F6, combination of LM609+P1F6, isotype matched control antibodies (human and mouse). The antibodies and proteins were used at a concentration of 10 µg/ml. FIG. 18(B) is a graphical representation of cell migration in the presence of ReoPro and Gen095. Photomicrographs are representative fields (10× objective lens) of cell migration in FIG. 18(C), the absence of antibody, FIG. 18(D), Gen095 (5 µg/ml), and FIG. 18(E), Gen095 (20 µg/ml). The data were normalized to percent of control (no antibody) which was considered as 100%, and each point is the mean of three transwell filters (+/−SD).

Figure 19A:
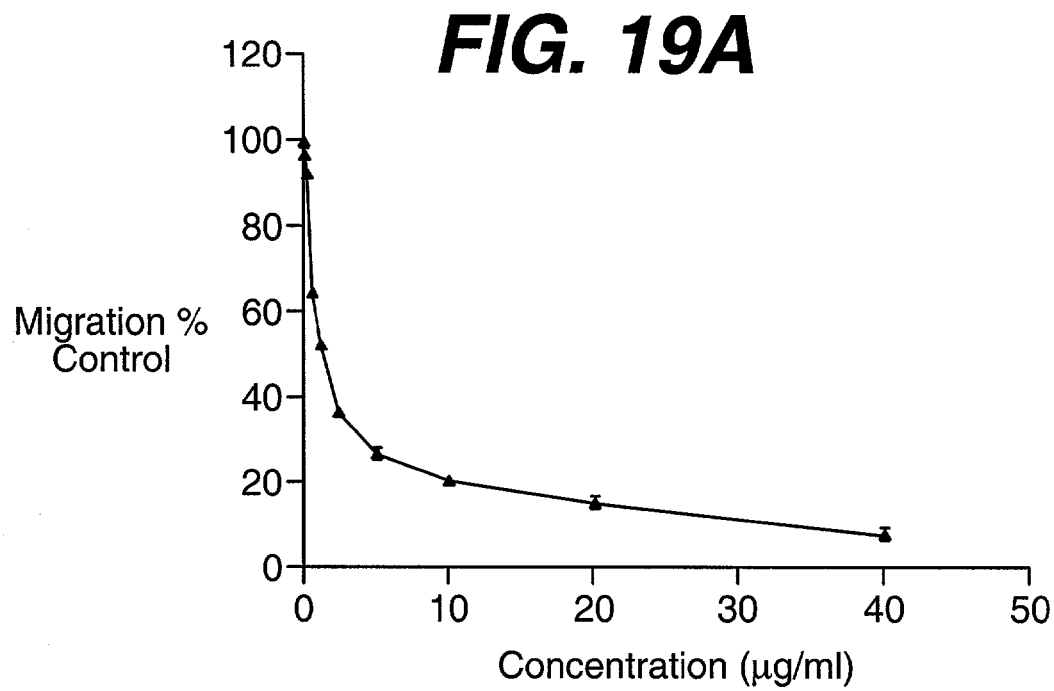
FIG. 19A–E. Migration of A375S.2 cells toward 10% FBS. Migration assay was allowed to proceed for 4 h and the data was captured as described in Methods. Antibodies were used at a concentration of 10 μg/ml.
Figure 19B:
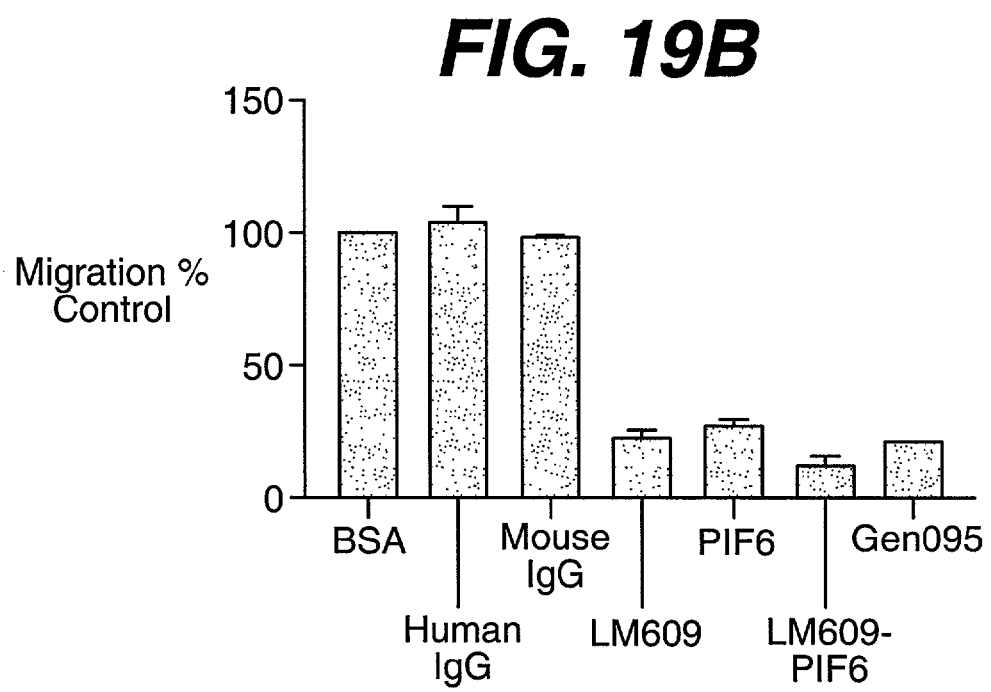
Figure 19C:
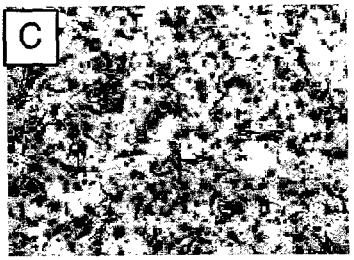
Figure 19D:
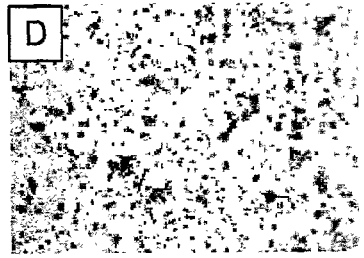
Figure 19E:
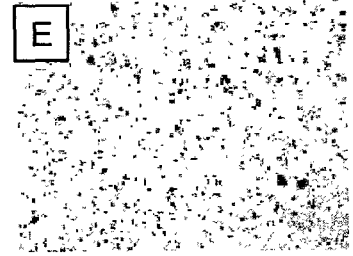

Migration of A375S.2 cells toward 10% FBS. Migration assay was allowed to proceed for 4 h and the data was captured as described in Methods. Antibodies were used at a concentration of 10 µg/ml. FIG. 19(A) is a graphical representation of cell migration in the presence of varying concentrations of Gen095. FIG. 19(B) is a graphical representation of cell migration in the presence of LM609, P1F6, combination of LM609+P1F6, isotype matched control antibodies (human and mouse). The data were normalized to percent of control, which was considered as 100%, and each point is the mean of three transwell filters (+/−SD). Photomicro-graphs are representative fields (10× objective lens) of cell migration in FIG. 19(C), absence of antibody, FIG. 19(D), Gen095 (5 µg/ml), and FIG. 19(E), Gen095 (20 µg/ml).

Results described above indicate that Gen095 blocks tumor and endothelial migration to vitronectin and serum. Next, we determined whether this antibody could inhibit bFGF-stimulated cell migration. As shown in FIG. 9, bFGF stimulated HUVEC cell migration towards vitronectin, and Gen095 significantly blocked this stimulated cell migration.

Figure 20E:
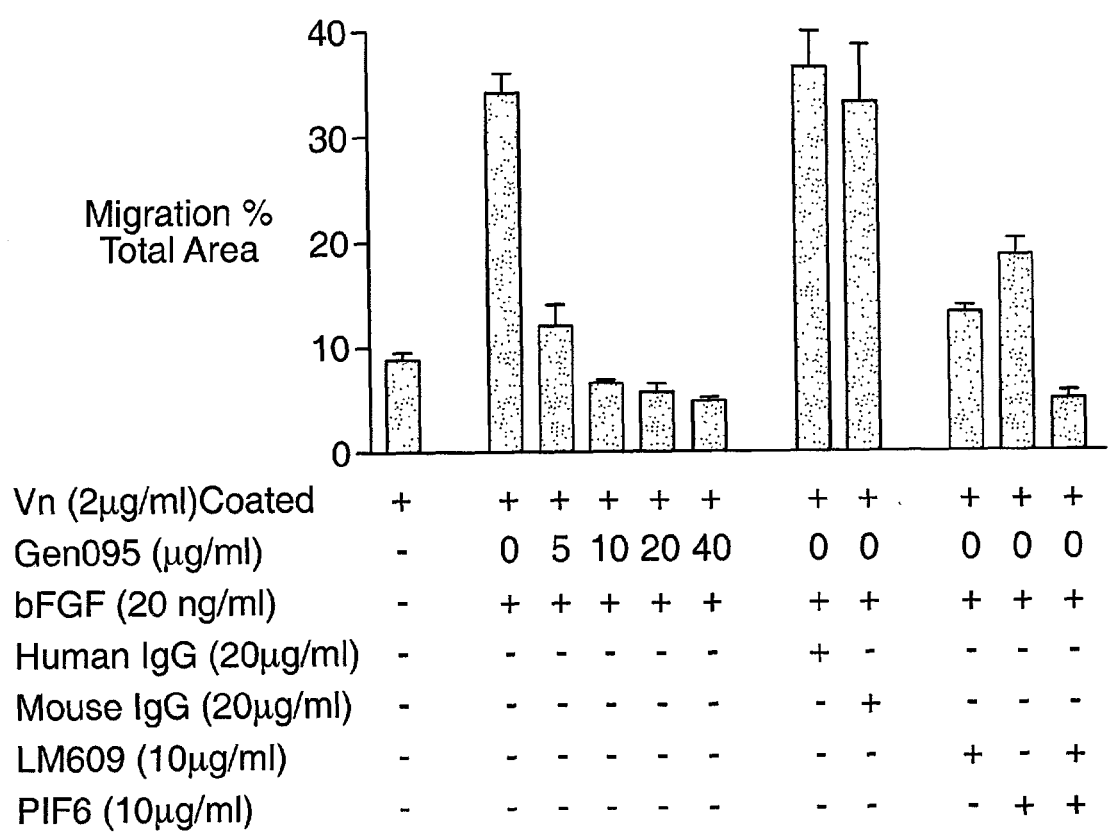

Migration of HUVECS towards vitronectin in the presence of bFGF. The undersides of migration chamber filters were coated with 2 µg/ml vitronectin, and the assay was performed as described in Methods. Cells were allowed to migrate for 6 h. In FIG. 20A–E, each data point is the mean of 3 transwell filters (+/−SD). FIG. 20(A), bFGF; FIG. 20(B), Gen095 (5 µg/ml); FIG. 20(C), Gen095 (40 µg/ml); FIG. 20(D), no-bFGF. FIG. 20(E), Inhibition of cell migration in the presence of various antibodies is shown graphically. Gen095 blocks human melanoma cell invasion Results described above indicate that Gen095 can inhibit cell adhesion and migration. Therefore, we questioned whether this antibody could block tumor cell invasion, a multistep process that involves cell adhesion, degradation of the matrix, and migration of cells through the degraded matrix. We chose fibrin as a matrix for tumor cells because Gen095 was able to block tumor cell adhesion to fibrin (FIG. 3). As shown in FIG. 10, invasion of A375S.2 cells could be inhibited by LM609, suggesting the involvement of at least αvβ3 in this process. Gen095 dose dependently inhibited tumor cell invasion through fibrin. Irrelevant IgG and a mAb directed to platelet GPIIb/IIIa (10E5) served as negative controls. Collectively, these data suggest that Gen095 can effectively block invasion of human melanoma cells.

Figure 21A:
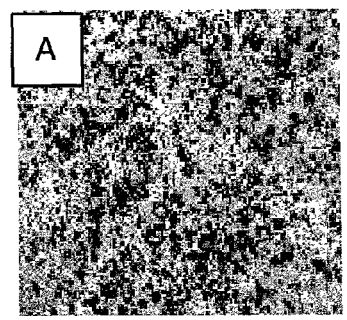
FIG. 21A–D. Invasion of A375S.2 cells through a fibrin gel (5 mg/ml). Invasion assay was allowed to proceed for 24 h and data was captured as decribed in Methods. Photomicrographs are representative fields (4× objective lens) of cell invasion in FIG. 21(A) the absence of antibodies, FIG. 21(B) Gen095 (10 µg/ml), FIG. 21(C) and (D) are graphical representation of cell invasion in presence of Gen095, 10E5 F(ab')$_2$, LM609, P1F6, LM-PIF6 (LM609+P1F6), human and mouse IgGs (H-IgG and M-IgG). Graph
Figure 21B:
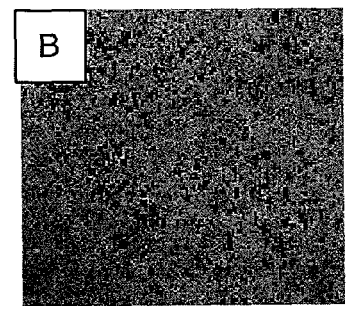
Figure 21C:
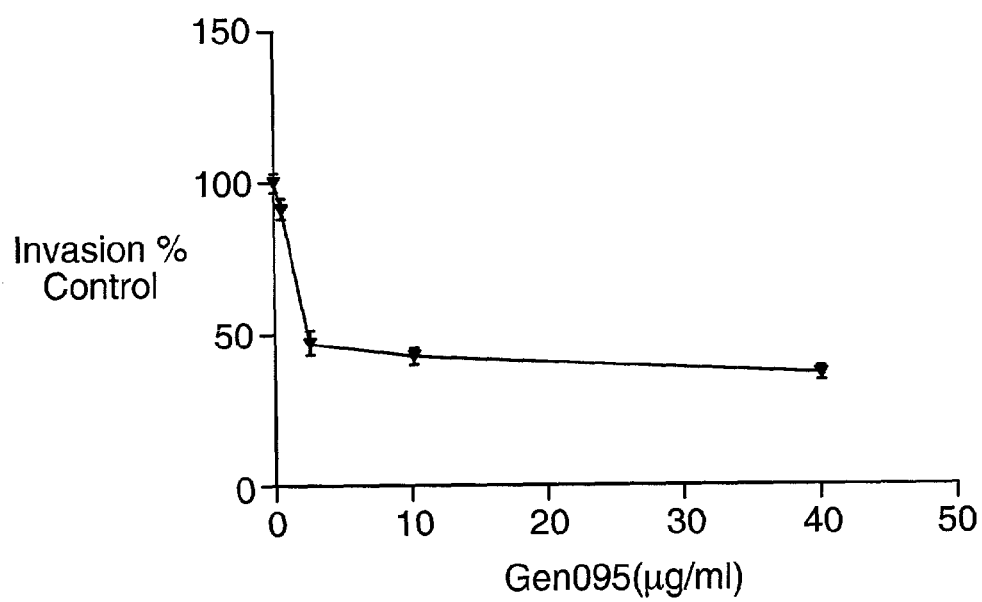
Figure 21D:
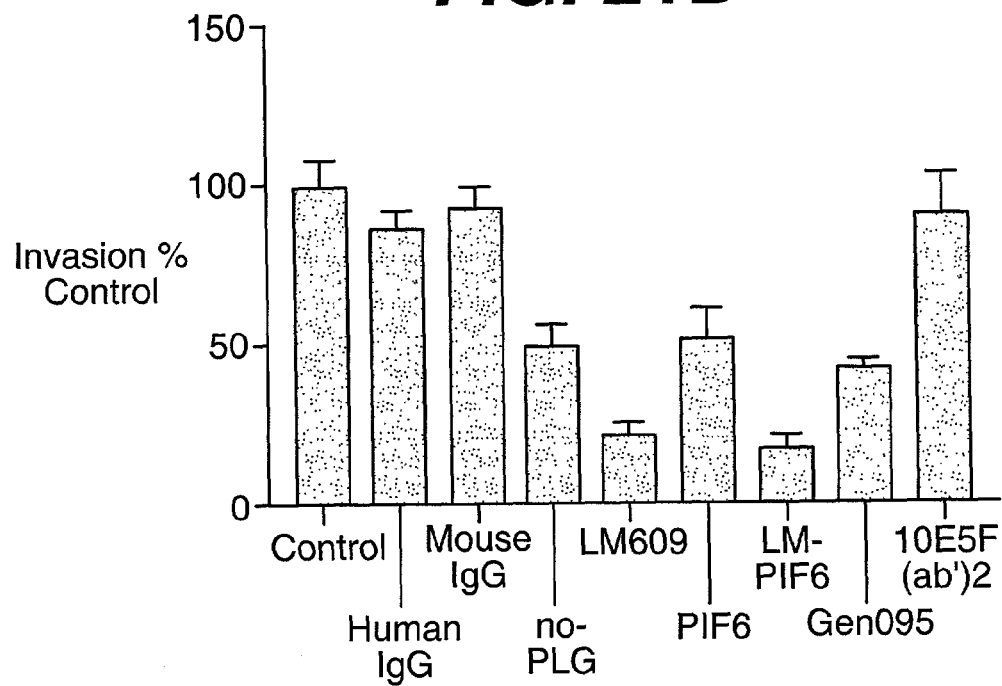

Invasion of A375S.2 cells through a fibrin gel (5 mg/ml). Invasion assay was allowed to proceed for 24 h and data was captured as decribed in Methods. Photomicrographs are representative fields (4× objective lens) of cell invasion in FIG. 21(A) the absence of antibodies, FIG. 21(B) Gen095 (10 µg/ml), FIG. 21(C) and (D) are graphical representation of cell invasion in presence of Gen095, 10E5 F(ab')$_2$, LM609, P1F6, LM-PIF6 (LM609+P1F6), human and mouse IgGs (H-IgG and M-IgG). Graph FIG. 21(D): The concentration of all antibodies and proteins is 10 µg/ml. The data were normalized to percent of control (no antibody) which was considered as 100%, and each point is the mean of three transwell filters (+/−SD).

CONCLUSION

Cell adhesion, migration and invasion requires integrins such as αvβ3 and αvβ5. Gen095 is able to functionally block αvβ3 and αvβ5 integrins that are expressed by endothelial and tumor cells. Gen095 was able to block migration and invasion of cells that were stimulated by bFGF or serum. These results suggest that the Gen095 is a potent inhibitor of tumor and endothelial cell expressed αvβ3 and αvβ5 integrins.

References
1. Taylor, L. D., C. E. Carmack, D. Huszar, K. M. Higgins, R. Mashayekh, G. Sequar, S. R. Schramm, C-C. Kuo, S. L. O'Donnell, R. M. Kay, C. S. Woodhouse, and N. Lonberg. 1993. Human immunoglobulin transgenes undergo rearrangement, somatic mutation and class switching in mice that lack endogenous IgM. International Immunology 6:579–591.

2. Lonberg, N., L. D. Taylor, F. A. Harding, M. Trounstine, K. M. Higgins, S. R. Schramm, C-C. Kuo. R. Mashayekh, K. Wymore, J. G. McCabe, D. Munoz-O'Regan, S. L. O'Donnell, E. S. G. Lapachet, T. Bengoechea, D. M. Fishwild, C. E. Carmack, R. M. Kay, and D. Huszar. 1994. Antigen-specific human antibodies from mice comprising four distinct genetic modifications. Nature 368:856–859.

3. Neuberger, M. 1996. Generating high-avidity human Mabs in mice. Nature Biotechnology 14:826.

4. Fishwild, D. M., S. L. O'Donnell, T. Bengoechea, D. V. Hudson, F. Harding, S. L. Bernhard, D. Jones, R. M. Kay, K. M. Higgins, S. R. Schramm, and N. Lonberg. 1996. High-avidity human IgG monoclonal antibodies from a novel strain of minilocus transgenic mice. Nature Biotechnology 14:845–851.

5. Gastl, G., T. Hermann, M. Steurer, J. Zmija, E. Gunsilius, C. Unger, and A. Kraft. 1997. Angiogenesis as a Target for Tumor Treatment. Oncology 54: 177–184.

6. Eliceiri, B. P., and D. A. Cheresh. 1999. The role of αV integrins during angiogenesis: insights into potential mechanisms of action and clinical development. The Journal of Clinical Investigation 103: 1227–1230.

7. Friedlander M., P. C. Brooks, R. W. Shaffer, C. M. Kincaid, J. A. Varner, and D. A. Cheresh. 1995. Definition of two angiogenic pathways by distinct αV integrins. Science 270: 1500–1502.

It will be clear that the invention can be practiced otherwise than as particularly described in the foregoing description and examples.

Numerous modifications and variations of the present invention are possible in light of the above teachings and, therefore, are within the scope of the appended claims.

---

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 289 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: Human Pancreas
      (B) CLONE: 223187

(xi) SEQUENCE DESCRIPTION: SEQ ID NO:1:

```
ATGAAGGTCT CCGCAGCACT TCTGTGGCTG CTGCTCATAG CAGCTGCCTT CAGCCCCCAG      60

GGGCTCACTG GGCCAGCTTC TGTCCCAACC ACCTGCTGCT TTAACCTGGC CAATAGGAAG     120

ATACCCCTTC AGCGACTAGA GAGCTACAGG AGAATCACCA GTGGCAAATG TCCCCAGAAA     180

GCTGTGATCT TCAAGACCAA ACTGGCCAAG GATATCTGTG CCGACCCCAA GAAGAAGTGG     240

GTGCAGGATT CCATGAAGTA TCTGGACCAA AAATCTCCAA CTCCAAAGC                 289
```

(2) INFORMATION FOR SEQ ID NO:2:

(i) SEQUENCE CHARACTERISTICS:
      (A) LENGTH: 97 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (A) LIBRARY: Human Pancreas
      (B) CLONE: 223187

(xi) SEQUENCE DESCRIPTION: SEQ ID NO:2:

```
Met Lys Val Ser Ala Ala Leu Leu Trp Leu Leu Leu Ile Ala Ala Ala
 1               5                  10                  15

Phe Ser Pro Gln Gly Leu Thr Gly Pro Ala Ser Val Pro Thr Thr Cys
                20                  25                  30
```

-continued

```
Cys Phe Asn Leu Ala Asn Arg Lys Ile Pro Leu Gln Arg Leu Glu Ser
         35                  40                  45

Tyr Arg Arg Ile Thr Ser Gly Lys Cys Pro Gln Lys Ala Val Ile Phe
 50                  55                  60

Lys Thr Lys Leu Ala Lys Asp Ile Cys Ala Asp Pro Lys Lys Lys Trp
 65                  70                  75                  80

Val Gln Asp Ser Met Lys Tyr Leu Asp Gln Lys Ser Pro Thr Pro Lys
                 85                  90                  95

Pro
```

(2) INFORMATION FOR SEQ ID NO:3:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Human Pancreas
        (B) CLONE: 226152

(xi) SEQUENCE DESCRIPTION: SEQ ID NO:3:

```
ATGGCTCAGT CACTGGCTCT GAGCCTCCTT ATCCTGGTTC TGGCCTTTGG CATCCCCAGG      60

ACCCAAGGCA GTGATGGAGG GGCTCAGGAC TGTTGCCTCA AGTACAGCCA AAGGAAGATT     120

CCCGCCAAGG TTGTCCGCAG CTACCGGAAG CAGGAACCAA GCTTAGGCTG CTCCATCCCA     180

GCTATCCTGT TCTTGCCCCG CAAGCGCTCT CAGGCAGAGC TATGTGCAGA CCCAAAGGAG     240

CTCTGGGTGC AGCAGCTGAT GCAGCATCTG GACAAGACAC CATCCCCACA GAAACCAGCC     300

CAGGGCTGCA GGAAGGACAG GGGGGCCTCC AAGACTGGCA AGAAAGGAAA GGGCTCCAAA     360

GGCTGCAAGA GGACTGAGCG GTCACAGACC CCTAAAGGGC CA                        402
```

(2) INFORMATION FOR SEQ ID NO:4:

(i) SEQUENCE CHARACTERISTICS:
        (A) LENGTH: 134 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: Human Pancreas
        (B) CLONE: 226152

(xi) SEQUENCE DESCRIPTION: SEQ ID NO:4:

```
Met Ala Gln Ser Leu Ala Leu Ser Leu Leu Ile Leu Val Leu Ala Phe
 1               5                  10                  15

Gly Ile Pro Arg Thr Gln Gly Ser Asp Gly Gly Ala Gln Asp Cys Cys
                 20                  25                  30

Leu Lys Tyr Ser Gln Arg Lys Ile Pro Ala Lys Val Val Arg Ser Tyr
         35                  40                  45

Arg Lys Gln Glu Pro Ser Leu Gly Cys Ser Ile Pro Ala Ile Leu Phe
 50                  55                  60

Leu Pro Arg Lys Arg Ser Gln Ala Glu Leu Cys Ala Asp Pro Lys Glu
 65                  70                  75                  80

Leu Trp Val Gln Gln Leu Met Gln His Leu Asp Lys Thr Pro Ser Pro
                 85                  90                  95
```

```
Gln Lys Pro Ala Gln Gly Cys Arg Lys Asp Arg Gly Ala Ser Lys Thr
                100                 105                 110

Gly Lys Lys Gly Lys Gly Ser Lys Gly Cys Lys Arg Thr Glu Arg Ser
            115                 120                 125

Gln Thr Pro Lys Gly Pro
    130
```

(2) INFORMATION FOR SEQ ID NO:5:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met Lys Val Ser Ala Ala Leu Leu Ala Leu Leu Ile Ala Ala Ala
 1               5                  10                  15

Phe Cys Pro Gln Gly Leu Ala Gln Pro Asp Gly Val Asp Thr Pro Thr
                20                  25                  30

Thr Cys Cys Phe Asn Tyr Ile Asn Arg Lys Ile Pro Arg Gln Arg Leu
            35                  40                  45

Glu Ser Tyr Arg Arg Ile Thr Ser Ser Lys Cys Ser Lys Pro Ala Val
    50                  55                  60

Ile Phe Lys Thr Lys Arg Ala Lys Gln Val Cys Ala Asp Pro Lys Glu
65                  70                  75                  80

Lys Trp Val Gln Asp Ser Met Lys His Leu Asp Lys Gln Thr Pro Lys
                85                  90                  95

Pro
```

(2) INFORMATION FOR SEQ ID NO:6:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: MIP-1a (xi) SEQUENCE DESCRIPTION: SEQ ID NO:6:

```
Met Gln Val Ser Thr Ala Ala Leu Ala Val Leu Leu Cys Thr Met Ala
 1               5                  10                  15

Leu Cys Asn Gln Phe Ser Ala Ser Leu Ala Ala Asp Thr Pro Thr Ala
                20                  25                  30

Cys Cys Phe Ser Tyr Thr Ser Arg Gln Ile Pro Gln Asn Phe Ile Ala
            35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90
```

(2) INFORMATION FOR SEQ ID NO:7:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: MIP-1b (xi) SEQUENCE DESCRIPTION: SEQ ID NO:7:

```
Met Lys Leu Cys Val Thr Val Leu Ser Leu Leu Met Leu Val Ala Ala
  1               5                  10                  15

Phe Cys Ser Pro Ala Leu Ser Ala Pro Met Gly Ser Asp Pro Pro Thr
                 20                  25                  30

Ala Cys Cys Phe Ser Tyr Thr Ala Arg Lys Leu Pro Arg Asn Phe Val
                 35                  40                  45

Val Asp Tyr Tyr Glu Thr Ser Ser Leu Cys Ser Gln Pro Ala Val Val
 50                  55                  60

Phe Gln Thr Lys Arg Ser Lys Gln Val Cys Ala Asp Pro Ser Glu Ser
 65                  70                  75                  80

Trp Val Gln Glu Tyr Val Tyr Asp Leu Glu Leu Asn
                 85                  90
```

(2) INFORMATION FOR SEQ ID NO:8:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: RANTES (xi) SEQUENCE DESCRIPTION: SEQ ID NO:8:

```
Met Lys Val Ser Ala Ala Arg Leu Ala Val Ile Leu Ile Ala Thr Ala
  1               5                  10                  15

Leu Cys Ala Pro Ala Ser Ala Ser Pro Tyr Ser Ser Asp Thr Thr Pro
                 20                  25                  30

Cys Cys Phe Ala Tyr Ile Ala Arg Pro Leu Pro Arg Ala His Ile Lys
                 35                  40                  45

Glu Tyr Phe Tyr Thr Ser Gly Lys Cys Ser Asn Pro Ala Val Val Phe
 50                  55                  60

Val Thr Arg Lys Asn Arg Gln Val Cys Ala Asn Pro Glu Lys Lys Trp
 65                  70                  75                  80

Val Arg Glu Tyr Ile Asn Ser Leu Glu Met Ser
                 85                  90
```

(2) INFORMATION FOR SEQ ID NO:9:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (vii) IMMEDIATE SOURCE:
    (A) LIBRARY: GenBank
    (B) CLONE: MCP-1

(xi) SEQUENCE DESCRIPTION: SEQ ID NO:9:

```
Met Lys Val Ser Ala Ala Leu Leu Cys Leu Leu Leu Ile Ala Ala Thr
 1               5                  10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
                35                  40                  45

Ala Ser Tyr Arg Arg Ile Thr Ser Ser Lys Cys Pro Lys Glu Ala Val
                50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                    85                  90                  95

Pro Lys Thr
```

(2) INFORMATION FOR SEQ ID NO:10:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: MCP-2

(xi) SEQUENCE DESCRIPTION: SEQ ID NO:10:

```
Ala Gln Pro Asp Ser Val Ser Ile Pro Ile Thr Cys Cys Phe Asn Val
 1               5                  10                  15

Ile Asn Arg Lys Ile Pro Ile Gln Arg Leu Glu Ser Tyr Thr Arg Ile
                20                  25                  30

Thr Asn Ile Gln Cys Pro Lys Glu Ala Val Ile Phe Lys Thr Lys Arg
                35                  40                  45

Gly Lys Glu Val Cys Ala Asp Pro Lys Glu Arg Trp Val Arg Asp Ser
                50                  55                  60

Met Lys His Leu Asp Gln Ile Phe Gln Asn Leu Lys Pro
65                  70                  75
```

(2) INFORMATION FOR SEQ ID NO:11:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: MCP-3

(vi) ORIGINAL SOURCE:

(xi) SEQUENCE DESCRIPTION: SEQ ID NO:11:

Met Trp Lys Pro Met Pro Ser Pro Ser Asn Met Lys Ala Ser Ala Ala

-continued

```
1               5                    10                   15
Leu Leu Cys Leu Leu Thr Ala Ala Ala Phe Ser Pro Gln Gly Leu
            20                  25              30

Ala Gln Pro Val Gly Ile Asn Thr Ser Thr Thr Cys Cys Tyr Arg Phe
        35                  40              45

Ile Asn Lys Lys Ile Pro Lys Gln Arg Leu Glu Ser Tyr Arg Arg Thr
        50                  55              60

Thr Ser Ser His Cys Pro Arg Glu Ala Val Ile Phe Lys Thr Lys Leu
65                  70              75                  80

Asp Lys Glu Ile Cys Ala Asp Pro Thr Gln Lys Trp Val Gln Asp Phe
                85              90                  95

Met Lys His Leu Asp Lys Lys Thr Gln Thr Pro Lys Leu
                100             105
```

What is claimed is:

1. An isolated nucleic acid encoding an isolated mammalian anti-dual integrin antibody comprising (i) all of the heavy chain CDR amino acid sequences of SEQ ID NOS:1, 2, and 3; or (ii) all of the light chain CDR amino acids sequences of SEQ ID NOS:4, 5, and 6.

2. An isolated nucleic acid vector comprising an isolated nucleic acid according to claim 1.

3. A prokaryotic or eukaryotic host cell comprising an isolated nucleic acid according to claim 2.

4. A host cell according to claim 3, wherein said host cell is at least one selected from COS-1, COS-7, HEK293, BHK21, CHO, BSC-1, Hep G2, P3X63Ag8.653, SP2/0, HeLa, myeloma, or lymphoma cells.

5. A method for producing an anti-dual integrin antibody, comprising translating a nucleic acid vector according to claim 2 under conditions in vitro or in vivo, such that the dual integrin antibody is expressed in detectable or recoverable amounts.

6. An isolated nucleic acid encoding a human monoclonal antibody comprising human heavy chain and human light chain variable regions comprising the amino acid sequences shown in SEQ ID NO: 7 and SEQ ID NO: 8, respectively.

7. An isolated nucleic acid vector comprising an isolated nucleic acid according to claim 6.

8. A prokaryotic or eukaryotic host cell comprising an isolated nucleic acid vector according to claim 7.

9. A host cell according to claim 8, wherein said host cell is at least one selected from COS-1, COS-7, HEK293, BHK21, CHO, BSC-1, Hep G2, P3X63Ag8.653, SP2/0, 293, HeLa, myeloma, or lymphoma cells.

10. A method for producing an anti-dual integrin antibody, comprising translating a nucleic acid vector according to claim 7 under conditions in vitro or in vivo, such that the dual integrin antibody is expressed in detectable or recoverable amounts.

11. An isolated nucleic acid according to claim 6 wherein the antibody completely inhibits M21 cell adhesion to vitronectin.

12. An isolated nucleic acid according to claim 6 wherein the antibody comprises a human IgG heavy chain and a human kappa light chain.

13. An isolated nucleic acid according to claim 6 wherein the antibody comprises an IgG1 or IgG3 heavy chain.

14. An isolated nucleic acid according to claim 6 wherein the antibody is an IgG1kappa antibody.

* * * * *

UNITED STATES PATENT AND TRADEMARK OFFICE
CERTIFICATE OF CORRECTION

| | | |
|---|---|---|
| PATENT NO. | : 7,288,390 B2 | Page 1 of 18 |
| APPLICATION NO. | : 09/920267 | |
| DATED | : October 30, 2007 | |
| INVENTOR(S) | : Heavner et al. | |

It is certified that error appears in the above-identified patent and that said Letters Patent is hereby corrected as shown below:

Column 69, line 20 to Column 79, line 18: cancel the Sequence Listing beginning with "(1) GENERAL INFORMATION:" and ending with "Leu" in column 79, line 18, and insert the following Sequence Listing:

Signed and Sealed this
Fourth Day of January, 2011

David J. Kappos
*Director of the United States Patent and Trademark Office*

```
                                SEQUENCE LISTING

<110>  Centocor, Inc.
           Giles-Komar, Jill
           Trikha, Mohit
           Snyder, Linda
           Nakada, Marian

<120>  ANTI-DUAL INTEGRIN ANTIBODIES, COMPOSITINS, METHODS AND USES

<130>  CEN 249

<140>  US 09/920,267
    <141>  2001-08-01

<150>  60/223,363
    <151>  2000-08-07

<160>  17

<170>  PatentIn version 3.1

<210>  1
    <211>  5
    <212>  PRT
    <213>  Homo sapiens

<400>  1

Arg Tyr Thr Met His
    1               5

<210>  2
    <211>  17
    <212>  PRT
    <213>  Homo sapiens

<400>  2

Val Ile Ser Phe Asp Gly Ser Asn Lys Tyr Tyr Val Asp Ser Val Lys
    1               5                  10                  15

Gly

<210>  3
    <211>  10
    <212>  PRT
    <213>  Homo sapiens

<400>  3

Glu Ala Arg Gly Ser Tyr Ala Phe Asp Ile
    1               5                  10
```

```
<210>  4
<211>  11
<212>  PRT
<213>  Homo sapiens

<400>  4

Arg Ala Ser Gln Ser Val Ser Ser Tyr Leu Ala
1               5                   10

<210>  5
<211>  7
<212>  PRT
<213>  Homo sapiens

<400>  5

Asp Ala Ser Asn Arg Ala Thr
1               5

<210>  6
<211>  8
<212>  PRT
<213>  Homo sapiens

<400>  6

Gln Gln Arg Ser Asn Trp Pro Pro
1               5

<210>  7
<211>  119
<212>  PRT
<213>  Homo sapiens

<400>  7

Gln Val Gln Leu Val Glu Ser Gly Gly Gly Val Val Gln Pro Gly Arg
1               5                   10                  15

Ser Arg Arg Leu Ser Cys Ala Ala Ser Gly Phe Thr Phe Ser Arg Tyr
            20                  25                  30

Thr Met His Trp Val Arg Gln Ala Pro Gly Lys Gly Leu Glu Trp Val
        35                  40                  45

Ala Val Ile Ser Phe Asp Gly Ser Asn Lys Tyr Tyr Val Asp Ser Val
    50                  55                  60
```

```
Lys Gly Arg Phe Thr Ile Ser Arg Asp Asn Ser Glu Asn Thr Leu Tyr
 65              70                  75                  80

Leu Gln Val Asn Ile Leu Arg Ala Glu Asp Thr Ala Val Tyr Tyr Cys
             85                  90                  95

Ala Arg Glu Ala Arg Gly Ser Tyr Ala Phe Asp Ile Trp Gly Gln Gly
            100                 105                 110

Thr Met Val Thr Val Ser Ser
        115

<210>  8
<211>  108
<212>  PRT
<213>  Homo sapiens

<400>  8

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65              70                  75                  80

Glu Asp Phe Ala Val Tyr Tyr Cys Gln Gln Arg Ser Asn Trp Pro Pro
             85                  90                  95

Phe Thr Phe Gly Pro Gly Thr Lys Val Asp Ile Lys
            100                 105

<210>  9
<211>  1048
<212>  PRT
<213>  Homo sapiens
```

<400> 9

```
Met Ala Phe Pro Pro Arg Arg Arg Leu Arg Leu Gly Pro Arg Gly Leu
1               5                   10                  15

Pro Leu Leu Leu Ser Gly Leu Leu Leu Pro Leu Cys Arg Ala Phe Asn
            20                  25                  30

Leu Asp Val Asp Ser Pro Ala Glu Tyr Ser Gly Pro Glu Gly Ser Tyr
            35                  40                  45

Phe Gly Phe Ala Val Asp Phe Phe Val Pro Ser Ala Ser Ser Arg Met
        50                  55                  60

Phe Leu Leu Val Gly Ala Pro Lys Ala Asn Thr Thr Gln Pro Gly Ile
65                  70                  75                  80

Val Glu Gly Gly Gln Val Leu Lys Cys Asp Trp Ser Ser Thr Arg Arg
                85                  90                  95

Cys Gln Pro Ile Glu Phe Asp Ala Thr Gly Asn Arg Asp Tyr Ala Lys
                100                 105                 110

Asp Asp Pro Leu Glu Phe Lys Ser His Gln Trp Phe Gly Ala Ser Val
            115                 120                 125

Arg Ser Lys Gln Asp Lys Ile Leu Ala Cys Ala Pro Leu Tyr His Trp
        130                 135                 140

Arg Thr Glu Met Lys Gln Glu Arg Glu Pro Val Gly Thr Cys Phe Leu
145                 150                 155                 160

Gln Asp Gly Thr Lys Thr Val Glu Tyr Ala Pro Cys Arg Ser Gln Asp
                165                 170                 175

Ile Asp Ala Asp Gly Gln Gly Phe Cys Gln Gly Gly Phe Ser Ile Asp
            180                 185                 190

Phe Thr Lys Ala Asp Arg Val Leu Leu Gly Gly Pro Gly Ser Phe Tyr
        195                 200                 205

Trp Gln Gly Gln Leu Ile Ser Asp Gln Val Ala Glu Ile Val Ser Lys
210                 215                 220
```

```
Tyr Asp Pro Asn Val Tyr Ser Ile Lys Tyr Asn Asn Gln Leu Ala Thr
225                 230                 235                 240

Arg Thr Ala Gln Ala Ile Phe Asp Asp Ser Tyr Leu Gly Tyr Ser Val
            245                 250                 255

Ala Val Gly Asp Phe Asn Gly Asp Gly Ile Asp Asp Phe Val Ser Gly
            260                 265                 270

Val Pro Arg Ala Ala Arg Thr Leu Gly Met Val Tyr Ile Tyr Asp Gly
            275                 280                 285

Lys Asn Met Ser Ser Leu Tyr Asn Phe Thr Gly Glu Gln Met Ala Ala
            290                 295                 300

Tyr Phe Gly Phe Ser Val Ala Ala Thr Asp Ile Asn Gly Asp Asp Tyr
305                 310                 315                 320

Ala Asp Val Phe Ile Gly Ala Pro Leu Phe Met Asp Arg Gly Ser Asp
                325                 330                 335

Gly Lys Leu Gln Glu Val Gly Gln Val Ser Val Ser Leu Gln Arg Ala
            340                 345                 350

Ser Gly Asp Phe Gln Thr Thr Lys Leu Asn Gly Phe Glu Val Phe Ala
            355                 360                 365

Arg Phe Gly Ser Ala Ile Ala Pro Leu Gly Asp Leu Asp Gln Asp Gly
    370                 375                 380

Phe Asn Asp Ile Ala Ile Ala Ala Pro Tyr Gly Gly Glu Asp Lys Lys
385                 390                 395                 400

Gly Ile Val Tyr Ile Phe Asn Gly Arg Ser Thr Gly Leu Asn Ala Val
                405                 410                 415

Pro Ser Gln Ile Leu Glu Gly Gln Trp Ala Ala Arg Ser Met Pro Pro
            420                 425                 430

Ser Phe Gly Tyr Ser Met Lys Gly Ala Thr Asp Ile Asp Lys Asn Gly
            435                 440                 445
```

```
Tyr Pro Asp Leu Ile Val Gly Ala Phe Gly Val Asp Arg Ala Ile Leu
    450             455                 460

Tyr Arg Ala Arg Pro Val Ile Thr Val Asn Ala Gly Leu Glu Val Tyr
465             470                 475                 480

Pro Ser Ile Leu Asn Gln Asp Asn Lys Thr Cys Ser Leu Pro Gly Thr
                485                 490                 495

Ala Leu Lys Val Ser Cys Phe Asn Val Arg Phe Cys Leu Lys Ala Asp
                500             505                 510

Gly Lys Gly Val Leu Pro Arg Lys Leu Asn Phe Gln Val Glu Leu Leu
        515                 520                 525

Leu Asp Lys Leu Lys Gln Lys Gly Ala Ile Arg Arg Ala Leu Phe Leu
    530             535                 540

Tyr Ser Arg Ser Pro Ser His Ser Lys Asn Met Thr Ile Ser Arg Gly
545             550                 555                 560

Gly Leu Met Gln Cys Glu Glu Leu Ile Ala Tyr Leu Arg Asp Glu Ser
                565                 570                 575

Glu Phe Arg Asp Lys Leu Thr Pro Ile Thr Ile Phe Met Glu Tyr Arg
            580                 585                 590

Leu Asp Tyr Arg Thr Ala Ala Asp Thr Thr Gly Leu Gln Pro Ile Leu
        595                 600                 605

Asn Gln Phe Thr Pro Ala Asn Ile Ser Arg Gln Ala His Ile Leu Leu
    610                 615                 620

Asp Cys Gly Glu Asp Asn Val Cys Lys Pro Lys Leu Glu Val Ser Val
625                 630                 635                 640

Asp Ser Asp Gln Lys Lys Ile Tyr Ile Gly Asp Asp Asn Pro Leu Thr
            645                 650                 655

Leu Ile Val Lys Ala Gln Asn Gln Gly Glu Gly Ala Tyr Glu Ala Glu
        660                 665                 670

Leu Ile Val Ser Ile Pro Leu Gln Ala Asp Phe Ile Gly Val Val Arg
```

```
                675                 680                 685

Asn Asn Glu Ala Leu Ala Arg Leu Ser Cys Ala Phe Lys Thr Glu Asn
    690             695             700

Gln Thr Arg Gln Val Val Cys Asp Leu Gly Asn Pro Met Lys Ala Gly
705             710             715                 720

Thr Gln Leu Leu Ala Gly Leu Arg Phe Ser Val His Gln Gln Ser Glu
            725             730             735

Met Asp Thr Ser Val Lys Phe Asp Leu Gln Ile Gln Ser Ser Asn Leu
            740             745             750

Phe Asp Lys Val Ser Pro Val Val Ser His Lys Val Asp Leu Ala Val
        755             760             765

Leu Ala Ala Val Glu Ile Arg Gly Val Ser Ser Pro Asp His Ile Phe
        770             775             780

Leu Pro Ile Pro Asn Trp Glu His Lys Glu Asn Pro Glu Thr Glu Glu
785             790             795                 800

Asp Val Gly Pro Val Val Gln His Ile Tyr Glu Leu Arg Asn Asn Gly
                805             810             815

Pro Ser Ser Phe Ser Lys Ala Met Leu His Leu Gln Trp Pro Tyr Lys
            820             825             830

Tyr Asn Asn Asn Thr Leu Leu Tyr Ile Leu His Tyr Asp Ile Asp Gly
        835             840             845

Pro Met Asn Cys Thr Ser Asp Met Glu Ile Asn Pro Leu Arg Ile Lys
    850             855             860

Ile Ser Ser Leu Gln Thr Thr Glu Lys Asn Asp Thr Val Ala Gly Gln
865             870             875                 880

Gly Glu Arg Asp His Leu Ile Thr Lys Arg Asp Leu Ala Leu Ser Glu
            885             890             895

Gly Asp Ile His Thr Leu Gly Cys Gly Val Ala Gln Cys Leu Lys Ile
            900             905             910
```

```
Val Cys Gln Val Gly Arg Leu Asp Arg Gly Lys Ser Ala Ile Leu Tyr
        915                 920                 925

Val Lys Ser Leu Leu Trp Thr Glu Thr Phe Met Asn Lys Glu Asn Gln
        930                 935                 940

Asn His Ser Tyr Ser Leu Lys Ser Ser Ala Ser Phe Asn Val Ile Glu
945                 950                 955                 960

Phe Pro Tyr Lys Asn Leu Pro Ile Glu Asp Ile Thr Asn Ser Thr Leu
                965                 970                 975

Val Thr Thr Asn Val Thr Trp Gly Ile Gln Pro Ala Pro Met Pro Val
                980                 985                 990

Pro Val Trp Val Ile Ile Leu Ala  Val Leu Ala Gly Leu  Leu Leu Leu
        995                 1000                1005

Ala Val  Leu Val Phe Val Met  Tyr Arg Met Gly Phe  Phe Lys Arg
    1010                 1015                1020

Val Arg  Pro Pro Gln Glu Glu  Gln Glu Arg Glu Gln  Leu Gln Pro
    1025                 1030                1035

His Glu  Asn Gly Glu Gly Asn  Ser Glu Thr
    1040                 1045

<210>  10
<211>  15
<212>  DNA
<213>  Homo sapiens

<400>  10
agatatacta tgcac                                                    15

<210>  11
<211>  51
<212>  DNA
<213>  Homo sapiens

<400>  11
gttatatcat tgatggaag caataaatac tacgtagact ccgtgaaggg c              51

<210>  12
```

<211> 30
<212> DNA
<213> Homo sapiens

<400> 12
gaggcccggg gatcgtatgc ttttgatatc                                30

<210> 13
<211> 42
<212> DNA
<213> Homo sapiens

<400> 13
ctctcctgca gggccagtca gagtgttagc agctacttag cc                  42

<210> 14
<211> 18
<212> DNA
<213> Homo sapiens

<400> 14
gatgcatcca acagggcc                                             18

<210> 15
<211> 21
<212> DNA
<213> Homo sapiens

<400> 15
cagcagcgta gcaactggcc t                                         21

<210> 16
<211> 788
<212> PRT
<213> Homo sapiens

<400> 16

Met Arg Ala Arg Pro Arg Pro Arg Pro Leu Trp Ala Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
        35                  40                  45

Cys Ala Trp Cys Ser Asp Glu Ala Leu Pro Leu Gly Ser Pro Arg Cys
    50                  55                  60

```
Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
        130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
        195                 200                 205

Thr Cys Leu Pro Met Phe Gly Tyr Lys His Val Leu Thr Leu Thr Asp
    210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn Asp Ala Ser His Leu Leu
            260                 265                 270

Val Phe Thr Thr Asp Ala Lys Thr His Ile Ala Leu Asp Gly Arg Leu
        275                 280                 285
```

Ala Gly Ile Val Gln Pro Asn Asp Gly Gln Cys His Val Gly Ser Asp
290             295             300

Asn His Tyr Ser Ala Ser Thr Thr Met Asp Tyr Pro Ser Leu Gly Leu
305             310             315             320

Met Thr Glu Lys Leu Ser Gln Lys Asn Ile Asn Leu Ile Phe Ala Val
            325             330             335

Thr Glu Asn Val Val Asn Leu Tyr Gln Asn Tyr Ser Glu Leu Ile Pro
            340             345             350

Gly Thr Thr Val Gly Val Leu Ser Met Asp Ser Ser Asn Val Leu Gln
            355             360             365

Leu Ile Val Asp Ala Tyr Gly Lys Ile Arg Ser Lys Val Glu Leu Glu
            370             375             380

Val Arg Asp Leu Pro Glu Glu Leu Ser Leu Ser Phe Asn Ala Thr Cys
385             390             395             400

Leu Asn Asn Glu Val Ile Pro Gly Leu Lys Ser Cys Met Gly Leu Lys
            405             410             415

Ile Gly Asp Thr Val Ser Phe Ser Ile Glu Ala Lys Val Arg Gly Cys
            420             425             430

Pro Gln Glu Lys Glu Lys Ser Phe Thr Ile Lys Pro Val Gly Phe Lys
            435             440             445

Asp Ser Leu Ile Val Gln Val Thr Phe Asp Cys Asp Cys Ala Cys Gln
            450             455             460

Ala Gln Ala Glu Pro Asn Ser His Arg Cys Asn Asn Gly Asn Gly Thr
465             470             475             480

Phe Glu Cys Gly Val Cys Arg Cys Gly Pro Gly Trp Leu Gly Ser Gln
            485             490             495

Cys Glu Cys Ser Glu Glu Asp Tyr Arg Pro Ser Gln Gln Asp Glu Cys
            500             505             510

Ser Pro Arg Glu Gly Gln Pro Val Cys Ser Gln Arg Gly Glu Cys Leu

CERTIFICATE OF CORRECTION (continued)
U.S. Pat. No. 7,288,390 B2

```
              515                    520                      525
     Cys Gly Gln Cys Val Cys His Ser Ser Asp Phe Gly Lys Ile Thr Gly
         530              535              540

Lys Tyr Cys Glu Cys Asp Asp Phe Ser Cys Val Arg Tyr Lys Gly Glu
     545              550              555                      560

Met Cys Ser Gly His Gly Gln Cys Ser Cys Gly Asp Cys Leu Cys Asp
                     565              570              575

Ser Asp Trp Thr Gly Tyr Tyr Cys Asn Cys Thr Thr Arg Thr Asp Thr
                 580              585              590

Cys Met Ser Ser Asn Gly Leu Leu Cys Ser Gly Arg Gly Lys Cys Glu
             595              600              605

Cys Gly Ser Cys Val Cys Ile Gln Pro Gly Ser Tyr Gly Asp Thr Cys
         610              615              620

Glu Lys Cys Pro Thr Cys Pro Asp Ala Cys Thr Phe Lys Lys Glu Cys
     625              630              635                      640

Val Glu Cys Lys Lys Phe Asp Arg Glu Pro Tyr Met Thr Glu Asn Thr
                     645              650                      655

Cys Asn Arg Tyr Cys Arg Asp Glu Ile Glu Ser Val Lys Glu Leu Lys
                     660              665              670

Asp Thr Gly Lys Asp Ala Val Asn Cys Thr Tyr Lys Asn Glu Asp Asp
                 675              680              685

Cys Val Val Arg Phe Gln Tyr Tyr Glu Asp Ser Ser Gly Lys Ser Ile
             690              695              700

Leu Tyr Val Val Glu Glu Pro Glu Cys Pro Lys Gly Pro Asp Ile Leu
     705              710              715                      720

Val Val Leu Leu Ser Val Met Gly Ala Ile Leu Leu Ile Gly Leu Ala
                     725              730              735

Ala Leu Leu Ile Trp Lys Leu Leu Ile Thr Ile His Asp Arg Lys Glu
                 740              745              750
```

```
Phe Ala Lys Phe Glu Glu Arg Ala Arg Ala Lys Trp Asp Thr Ala
        755                 760             765

Asn Asn Pro Leu Tyr Lys Glu Ala Thr Ser Thr Phe Thr Asn Ile Thr
        770             775             780

Tyr Arg Gly Thr
785

<210> 17
<211> 799
<212> PRT
<213> Homo sapiens

<400> 17

Met Pro Arg Ala Pro Ala Pro Leu Tyr Ala Cys Leu Leu Gly Leu Cys
1               5                   10                  15

Ala Leu Leu Pro Arg Leu Ala Gly Leu Asn Ile Cys Thr Ser Gly Ser
            20                  25                  30

Ala Thr Ser Cys Glu Glu Cys Leu Leu Ile His Pro Lys Cys Ala Trp
            35                  40                  45

Cys Ser Lys Glu Asp Phe Gly Ser Pro Arg Ser Ile Thr Ser Arg Cys
        50                  55                  60

Asp Leu Arg Ala Asn Leu Val Lys Asn Gly Cys Gly Gly Glu Ile Glu
65                  70                  75                  80

Ser Pro Ala Ser Ser Phe His Val Leu Arg Ser Leu Pro Leu Ser Ser
                85                  90                  95

Lys Gly Ser Gly Ser Ala Gly Trp Asp Val Ile Gln Met Thr Pro Gln
                100                 105                 110

Glu Ile Ala Val Asn Leu Arg Pro Gly Asp Lys Thr Thr Phe Gln Leu
            115                 120                 125

Gln Val Arg Gln Val Glu Asp Tyr Pro Val Asp Leu Tyr Tyr Leu Met
        130                 135                 140
```

```
Asp Leu Ser Leu Ser Met Lys Asp Asp Leu Asp Asn Ile Arg Ser Leu
145                 150                 155                 160

Gly Thr Lys Leu Ala Glu Glu Met Arg Lys Leu Thr Ser Asn Phe Arg
            165                 170                 175

Leu Gly Phe Gly Ser Phe Val Asp Lys Asp Ile Ser Pro Phe Ser Tyr
            180                 185                 190

Thr Ala Pro Arg Tyr Gln Thr Asn Pro Cys Ile Gly Tyr Lys Leu Phe
            195                 200                 205

Pro Asn Cys Val Pro Ser Phe Gly Phe Arg His Leu Leu Pro Leu Thr
            210                 215                 220

Asp Arg Val Asp Ser Phe Asn Glu Glu Val Arg Lys Gln Arg Val Ser
225                 230                 235                 240

Arg Asn Arg Asp Ala Pro Glu Gly Gly Phe Asp Ala Val Leu Gln Ala
            245                 250                 255

Ala Val Cys Lys Glu Lys Ile Gly Trp Arg Lys Asp Ala Leu His Leu
            260                 265                 270

Leu Val Phe Thr Thr Asp Asp Val Pro His Ile Ala Leu Asp Gly Lys
            275                 280                 285

Leu Gly Gly Leu Val Gln Pro His Asp Gly Gln Cys His Leu Asn Glu
            290                 295                 300

Ala Asn Glu Tyr Thr Ala Ser Asn Gln Met Asp Tyr Pro Ser Leu Ala
305                 310                 315                 320

Leu Leu Gly Glu Lys Leu Ala Glu Asn Asn Ile Asn Leu Ile Phe Ala
            325                 330                 335

Val Thr Lys Asn His Tyr Met Leu Tyr Lys Asn Phe Thr Ala Leu Ile
            340                 345                 350

Pro Gly Thr Thr Val Glu Ile Leu Asp Gly Asp Ser Lys Asn Ile Ile
            355                 360                 365

Gln Leu Ile Ile Asn Ala Tyr Asn Ser Ile Arg Ser Lys Val Glu Leu
```

CERTIFICATE OF CORRECTION (continued)
U.S. Pat. No. 7,288,390 B2

```
             370                      375                       380

Ser Val Trp Asp Gln Pro Glu Asp Leu Asn Leu Phe Phe Thr Ala Thr
   385                 390                 395                 400

Cys Gln Asp Gly Val Ser Tyr Pro Gly Gln Arg Lys Cys Glu Gly Leu
                   405                 410                 415

Lys Ile Gly Asp Thr Ala Ser Phe Glu Val Ser Leu Glu Ala Arg Ser
                   420                 425                 430

Cys Pro Ser Arg His Thr Glu His Val Phe Ala Leu Arg Pro Val Gly
                   435                 440                 445

Phe Arg Asp Ser Leu Glu Val Gly Val Thr Tyr Asn Cys Thr Cys Gly
                   450                 455                 460

Cys Ser Val Gly Leu Glu Pro Asn Ser Ala Arg Cys Asn Gly Ser Gly
   465                 470                 475                 480

Thr Tyr Val Cys Gly Leu Cys Glu Cys Ser Pro Gly Tyr Leu Gly Thr
                   485                 490                 495

Arg Cys Glu Cys Gln Asp Gly Glu Asn Gln Ser Val Tyr Gln Asn Leu
                   500                 505                 510

Cys Arg Glu Ala Glu Gly Lys Pro Leu Cys Ser Gly Arg Gly Asp Cys
                   515                 520                 525

Ser Cys Asn Gln Cys Ser Cys Phe Glu Ser Glu Phe Gly Lys Ile Tyr
   530                 535                 540

Gly Pro Phe Cys Glu Cys Asp Asn Phe Ser Cys Ala Arg Asn Lys Gly
   545                 550                 555                 560

Val Leu Cys Ser Gly His Gly Glu Cys His Cys Gly Glu Cys Lys Cys
                   565                 570                 575

His Ala Gly Tyr Ile Gly Asp Asn Cys Asn Cys Ser Thr Asp Ile Ser
                   580                 585                 590

Thr Cys Arg Gly Arg Asp Gly Gln Ile Cys Ser Glu Arg Gly His Cys
                   595                 600                 605
```

```
Leu Cys Gly Gln Cys Gln Cys Thr Glu Pro Gly Ala Phe Gly Glu Met
    610             615             620

Cys Glu Lys Cys Pro Thr Cys Pro Asp Ala Cys Ser Thr Lys Arg Asp
625             630             635                         640

Cys Val Glu Cys Leu Leu Leu His Ser Gly Lys Pro Asp Asn Gln Thr
            645             650                     655

Cys His Ser Leu Cys Arg Asp Glu Val Ile Thr Trp Val Asp Thr Ile
            660             665             670

Val Lys Asp Asp Gln Glu Ala Val Leu Cys Phe Tyr Lys Thr Ala Lys
        675             680             685

Asp Cys Val Met Met Phe Thr Tyr Val Glu Leu Pro Ser Gly Lys Ser
    690             695             700

Asn Leu Thr Val Leu Arg Glu Pro Glu Cys Gly Asn Thr Pro Asn Ala
705             710             715                         720

Met Thr Ile Leu Leu Ala Val Val Gly Ser Ile Leu Leu Val Gly Leu
            725             730             735

Ala Leu Leu Ala Ile Trp Lys Leu Leu Val Thr Ile His Asp Arg Arg
            740             745             750

Glu Phe Ala Lys Phe Gln Ser Glu Arg Ser Arg Ala Arg Tyr Glu Met
        755             760             765

Ala Ser Asn Pro Leu Tyr Arg Lys Pro Ile Ser Thr His Thr Val Asp
770             775             780

Phe Thr Phe Asn Lys Phe Asn Lys Ser Tyr Asn Gly Thr Val Asp
785             790             795                         --
```

Claim 1, Column 79, line 25, delete "or" and insert --and--.

With the above correction, Claim 1 reads:

1. An isolated nucleic acid encoding an isolated mammalian anti-dual integrin antibody comprising (i) all of the heavy chain CDR amino acid sequences of SEQ ID NOS:1, 2, and 3; and (ii) all of the light chain CDR amino acids sequences of SEQ ID NOS:4, 5, and 6.

CERTIFICATE OF CORRECTION (continued)
U.S. Pat. No. 7,288,390 B2

Claim 3, Column 79, line 29, insert --vector-- between "acid" and "according".

With the above correction, Claim 3 reads:

3. A prokaryotic or eukaryotic host cell comprising an isolated nucleic acid vector according to claim 2.

Claim 9, Column 80, line 26, delete "293," before "HeLa".

With the above correction, Claim 9 reads:

9. A host cell according to claim 8, wherein said host cell is at least one selected from COS-1, COS-7, HEK293, BHK21, CHO, BSC-1, Hep G2, P3X63Ag8.653, SP2/0, HeLa, myeloma, or lymphoma cells.